(12) United States Patent
Lamego et al.

(10) Patent No.: US 11,317,283 B1
(45) Date of Patent: Apr. 26, 2022

(54) SINGLE USE MEDICAL DEVICE APPARATUS AND METHODS

(71) Applicant: TRUE WEARABLES, INC., Rancho Santa Margarita, CA (US)

(72) Inventors: Marcelo Malini Lamego, Mission Viejo, CA (US); Tatiana Buticosky Lamego, Mission Viejo, CA (US)

( * ) Notice: Subject to any disclaimer, the term of this patent is extended or adjusted under 35 U.S.C. 154(b) by 115 days.

(21) Appl. No.: 16/817,481

(22) Filed: Mar. 12, 2020

Related U.S. Application Data

(63) Continuation of application No. 16/274,207, filed on Feb. 12, 2019, now Pat. No. 10,659,963.

(Continued)

(51) Int. Cl.
*H04W 12/06* (2021.01)
*H04W 76/14* (2018.01)
(Continued)

(52) U.S. Cl.
CPC ........... *H04W 12/06* (2013.01); *A61B 5/0002* (2013.01); *A61B 5/1455* (2013.01);
(Continued)

(58) Field of Classification Search
CPC .... H04W 12/06; H04W 76/14; A61B 5/0002; A61B 5/1455; A61B 5/6814;
(Continued)

(56) References Cited

U.S. PATENT DOCUMENTS

| 2,567,926 A | 9/1951 | Dunkelberger |
| 2,706,927 A | 4/1955 | Howard |

(Continued)

FOREIGN PATENT DOCUMENTS

| EP | 3386390 | 10/2017 |
| GB | 2560482 | 9/2018 |

(Continued)

OTHER PUBLICATIONS

U.S. Appl. No. 16/551,437, Office Action dated Jun. 10, 2021, 12 pages.

(Continued)

*Primary Examiner* — Sisay Yacob
(74) *Attorney, Agent, or Firm* — Merchant & Gould P.C.

(57) ABSTRACT

A medical device includes a printed circuit board-battery assembly, a tape encapsulation assembly wrapped around the PCB-battery assembly, and a second removable tab positioned on a surface of the tape encapsulation assembly. The second removable tab provides an adhesive layer on a surface of the medical device when the second removable tab is removed from the medical device. The PCB includes the electronic circuitry that performs the functionalities of the medical device, including an optical sensor that comprises at least one light source to emit light towards a measurement site of a user and at least one photodetector to receive light returned from the measurement site. The medical device can connect to a host computing device that performs various operations, including, but not limited to, authenticating the medical device, causing measurement values such as blood oxygen saturation (SpO2), pulse rate (PR), and a perfusion index (PI) to be provided.

20 Claims, 44 Drawing Sheets

Related U.S. Application Data

(60) Provisional application No. 62/629,395, filed on Feb. 12, 2018.

(51) Int. Cl.
    *A61B 5/00*         (2006.01)
    *A61B 5/1455*     (2006.01)
    *G06F 21/45*      (2013.01)
    *A61B 5/024*      (2006.01)
    *A61B 5/026*      (2006.01)

(52) U.S. Cl.
CPC .......... *A61B 5/6814* (2013.01); *A61B 5/6816* (2013.01); *A61B 5/6819* (2013.01); *A61B 5/6822* (2013.01); *A61B 5/6824* (2013.01); *A61B 5/6826* (2013.01); *A61B 5/6833* (2013.01); *A61B 5/742* (2013.01); *G06F 21/45* (2013.01); *H04W 76/14* (2018.02); *A61B 5/0261* (2013.01); *A61B 5/02427* (2013.01); *A61B 5/14551* (2013.01); *A61B 2562/08* (2013.01)

(58) Field of Classification Search
CPC ... A61B 5/6816; A61B 5/6819; A61B 5/6824; A61B 5/6826; A61B 5/6833; A61B 5/742; A61B 5/02427; A61B 5/0261; A61B 5/14551; A61B 2562/08; G06F 21/45
See application file for complete search history.

(56) References Cited

U.S. PATENT DOCUMENTS

| | | |
|---|---|---|
| 3,704,706 A | 12/1972 | Herczfeld et al. |
| 3,847,483 A | 11/1974 | Sidlauskas et al. |
| 4,321,930 A | 3/1982 | Jobsis et al. |
| 4,380,240 A | 4/1983 | Jobsis et al. |
| 4,621,643 A | 11/1986 | New et al. |
| 4,700,708 A | 10/1987 | New et al. |
| 4,770,179 A | 9/1988 | New et al. |
| 4,830,014 A | 5/1989 | Goodman et al. |
| 4,865,038 A | 9/1989 | Rich et al. |
| 4,867,165 A | 9/1989 | Noller et al. |
| 4,907,594 A | 3/1990 | Muz |
| 4,964,408 A | 10/1990 | Hink et al. |
| 5,041,187 A | 8/1991 | Hink et al. |
| 5,090,410 A | 2/1992 | Saper et al. |
| 5,094,240 A | 3/1992 | Muz |
| 5,111,817 A | 5/1992 | Clark et al. |
| 5,125,403 A | 6/1992 | Culp |
| 5,170,786 A | 12/1992 | Thomas et al. |
| 5,209,230 A | 5/1993 | Swedlow et al. |
| 5,217,012 A | 6/1993 | Young et al. |
| 5,246,003 A | 9/1993 | Delonzor |
| 5,249,576 A | 10/1993 | Goldberger et al. |
| 5,337,744 A | 8/1994 | Branigan |
| 5,368,025 A | 11/1994 | Young et al. |
| 5,392,777 A | 2/1995 | Swedlow et al. |
| 5,425,360 A | 6/1995 | Nelson |
| 5,429,129 A | 7/1995 | Lovejoy et al. |
| 5,437,275 A | 8/1995 | Amundsen et al. |
| 5,452,717 A | 9/1995 | Branigan et al. |
| 5,469,845 A | 11/1995 | Delonzor et al. |
| 5,511,554 A | 4/1996 | Helfenbein et al. |
| 5,544,661 A | 8/1996 | Davis et al. |
| 5,590,648 A | 1/1997 | Mitchell et al. |
| 5,645,059 A | 7/1997 | Fein et al. |
| 5,660,567 A | 8/1997 | Nierlich et al. |
| 5,671,529 A | 9/1997 | Nelson |
| 5,673,692 A | 10/1997 | Schulze et al. |
| 5,673,693 A | 10/1997 | Solenberger |
| 5,678,544 A | 10/1997 | Delonzor et al. |
| 5,687,717 A | 11/1997 | Halpern |
| 5,758,644 A | 6/1998 | Diab et al. |
| 5,779,630 A | 7/1998 | Fein et al. |
| 5,782,757 A | 7/1998 | Diab et al. |
| 5,817,008 A | 10/1998 | Rated |
| 5,830,136 A | 11/1998 | Delonzor |
| RE36,000 E | 12/1998 | Swedlow et al. |
| 5,865,736 A | 2/1999 | Baker et al. |
| 5,891,021 A | 4/1999 | Dillon et al. |
| 5,910,108 A | 6/1999 | Solenberger |
| 5,999,834 A | 7/1999 | Wang et al. |
| 6,002,952 A | 12/1999 | Diab |
| 6,006,120 A | 12/1999 | Levin |
| 6,018,673 A | 1/2000 | Chin et al. |
| 6,061,584 A | 5/2000 | Lovejoy et al. |
| 6,119,027 A | 9/2000 | Selenberger |
| 6,144,868 A | 11/2000 | Parker |
| 6,178,343 B1 | 1/2001 | Bindszus et al. |
| 6,215,403 B1 | 4/2001 | Chan et al. |
| 6,253,097 B1 | 6/2001 | Aronow et al. |
| 6,256,523 B1 | 7/2001 | Diab et al. |
| 6,285,492 B1 | 9/2001 | Good |
| 6,343,224 B1 | 1/2002 | Parker |
| 6,374,129 B1 | 4/2002 | Chin et al. |
| 6,377,829 B1 | 4/2002 | Al-All |
| 6,416,471 B1 | 7/2002 | Kumar |
| 6,463,311 B1 | 10/2002 | Diab |
| 6,519,487 B1 | 2/2003 | Parker |
| 6,546,267 B1 | 4/2003 | Sugiura et al. |
| 6,612,984 B1 | 9/2003 | Robert |
| 6,643,530 B2 | 11/2003 | Diab |
| 6,650,917 B2 | 11/2003 | Diab |
| 6,671,531 B2 | 12/2003 | Al-All et al. |
| 6,678,543 B2 | 1/2004 | Diab et al. |
| 6,681,126 B2 | 1/2004 | Solenberger |
| 6,720,734 B2 | 4/2004 | Norris |
| 6,725,075 B2 | 4/2004 | Al-Ali |
| 6,731,962 B1 | 5/2004 | Katarow et al. |
| 6,735,459 B2 | 5/2004 | Parker |
| 6,745,061 B1 | 6/2004 | Hicks et al. |
| 6,748,254 B2 | 6/2004 | O'Neill et al. |
| 6,845,256 B2 | 1/2005 | Chin et al. |
| 6,942,616 B2 | 9/2005 | Robert |
| 7,039,449 B2 | 5/2006 | Al-Ali |
| 7,113,815 B2 | 9/2006 | O'Neill et al. |
| 7,186,966 B2 | 3/2007 | Al-Ali |
| 7,190,985 B2 | 3/2007 | Petersen |
| 7,191,013 B1 | 3/2007 | Miranda |
| 7,206,630 B1 | 4/2007 | Tarler |
| 7,295,866 B2 | 11/2007 | Al-Ali |
| 7,387,607 B2 | 6/2008 | Holt et al. |
| 7,486,977 B2 | 2/2009 | Sweitzer et al. |
| 7,499,739 B2 | 3/2009 | Sweitzer et al. |
| 7,555,327 B2 | 6/2009 | Tang et al. |
| 7,668,588 B2 | 2/2010 | Kovacs |
| RE41,912 E | 11/2010 | Parker |
| 7,904,131 B2 | 3/2011 | Mannheimer et al. |
| 7,957,781 B2 | 6/2011 | Mannheimer et al. |
| 8,018,776 B2 | 9/2011 | Miyake et al. |
| 8,157,730 B2 | 4/2012 | LeBoeuf et al. |
| 8,200,320 B2 | 6/2012 | Kovacs |
| 8,214,007 B2 | 7/2012 | Baker et al. |
| 8,326,392 B2 | 12/2012 | Grubac et al. |
| 8,437,824 B2 | 5/2013 | Moon et al. |
| 8,444,578 B2 | 5/2013 | Bourget et al. |
| 8,457,704 B2 | 6/2013 | Sweitzer et al. |
| 8,668,643 B2 | 3/2014 | Kinast |
| 8,688,187 B2 | 4/2014 | DelloStritto et al. |
| 8,700,009 B2 | 4/2014 | Quy |
| 8,727,977 B2 | 5/2014 | Banet et al. |
| 8,750,954 B2 | 6/2014 | Peterson et al. |
| 8,761,852 B2 | 6/2014 | Parthasarathy et al. |
| 8,764,671 B2 | 7/2014 | Kiani |
| 8,808,188 B2 | 8/2014 | Banet et al. |
| 8,886,271 B2 | 11/2014 | Kiani et al. |
| 8,903,467 B2 | 12/2014 | Sweitzer et al. |
| 8,932,217 B2 | 1/2015 | Gibson et al. |
| 8,965,492 B2 | 2/2015 | Baker et al. |
| 8,983,564 B2 | 3/2015 | Al-All |
| 9,028,405 B2 | 5/2015 | Tran |

(56) References Cited

U.S. PATENT DOCUMENTS

| | | | |
|---|---|---|---|
| 9,039,627 B2 | 5/2015 | Rulkov et al. | |
| 9,042,952 B2 | 5/2015 | Lynn et al. | |
| 9,107,586 B2 | 10/2015 | Tran | |
| 9,155,484 B2 | 10/2015 | Baker et al. | |
| 9,351,688 B2 | 5/2016 | Iyer | |
| 9,711,060 B1 | 7/2017 | Lusted | |
| 10,194,847 B2 | 2/2019 | Al-Ali | |
| 10,194,848 B1 | 2/2019 | Kiani et al. | |
| 10,646,144 B2 | 5/2020 | Lamego | |
| 10,659,963 B1 | 5/2020 | Lamego | |
| 2002/0069885 A1 | 6/2002 | Boies et al. | |
| 2003/0033102 A1 | 2/2003 | Dietiker | |
| 2004/0102687 A1 | 5/2004 | Brashears et al. | |
| 2004/0117204 A1 | 6/2004 | Mazar et al. | |
| 2004/0127775 A1 | 7/2004 | Miyazaki et al. | |
| 2004/0172290 A1 | 9/2004 | Leven | |
| 2004/0242976 A1 | 12/2004 | Abreu | |
| 2004/0260161 A1 | 12/2004 | Melker et al. | |
| 2005/0010087 A1 | 1/2005 | Banet et al. | |
| 2005/0038326 A1 | 2/2005 | Mathur | |
| 2005/0043640 A1 | 2/2005 | Chang | |
| 2005/0070775 A1 | 3/2005 | Chin et al. | |
| 2005/0113655 A1 | 5/2005 | Hull | |
| 2005/0197550 A1 | 6/2005 | Al-All et al. | |
| 2005/0228298 A1 | 10/2005 | Banet et al. | |
| 2005/0228299 A1 | 10/2005 | Banet | |
| 2005/0234317 A1 | 10/2005 | Kiani | |
| 2005/0250998 A1* | 11/2005 | Huiku | A61B 5/14551 600/331 |
| 2006/0224058 A1 | 10/2006 | Mannheimer | |
| 2007/0142717 A1 | 6/2007 | Lowery | |
| 2007/0208233 A1 | 9/2007 | Kovacs | |
| 2009/0326354 A1 | 12/2009 | Mao | |
| 2010/0109966 A1 | 5/2010 | Mateychuk | |
| 2010/0210924 A1 | 8/2010 | Parthasarathy | |
| 2010/0234700 A1 | 9/2010 | Bowers | |
| 2010/0234706 A1 | 9/2010 | Gilland | |
| 2010/0317936 A1 | 12/2010 | Al-Ali | |
| 2010/0331639 A1* | 12/2010 | O'Reilly | A61M 16/024 600/323 |
| 2011/0028811 A1 | 2/2011 | Mazda et al. | |
| 2011/0066043 A1 | 3/2011 | Banet | |
| 2011/0137297 A1 | 6/2011 | Kiani et al. | |
| 2011/0208018 A1 | 8/2011 | Kiani et al. | |
| 2011/0213225 A1 | 9/2011 | Bernstein | |
| 2012/0053433 A1 | 3/2012 | Chamoun | |
| 2012/0315554 A1 | 12/2012 | Christensen | |
| 2013/0046163 A1 | 2/2013 | Sweitzer et al. | |
| 2013/0183646 A1 | 7/2013 | Lusted | |
| 2013/0253334 A1 | 9/2013 | Ammar et al. | |
| 2013/0324855 A1 | 12/2013 | Lisogurski | |
| 2013/0324856 A1 | 12/2013 | Lisogurski | |
| 2014/0134375 A1 | 5/2014 | Guillo | |
| 2014/0200420 A1 | 7/2014 | Al-Ali | |
| 2014/0221772 A1 | 8/2014 | Wolloch | |
| 2014/0275845 A1 | 9/2014 | Eagon | |
| 2014/0288435 A1 | 9/2014 | Richards | |
| 2015/0157263 A1 | 6/2015 | Workman et al. | |
| 2015/0208933 A1 | 7/2015 | Satomi et al. | |
| 2015/0305632 A1 | 10/2015 | Najarian | |
| 2015/0313484 A1 | 11/2015 | Burg | |
| 2016/0015289 A1 | 1/2016 | Simon et al. | |
| 2016/0270740 A1 | 9/2016 | Raisoni | |
| 2016/0310140 A1 | 10/2016 | Belson | |
| 2017/0079586 A1 | 3/2017 | Geva et al. | |
| 2017/0095161 A1* | 4/2017 | Addison | A61B 5/7246 |
| 2017/0143281 A1* | 5/2017 | Olsen | A61B 5/0008 |
| 2017/0367614 A1 | 12/2017 | Zuckerman-Stark | |
| 2018/0064356 A1 | 3/2018 | Mendenhall | |
| 2018/0110450 A1 | 4/2018 | Lamego | |
| 2019/0201623 A1 | 7/2019 | Kiani et al. | |
| 2020/0060555 A1 | 2/2020 | Lamego | |
| 2020/0196928 A1 | 6/2020 | Lamego | |

FOREIGN PATENT DOCUMENTS

| | | |
|---|---|---|
| WO | 03/003914 | 1/2003 |
| WO | 20030031961 | 4/2003 |
| WO | 2017100707 | 6/2017 |

OTHER PUBLICATIONS

Owlet Smart Sock1 / Smart Sock 2, http://www.owletcare.com/smart-sock-2/, Mar. 15, 2017.

Flexzion Fingertip Pulse Oximeter CMS-50DL, https://www.amazon.com/dp/B014SKLRPE, Mar. 15, 2017.

Zaccurate Pro Series Finger Heart Rate Monitor and Blood HbO2 Meter, https://www.amazon.com/Zacurate-Fingertip-Oximeter-Saturation-batteries/dp/B01EK58YXK, Mar. 15, 2017.

Easy@Home Deluxe Fingertip Pulse Oximeter EHP50D1, https://www.amazon.com/Easy-Home-Fingertip-Oximeter-Directions/dp/B00KGP7L38, Mar. 15, 2017.

Areta Fingertip Pulse Oximeter EZD-500A, https://www.amazon.com/Areta-Fingertip-Oximeter-Dual-color-Directions/dp/B00TP1NEGM, Mar. 15, 2017.

Santamedical Generation 2 SM-165 Fingertip Pulse Oximeter, https://www.amazon.com/Santamedical-Generation-SM-165-Fingertip-Saturation/dp/B00R59OTOC, Mar. 15, 2017.

Santamedical Generation 2 OLED Fingertip Pulse Oximeter, https://www.amazon.com/Santamedical-Generation-Fingertip-Saturation-batteries/dp/B018HC7H6C, Mar. 15, 2017.

OxiMed Smart Pulse Advanced Pulse Oximeter, https://www.amazon.com/SmartPulse-Advanced-Finger-Pulse-Oximeter/dp/B01BMUJQLU, Mar. 15, 2017.

Concord Health Supply Fingertip Pulse Oximeter, https://www.concordhealthsupply.com/Concord-Pink-Finger-Pulse-Oximeter-p/cci-300-pink.htm, Mar. 15, 2017.

Careshine OLED Fingertip Pulse Oximeter, https://www.amazon.com/Careshine-approved-Fingertip-Pulse-Oximeter/dp/B016W2V7P6, Mar. 15, 2017.

Acc U Rate 430 DL Premium Fingertip Pulse Oximeter, https://www.arnazon.com/Acc-Rate-Fingertip-Saturation-batteries/dp/B06VWJ4T4T?th=1, Mar. 15, 2017.

AccuMed CMS 50 D1 Fingertip Pulse Oximeter, https://www.amazon.com/AccuMed-CMS-50DL-Oximeter-Aviation-Carrying/dp/B00MNRSWJE, Mar. 15, 2017.

Jumper JPD 500-D Digital Fingertip Pulse Oximeter, https://www.amazon.com/JPD-500D-Approved-Finger-Oximeter-Monitor/dp/B011MVBG5S, Mar. 15, 2017.

Medi-K Fingertip Pulse Oximeter, https://www.amazon.com/Generation-Fingertip-Saturation-Multidirection-Batteries/dp/B01NG\9FJ1, Mar. 15, 2017.

iHealth Air Pulse Oximeter for Apple and Android, https://www.amazon.com/iHealth-Pulse-Oximeter-Apple-Android/dp/B00D7MDXCU, Mar. 15, 2017.

The Kenek Edge iPhone Oximeter, https://www.amazon.com/LGTmedical-Kenek-Edge-Pulse-Oximeter/dp/B00L788XVW, Mar. 15, 2017.

Safe Heart iOximeter, http://safeheartus.com/ioximeter/, Mar. 15, 2017.

Invacare 8610 Digit-Ox2 Fingertip Pulse Oximeter, https://www.cascadehealthcaresolutions.com/digit-ox2-pulse--oximeter-p/ISG8610.htm?vsrefdom=adwords&gclid=Cj0KEOjwuZvl BRD-8Z6B2M2Sy68BEiQAtjYS3A2_loZxh4a8WGpvnzLvkHA72iFuLxvkdwal9bnm0acaAhhu8P8HAQ, Mar. 15, 2017.

Homedics Deluxe Fingertip Pulse Oximeter Reflective, https://www.amazon.com/Homedics-Px-100-Oximeter-Optimetrix-Technology/dp/B00C4VX3OS, Mar. 15, 2017.

MeasuPro Instant Read Digital Fingertip Pulse Oximeter, https://www.amazon.com/MeasuPro-Instant-Digital-Oximeter-Approved/dp/B017COAB2C, Mar. 15, 2017.

Omron 300C20-OTC & NMR Fingertip Pulse Oximeters, http://www.amazon.in/Omron-Choicemmed-Pulse-Oximeter-Yellow/dp/B00SMBL5SK, Mar. 15, 2017.

(56) References Cited

OTHER PUBLICATIONS

Spirodoc Oxi for Sleep Analysis and 6-Minute Walk Test, https://www.spirometry.com/ENG/products/spirodoc_new.asp, Mar. 15, 2017.
MedChoice MD300C318T Fingertip Pulse Oximeter, http://www.pulsoximeter-gerate.com/MD300C318T.asp, Mar. 15, 2017.
American Diagnostic Corporation Advantage 2200 Fingertip Pulse Oximeter, http://adctoday.com/products/2200, Mar. 15, 2017.
American Diagnostic Corporation Diagnostix 2100 Digital Fingertip Pulse Oximeter, http://adctoday.com/products/2100, Mar. 15, 2017.
American Diagnostic Corporation Adimals 2150 Fingertip Pulse Oximeter, http://adctoday.com/products/2150, Mar. 15, 2017.
Edan H10 Fingertip Pulse Oximeter, http://www.edan-instruments.com/enproduct.aspx?NodeID=198&dd=384, Mar. 15, 2017.
Edan H100 N Handheld Pulse Oximeter, http://www.edan.com.cn/detail.aspx?cid=444, Mar. 15, 2017.
Edan H100B Handheld Pulse Oximeter, http://www.edanusa.com/brochures/brochure_3623_a.pdf, Mar. 15, 2017.
Edan M3M3A/M3B Vital Signs Monitor, http://www.edan.com.cn/html/EN/products/patientmonitoring/, Mar. 15, 2017.
SPO Checkmate Fingertip Pulse Oximeter, https://www.turnermedical.com/SPO_CHECKMATE_CM1000_FINGER_PULSE_OXIMETERp/spo_cm1000_checkmate.htm, Mar. 15, 2017.
Devon Medical DT100A Fingertip Pulse Oximeter, https://www.walmart.com/ip/Devon-Medical-Fingertip-Pulse-Oximeter-DTI00-A/35514879, Mar. 15, 2017.
Devon SPO Medical 5500 Fingertip Pulse Oximeter, https://www.turnermedical.com/SPO_MEDICAL_5500_FINGER_PULSE_OXIMETER_p/spo_5500.htm, Mar. 15, 2017.
Devon Medical PC60C Fingertip Pulse Oximeter, http://www.devonsuperstore.com/Fingertip-Pulse-Oximeters-C8.aspx, Mar. 15, 2017.
Devon Medical Handheld Pulse Oximeter DTPC66, http://www.devonsuperstore.com/PC-66-Handheld-Pulse-Oximeter-FDP1-P1pproved-P73.aspx, Mar. 15, 2017.
Choicemmed OxxiWatch C20SM Fingertip Pulse Oximeter, https://www.walmart.com/ip/CHOICEMMED-OxyWatch-C2DSM-Fingertip-Pulse-Oximeter/1 5443473, Mar. 15, 2017.
Choicemmed Oxywatch C18SM Fingertip Pulse Oximeter, https://www.walmart.com/ip/CHOICEMMED-OxyWatch-C18S M-Fingertip-Pulse-Oximeter/15443474, Mar. 15, 2017.
Quest 3-in-1 Fingertip Pulse Oximeter, https://www.amazon.com/Quest-Q1911-3-in-1-Pulse-Oximeter/dp/B004XH55QK, Mar. 15, 2017.
SmartHeart Pulse Oximeter, https://www.walmart.com/ip/SmartHeart-Pulse-Oximeter/20611246, Mar. 15, 2017, Mar. 15, 2017.
NatureSpirit Bluetooth Wireless Fingertip Pulse Oximeter, https://www.walmart.com/ip/NatureSpirit-Bluetooth-Wireless-Fingertip-Pulse-Oximeter/15550443, Mar. 15, 2017, Mar. 15, 2017.
Veridian Premium Fingertip Pulse Oximeter, https://www.walmart.com/ip/Premium-Pulse-Oximeter/20611247?wmlspartner=wlpa&selectedSellerId=1131 &adid=222222222701513534169&wl0=&wl1=g&wl2=c&wl3=40754308112&wl4=pla=78606690752&wl5=9028T73&wl6=&wl7=&wl8=&wl9=pla&wl10=112562428&wl11=online&w112=20611247&wl13=&veh=sem, Mar. 15, 2017.
Medline Easy-Grip Fingertip Pulse Oximeter, https://www.medline.com/product/Fingertip-Pulse-Oximeter/Pulse-Oximetry/Z05-PF54728, Mar. 15, 2017.
Medline PulSTAT Fingertip Pulse Oximeter, https://www.medline.com/product/pulSTAT-Finger-Pulse-Oximeter/Pulse-Oximetry/Z05-PF137460?question=&index=P7&indexCount=7, Mar. 15, 2017.
Medline Soft Touch Fingertip Pulse Oximeter, http://www.medline.com/product/Soft-Touch•-Finger-Pulse-Oximeter/Pulse-Oximetry/Z05-PF91075, Mar. 15, 2017.
Medline Basic Fingertip Pulse Oximeter, http://www.medline.com/product/Basic-Finger-Pulse•-Oximeter/Z05-PF129389, Mar. 15, 2017.
Medline High Impact Fingertip Pulse Oximeter, https://www.medline.com/product/High-Impact-Finger-Pulse-Oximeter/Pulse-Oximetry/Z05-PF04311, Mar. 15, 2017.
Medline Pediatric Fingertip Pulse Oximeter, http://www.medline.com/product/Pediatric-Finger•-Pulse-Oximeter/Z05-PF137459, Mar. 15, 2017.
Medline Handheld Continuous Pulse Oximeter, http://www.medline.com/product/Handheld-Continuous-Pulse-Oximeter/Z05-PF137458, Mar. 15, 2017.
Medline Handheld Spot-Check Pulse Oximeter, http://www.rnedline.com/product/Handheld-Spot-Check-Oximeter/Z05-PF04320, Mar. 15, 2017.
Smiths Medical BCI Digit Fingertip Pulse Oximeter, https://www.smiths-medical.com/products/patient-monitoring/capnographs/finger-pulse-oximiters/digit-finger-oximeter, Mar. 15, 2017.
Smiths Medical BCI Spectro2 10 Handheld Pulse Oximeter, https://www.smiths-medical.com/products/patient-monitoring/pulse-oximeters/oximeters/spectro2-10-pulse-oximeter, Mar. 15, 2017.
Smiths Medical BCI Spectro2 20 Handheld Pulse Oximeter, https://www.smiths-medical.com/products/patient-monitoring/pulse-oximeters/oximeters/spectro2-20-pulse-oximeter, Mar. 15, 2017.
Smiths Medical BCI Spectro2 30 Handheld Pulse Oximeter, https://www.smiths-medical.com/products/patient-monitoring/pulse-oximeters/oximeters/spectro2-30-pulse-oximeter, Mar. 15, 2017.
Smiths Medical BCI AutoCorr Digital Pulse Oximeter, https://www.smiths-medical.com/products/patient-monitoring/pulse-oximeters/bedside-pulse-oximiters/bci-autocorr-digital-pulse-oximeter, Mar. 15, 2017.
Solaris Handheld Capnography/Pulse Oximeter Monitor NT1D, http://www.aedsuperstore.com/solaris-medical-technology-nt1d-capnography-pulse-oximetry-hand-held-monitor.html, Mar. 15, 2017.
Solaris Handheld Pulse Oximeter, http://www.aedsuperstore.com/solaris-mnedicaltechnology-pulse-oximeter-hand-held-alarm-option.html?ctm campaigntype=non-branded&gclid=Cj0KEQjwuZvlBRD-8Z6B2M2Sy68BEiQAtjYS3JuprnjK4ZG4fWprhoUD25PBeurZ8sbl4dZDhPV3JdNQaAiHz8P8HAQ, Mar. 15, 2017.
Solaris NT2A Portable Pulse Oximeter, http://www.solarismedtech.com/solaris_medical_devices/NT2A.html, Mar. 15, 2017.
NT2C Portable Vital Signs Monitor, http://www.solarismedtech.com/solaris_medical_devices/NT2C.html, Mar. 15, 2017.
Nellcor Oximax N-65, http://www.medtronic.com/content/dam/covidien/library/us/en/legacyimport/patientmonitoringrecovery/rms/3/nellcor-oximax-n65-portable-pulse-ox-brochure.pdf, Mar. 15, 2017.
Nellcor Portable SpO2 Patient Monitoring System PM10n (Covidien), http://www.medtronic.com/covidien/products/pulse-oximetry/nellcor-portable-spo2-patient-monitoring-system, Mar. 15, 2017.
Nellcor Bedside Respiratory Patient Monitoring System PM1000N, http://www.medtronic.com/covidien/products/pulse-oximetry/nellcor-bedside-respiratory-patient-monitoring-system-pm1000n, Mar. 15, 2017.
Nellcor Bedside SPO2 Patient Monitoring System PM100N, http://www.medtronic.com/covidien/products/pulse-oximetry/nellcor-bedside-spo2-patient-monitoring-system-pm100n, Mar. 15, 2017.
Nellcor Bedside SPO2 Patient Monitoring System, http://www.medtronic.com/covidien/products/pulse-oximetry/nellcor-bedside-spo2-patient-monitoring-system, Mar. 15, 2017.
Nellcor Oximax N-595, http://pacificmedicalsupply.com/nellcor-n-595-pulse-oximeter/, Mar. 15, 2017.
Nellcor N-395 Pulse Oximeter, http://pacificmedicalsupply.com/nellcor-n-395-pulse-oximeter/, Mar. 15, 2017.
Nellcor Oximax N600X, http://www.medtronic.com/content/dam/covidien/library/us/en/product/pulse-oximetry/N600X_OperatorsManual_EN_10055994A001.pdf, Mar. 15, 2017.
Nellcor N85 Monitor with Oximax Technology & Microstream Capnography, http://www.medtronic.com/covidien/products/pulse-oximetry/nellcor-n85-pulse-oximetry-monitor, Mar. 15, 2017.
Philips A04 SPM (Nellcor/Covidien/Medtronic SpO2 Module Compatible with Philip IntelliVue 68 Monitors), http://www.medtronic.com/covidien/products/pulse-oximetry/phillips-a04-spm, Mar. 15, 2017.
Masimo iSpO2 Pulse Oximeter / Masimo iSpO2 RX, http://www.masirno.co.uk/pulseOximeter/iSpO2Rx.htm, Mar. 15, 2017.
Masimo MightSat Fingertip Pulse Oximeter (3 different models), http://masimopersonalhealth.com/products/mightysat/, Mar. 15, 2017.

(56) References Cited

OTHER PUBLICATIONS

MightSat RX—MightSat RX with Bluetooth LE—MightSat RX with Bluetooth LE & PVI, http://masimopersonalhealth.corn/products/rnightysat/, Mar. 15, 2017.
Masimo Root, http://www.masimo.com/home/root/root-with-noninvasive-blood-pressure-and-temperature-monitoring/, Mar. 15, 2017.
Masimo Radius-7, http://www.masimo.com/home/root/radius7 /, Mar. 15, 2017.
Masimo Radical-7, http://www.masimo.com/home/rainbow-pulse-co-oximetry/rainbow-monitors/radical7/, Mar. 15, 2017.
Masimo Rad-87, http://www.masimo.com/home/rainbow-pulse-co-oximetry/rainbow-monitors/rad87/, Mar. 15, 2017.
Masimo Rad-57, http://www.masimo.com/home/rainbow-pulse-co-oximetry /rainbow-monitors/rad-57/, Mar. 15, 2017.
Masimo Pronto, http://www.masimo.com/home/rainbow-pulse-co-oximetry/rainbow-monitors/pronto/, Mar. 15, 2017.
Masimo Rad-5, http://www.masimo.com/home/signal-extraction-pulse-oximetry/masimo-set-monitors/rad5-rad-5v/, Mar. 15, 2017.
Masimo Rad-5v, https://www.mooremedical.com/index.cfm7/Rad-5v%AE-Pulse-Oximeter/&PG=CTL&CS=HOM&FN=ProductDetail&PID=3 2713&spx=1, Mar. 15, 2017.
Masimo Pronto-7, http://www.masimo.com/home/rainbow-pulse-co-oximetry/rainbow-monitors/pronto7/, Mar. 15, 2017.
Masimo Rad 8, http://www.masimo.com/home/signal-extraction-pulse-oximetry/masimo-set-monitors/rad-8/, Mar. 15, 2017.
Cercacor Ember Noninvasive Hemoglobin Tracker—Ember Sport & Ember Sport Premium, http://www.cercacor.com/ember-models, Mar. 15, 2017.
Nonin Onyx Vantage 9590 Fingertip Pulse Oximeter, http://www.nonin.com/Finger-Pulse-Oximeter/Onyx--Vantage-9590, Mar. 15, 2017.
Nonin GO2 Pulse Oximeter, http://www.nonin.com/Finger-Pulse-Oximeter/Nonin-G02, Mar. 15, 2017.
Nonin GO2 Achieve Pulse Oximeter, http://www.nonin.com/Finger-Pulse-Oximeter/Nonin-GO2, Mar. 15, 2017.
Nonin GO2 Led Achieve Pulse Oximeter, https://www.amazon.com/Nonin-Achieve-Fingertip-Pulse-Oximeter/dp/B002X7Q4RQ, Mar. 15, 2017.
Nonin Model 3230 (Wireless), http://www.nonin.com/OEMSolutions/Nonin_3230_Bluetooth_SMART, Mar. 15, 2017.
Nonin Model 3231 (USB Cable), http://www.nonin.com/OEMSolutions/Nonin_3231_USB, Mar. 15, 2017.
Nonin Onyx II 9560 Wireless Pulse Oximeter for Medical Professionals, http://www.nonin.com/0nyx9560-OEM, Mar. 15, 2017.
Nonin Wrist0X2 3150 Wrist-Worn Pulse Oximeter, http://www.nonin.com/OEMSolutions/Wrist0x23150-OEM, Mar. 15, 2017.
Nonin 8500 Handheld Pulse Oximeter, http://www.nonin.com/ModelB500, Mar. 15, 2017.
Nonin 9840 Series Pulse Oximeter and CO2 Detector, http://wwvw.nonin.com/9840Series, Mar. 15, 2017.
Nonin 9843 Non-alarm, https://www.concordhealthsupply.com/Nonin-9843-Handheld-CO2-Meter-p/non-9843.htm?gclid=Cj0KEQjwuZvlBRD-8Z6B2M2Sy68BEiQAtjYS3G_TCc-[jQpvjchXWbcuo6g_vgGW82QLtPOiZHSM7RScEaAhV58P8HAQ, Mar. 15, 2017.
Nonin 9847 Alarm, https://www.concordhealthsupply.com/Nonin-Handheld-CO2-Monitor-p/non-9847.htm?gclid=Cj 0KEQjwuZvlBRD-8Z6B2M2Sy68BEiQAtjYS3Blmy7QGBD0wGEpqtlskSz3Diu0GL CxhXlg6QYhZkY8aAsbb8P8 HAQ, Mar. 15, 2017.
Nonin PalmSAT 2500 Series, http://www.nonin.corn/PalmSAT2500, Mar. 15, 2017.
Nonin 7500 Tabletop Portable Pulse Oximeter, http://www.nonin.com/Model7500, Mar. 15, 2017.
Nonin 7500 FO (Fiberoptic}, http://www.nonin.com/Model7500FO, Mar. 15, 2017.
Nonin Avant 9600, http://www.nonin.com/Avant9600, Mar. 15, 2017.
Nonin 2120 Tabletop Pulse Oximeter with Noninvasive Blood Pressure, http://www.nonin.com/Avant2120, Mar. 15, 2017.

Nonin Lifesense Capnography &. Pulse Oximeter Monitor, http://www.nonin.com/LifeSense, Mar. 15, 2017.
Nonin SenSrnart Model X 100 Universal Oximetry System, http://www.nonin.com/sensmart, Mar. 15, 2017.
Venni V1-100 A Desktop Pulse Oximeter with Built-In Thermal Printer, https://www.forernostequipment.com/venni-vi-100a-desktop-pulse-oximeter-w-built-in-thermal-printer/, Mar. 15, 2017.
Venni VI-300 A 2 ParrnenterVital Signs Monitor with Printer, https://www.forernostequipment.com/venni-vi-300a-2-pararneter-vital-signs-monitor-w-printer/, Mar. 15, 2017.
Venni VI-200A Vital Sign Monitor, https://www.foremostequipment.com/venni-vi-200a-vital-sign-monitor/, Mar. 15, 2017.
Venni VI 60C Hand Held Color Pulse Oximeter, http://www.medicaldevicedepot.com/Venni-Handheld-Color-Pulse-Oximeter-p/vi-60c.htm, Mar. 15, 2017.
Venni VI-60D Handheld Pulse Oximeter, http://www.medicaldevicedepo.tcom/Venni-Handheid-Color--Pulse•-Oximeter--p/vi-60d.htm, Mar. 15, 2017.
GE/Datex Ohmeda TuffsSAt Handheld Pulse Oximeter, http://pacificmedicalsupply.com/ge-datex-ohmeda-handheld-tuff-sat-pulse-oximeter-small-handheld/, Mar. 15, 2017.
GE Ohmeda True Sat Pulse Oximeter, https://www.turnermedical.com/GE_TRUSAT_3500_PULSE_OXIMETER_p/ge_trusat.htm, Mar. 15, 2017.
GE Datex Ohmeda Tabletop Pulse Oximeter, https://www.dotmed.com/listing/monitor/datex-ohmeda/3800-pulse-oximeter/1756547?utm_source=base&utm_medium=search&utm_campaign=Base&gclid=Cj0KEQjwuZvlBRD-8Z6B2M2Sy68BEiQAt_iYS3FF89flv1qM IM21zifSVf0h21M9Xv-4UQegrnUr-IZa8aAozv8P8HAQ, Mar. 15, 2017.
GE CARESCAPE Monitor B850, http://www3.gehealthcare.com/en/products/categories/patient_monitoring/patient_monitors/carescape_monitor_b850, Mar. 15, 2017.
GE CARESCAPE Monitor B650, http://www3.gehealthcare.com/en/products/categories/patient_monitoring/patient_monitors/carescape_monitor_b650, Mar. 15, 2017.
GE CARESCAPE Monitor B450, http://www3.gehealthcare.com/en/products/categories/patient_monitoring/patient_monitors/carescape_rnonitor_b450, Mar. 15, 2017.
GE CARESCAPE VC 150 Vital Signs Monitor, http://www3.gehealthcare.com/en/products/categories/patient_rnonitoring/patient_monitors/carescape_vc150, Mar. 15, 2017.
GE B40 Patient Monitor, http://www3.gehealthcare.com/en/products/categories/patient_monitoring/patient_monitors/b4-0_patient_monitor, Mar. 15, 2017.
GE CARESCAPE V100 Monitor, http://www3.gehealthcare.com/en/Products/Categories/Patient_Monitoring/Patient_Monitors/CARESCAPE_V100, Mar. 15, 2017.
Nihon Kohden Oxypal OLV-2700/ Oxypal Neo OLV-3100J/K, http://www.nihonkohden.de/uploads/rnedia/OLV-2700_02.pdf, Mar. 15, 2017.
Nihon Kohden Life Scope G3 GZ 130 P, http://www.rnedtronic.corm/covidien/products/oem-monitoring-solutions/oem-partners/nihon-kohden#row-3, Mar. 15, 2017.
Nihon Kohden Life Scope G9 CSM-1901, http://www.medtronic.com/covidien/products/oem-monitoring-solutions/oem-partners/nihon-kohden#row-3, Mar. 15, 2017.
Nihon Kohden Life Scope TR BSM-6000 Series (BSM-6301/6501/6701), http://www.medtronic.eom/covidien/products/oem-monitoring-solutions/oem-partners/nihon-kohden#row--3, Mar. 15, 2017.
Nihon Kohden Life Scope VS BSM-3000 series (BSM--3500/3700), http://vwww.medtronic.com/covidien/products/oem-monitoring-solutions/oem-partners/nihon--kohden#row-3, Mar. 15, 2017.
Nihon Kohden Life Scope PT BSM--1700 series, http://www.medtronic.com/covidien/products/oem-monitoring-solutions/oem-partners/nihon-kohden#row-3, Mar. 15, 2017.
Nihon Kohden Vismo PVM-2703, http://www.medtronic.com/covidien/products/oem-monitoring-solutions/oem-partners/nihon-kohden# row-3, Mar. 15, 2017.
Nihon Kohden Bedside Monitor PVM-2701, http://www.medtronic.com/covidien/products/oem-monitoring-solutions/oern-partners/nihon-kohden#row-3, Mar. 15, 2017.

(56) References Cited

OTHER PUBLICATIONS

Nihon Kohden SVM-7500 series/SVM-7600 series, http://www.mbd-surgical.com/product/Ge_all/Patient_Monitoring/SVM-7600%20Series%20Bedside%20Monitor.pdf Mar. 15, 2017.
Philips InteliiVue MX40, http://www.usa.philips.com/healthcare/product/HC865350/inteliivue-mx40-wearable-patient-monitor, Mar. 15, 2017.
Philips InteliiVue MP40/MPS0/MP60/MP70 Patient Monitor, http://www.philips.ie/healthcare/product/HC862116/intellivue-mp40-and-mp50-bedside-patient-monitors, Mar. 15, 2017.
InteiliVue MX400/MX450/MX500/MX550, http://www.usa.philips.com/healthcare/product/HC866060/intellivue-mx400-patient-monitor, Mar. 15, 2017.
Philips InteiliVue MX600, MX700, http://www.yms.co.za/wp-content/uploads/2015/04/Philips-IntelliView-MX700-Patient-Monitor.pdf, Mar. 15, 2017.
Philips InteiliVue Mx800, Philips InteiliVue Mx800, Mar. 15, 2017.
Philips InteliiVue MP90, http://www.usa.philips.com/healthcare/product/HC862452/intellivue-mp90-bedside-patient-monitor, Mar. 15, 2017.
Philips InteliiVue MP5SC, http://www.usa.philips.com/healthcare/product/HC865322/intellivue-mp5sc-patient-monitor, Mar. 15, 2017.
Philips InteliiVue MMS X2, http://www.usa.philips.com/healthcare/product/HC865039 /intellivue-mms-x2-measurement-module-monitor, Mar. 15, 2017.
Philips InteiliVue MP2, http://www.usa.philips.com/healthcare/product/HC865040/intellivue-mp2-wearable-patient-monitor, Mar. 15, 2017.
Philips InteiliVue MP5, http://www.usa.philips.com/healthcare/product/HC865024/inteliivue-mp5-bedside-patient-monitor, Mar. 15, 2017.
Philips SureSigns VM1, http://www.usa.philips.com/healthcare/product/HCB63264/suresigns-vrn1-vital-signs-monitor, Mar. 15, 2017.
Philips SureSigns VS2+, http://www.usa.philips.com/healthcare/product/HC863278/suresigns-vs2-plus-vital-signs-monitor, Mar. 15, 2017.
Philips SureSigns Vsi, http://www.usa.philips.com/healthcare/product/HCB63275/suresigns-vsi-vital-signs-monitor, Mar. 15, 2017.
Philips Sure Signs VS3, http://www.philips.ie/healthcare/product/HC863069/suresigns-vs3-vital-signs-monitor, Mar. 15, 2017.
Philips SureSigns VS4, http://www.usa.philips.com/healthcare/product/HCB63283/suresigns-vs4-vital-signs-monitor, Mar. 15, 2017.
Philips InteiliVue Cableless Measurement NOTCN 62, http://www.usa.philips.com/healthcare/product/HCNOCTN62/intellivue-cableless-patient-monitoring, Mar. 15, 2017.
Nellcor Flexible SpO2 Reusable Sensors (FLEXMAX/FLEXMAX--P/FLEXMAX--HC/FLEXMAX-PHC), http://www.medtronic.com/covidien/products/pulse-oxirnetry/nllcor--flexible--spo2--reusable-sensor, Mar. 15, 2017.
Nellcor Reusable SpO2 Sensors with OxiMax Technology, http://www.medtronic.com/covidien/products/pulse-oximetry/nellcor-reusable-spo2-sensors, Mar. 15, 2017.
Nellcor Disposable Sensor—Forehead SpO2 Sensor and Headband (Reflectance), http://www.medtronic.com/covidien/products/pulse-oximetry/nellcor-spo2-forehead-sensor, Mar. 15, 2017.
Nellcor Adhesive SpO2 Sensors, http://www.medtronic.com/covidien/products/pulse-oximetry /nellcor-spo2-adhesive-sensors, Mar. 15, 2017.
Nellcor Disposable Sensor—Adult/Neonatal SpO2 sensor, http://www.covidien.com/imageServer.aspx/doc229982.pdf?contentID=30898&contenttype=application/pdf, Mar. 15, 2017.
Nellcor Single Patient Use Two Piece Sensors, http://www.medtronic.com/covidien/products/pulse-oximetry/nellcor-two-piece-spo2-sensors, Mar. 15, 2017.
Masimo Reusable Sensors (LNCS DC-I/LNCS DCI-P/Lncs DCB-I/LNCS TC-I/LNCS TF-I /LNCS Y-I Multisite Sensor), http://www.masimo.com/home/signal-extraction-pulse-oximetry/masimo-set-sensors/lncs-reusable-sensors/, Mar. 15, 2017.
Masimo Disposable Sensors (LNCS Adtx/LNCS Adtx-3/LNCS Inf/LNCS lnf-3/LNCS Inf-L/LNCS Neo/LNCS Neo-3/LNCS Neo-L/LNCS NeoPt/LNCS NeoPt-3/LNCS NeoPt-L/LNCS NeoPt-500/LNCS E1/LNCS TFS-1/M-LNCS E1 Sensor/, http://www.rnasimo.com/horne/signal-extraction-pulse-oximetry/masimo-set-sensors/lncs . . . adhesive-sensors/, Mar. 15, 2017.
Masimo Rainbow ReSposable Sensors (R2-25/R2-20), http://www.masimo.fr/rainbow/rainbow%20Disposable%20and%20ReSposable.htm, Mar. 15, 2017.
Masimo Rainbow Adhesive Sensors (rainbow R1 25/rainbow R1 20/rainbow R1 25L/rainbow R1 20L/rainbow R25/rainbow R20/rainbow R25-L/rainbow R20-L), http://www.masimo.co.uk/rainbow/rainbow%20Disposable%2.0and%20ReSposable.htm, Mar. 15, 2017.
Masimo Respiratory Acoustic Sensor RAS 125c, http://www.masimo.com/home/rainbow-acoustic-monitoring/ras-sensors/, Mar. 15, 2017.
Masimo Pronto-7 Sensors, http://www.medline.com/product/Pronto-7-Rainbow-Sensors-by-Masimo-Corporation/Z05-PF71138, Mar. 15, 2017.
Masimo LNCS Patient Cables (Red LNC M20/Red LNC/Red 25 LNC/Red 25 LNC RA/LNC/LNC Ext/LNC MP4/LNC MPIO/LNC GE/LNC-SL-10/LNC DB9/LNC NK/, http://www.masimo.com/home/signal-extraction-pulse-oximetry/masimo-set-sensors/lncs-patient-cables/, Mar. 15, 2017.
Masimo Adapter Cables (LNCS to RD Adapter Cable/LNCS to PC Adpater Cable/LNC CMS/LNC MAC-GE/LNC MAC-SL/LNC MAC-SL2/LNC MAC-180/LNC MAC-395), http://www.masimo.com/home/signal-extraction-pulse-oximetry/masimo-setsensors/lncs-patient-cables/, Mar. 15, 2017.
Cercacor Ember Sensor, http://technology.cercacor.com/, Mar. 15, 2017.
Nonin 8000 Series Reusable SpO2 Sensors (8000SS/8000SM/8000SL/8000AP/8000AA/8---Q2 1M/8000R/8000R IM), http://www.nonin.com/ReusableSensors, Mar. 15, 2017.
Nonin Disposable Sensors (6000C/6000CA/6000C1/6000CN/6000CO/7000A/70001/7000N/7000P/6500SA/6500MA, http://www.nonin.com/DisposableSensors, Mar. 15, 2017.
Nonin Reusable Flex Sensor and Disposable Wraps. http://www.nonin.com/FlexSensors, Mar. 15, 2017.
Venni Adult Pulse Oximeter Probe for 60C/60D, http://www.susquemicro.com/nav/pages/probe/venni.shtml, Mar. 15, 2017.
Venni Infant/Neonate Pulse Oximeter Probe for 60C/60D, http://www.susquemicro.com/nav/pages/probe/venni.shtml, Mar. 15, 2017.
Venni Pediatric Pulse Oximeter Probe for 60C/60D. http://www.susquemicro.com/nav/pages/probe/venni.shtml, Mar. 15, 2017.
Venni Adult Pulse Oximeter Probe for 200 A, http://www.susquemicro.com/nav/pages/probe/venni.shtml, Mar. 15, 2017.
Venni Pediatric Pulse Oximeter Probe for 200 A, http://www.susquemicro.com/nav/pages/probe/venni.shtml, Mar. 15, 2017.
Venni Extension Cable for 200 A, http://www.susquemicro.com/nav/pages/probe/venni.shtml, Mar. 15, 2017.
Venni Adult Pulse Oximeter Probe for 3510, http://www.susquemicro.com/nav/pages/probe/venni.shtml, Mar. 15, 2017.
Venni Pediatric Pulse Oximeter Probe for 3510, http://www.susquemicro.com/nav/pages/probe/venni.shtml, Mar. 15, 2017.
GE Datex Ohmeda Sensor, http://pacificmedicalsupply.com/ge-datex-ohmeda-oxytip-3-ft-hard-shell-soft-muiti-site-pediatric-infant-or-ear-clip-spo2-sensor/, Mar. 15, 2017.
GE TruSignal Connector, https://www.partsfinder.com/parts/ge-healthcare/TSG3, Mar. 15, 2017.
GE TruSAT Connector, https://ww.mspinc.com/tru-signal-interconnect-cable-trusat-connector, Mar. 15, 2017.
Ohmeda Connector, https://www.google.com/url?sa=t&.rct=j&q&.esrc=s&source=web&cd=1&cad=rja&uact=8&ved=0ahUKEwj0jeXDy8_TAhUhxVQKHQffDl0QFghlMAA&url=http%3A%2F%12Fwww3.gehealthcare.n1%2F~(%2Fmedia%2Fdownloads%J2Fuk%2Fproduct%2Fclinical%2520consumables%;2Ftrusignal.__spu.sensors%2Ftrusignal%2520spo2%2520spec%12520sheet_doc1403853.pdf%3 FParent%3D%257B9F2E8F8D-66B0-4017-9CF1-4328EA62F108%257D&usg=AFQjCNEf7bYyoOeDJ_CiWASR4JK7tj53Q&sig2=GbSA85o10z-MowEfcdA8BQ, Mar. 15, 2017.
Datex Connector, https://www.google.com/url?sa=t&rct=j&q=&esrc=s&source=web&cd=1&cad=rja&uact=8&ved=0ahUKEv\,i0jeXDy8_TAhUhxVQKHQffDl0QFghlMAA&url=http%3A%2F%2Fwww3.gehealthcare.n1%2F•~%2Frnedia%2Fdownloads%12Fuk%2Fproduct%

(56) References Cited

OTHER PUBLICATIONS

2Fclinical%2520consumables%2Ftrusignal_spu_sensors%2Ftrusignal%J2520spo2%2520spec%2520sheet_doc1403853.pdf%3FParent%3D%1257B9F2E8F8D-66B0--4017-9CF1-4328EA62F108%257D&usg==AFQjCNEf7_bYyoOeDJ_CiWASR4]K7tj53Q&sig2=GbSA85ol0z-MowEfcdA8BQ, Mar. 15, 2017.

Philips Sensors (M1131A/M1132A/M1133A/Ml134A), http://www.pacificwestmedical.com/philips-healthcare/philips-medical-supplies/sp02-sensors/philips-m1131a-philips-disposable-adult-ped-spo2-sensors-20-box/, Mar. 15, 2017.

Smiths Medical BCI Sensors, https://www.smiths-medical.com/products/patient-monitoring/patient-monitoring-accessories/oximeter-accessories/disposable-sensors, Mar. 15, 2017.

Solaris Pulse Oximetry Sensors, http://www.solarismedtech.com/spo2.html, Mar. 15, 2017.

Edan Pulse Oximeter Sensors, https://mfimedical.com/products/edan-reusable-spo2-sensor?utm_source=google&ut,_medium=cse&utm_term=19992358147&gclid=Cj0KEQj [vvuZvlBRD-8Z6B2M2Sy68BEiQAtjYS3CHMtuuV97yCJozA0KKdMkq8KU4JPAtNVCelS_bz3oaAshu8P8HAQ, Mar. 15, 2017.

Edan Adult Reusable Sensor, https://mfimedical.com/products/edan-reusable-spo2-sensor?utm_source=google&utm_medium=cse&utrn_term=19992358147 &gclid=Cj 0KEQj wuZvlBRD-8Z6B2M2Sy68BEiQAtjYS3CHMtuuV97yCJozA0KKdMkqBKU4JPAtNVCelSbz3oaAshu8P8HAQ, Mar. 15, 2017.

Edan Pediatric Silicon Soft Tip, https://mfimedical.com/products/edan-reusable-spo2-sensor?utm_source=google&utm_medium=cse&utm_term=19992358147&gclid=Cj0KEQjvvuZvlBRD-8Z6B2M2Sy68BEiQAtjYS3CHMt-uuV97yCJozA0KKdMkq8KU4JPAtNVCe15_bz3oaAshu8P8HAQ, Mar. 15, 2017.

Nihon Kohden Sensors Blue Pro SpO2 Sensors, http://www.nihonkohden.de/products/patient-monitoring/single-parameter-monitors/pulse-oximetry/blupro.html?L=1, Mar. 15, 2017.

European Extended Search Report for European Patent Application No. 16874009.0, dated Apr. 2, 2019, 9 pages.

New, William Jr., "Continuous Non-Invasive Measurement of Arterial Oxygen", Journal of the Japanese Society of Clinical Anesthesia, vol. 6, No. 6, Dec. 1986.

PCT International Preliminary Report on Patentability for PCT International Application No. PCT/US16/66016, dated Jun. 21, 2018, 10 pages.

PCT International Search Report and Written Opinion for PCT International Application No. PCT/US16166016, dated May 18, 2017, 13 pages.

PCT International Search Report and Written Opinion in International Application PCT/US2019/048189, dated Dec. 6, 2019, 17 pages.

U.S. Appl. No. 15/372,341, Amendment and Response filed Oct. 9, 2019, 13 pages.

U.S. Appl. No. 15/372,341, Amendment and Response filed Feb. 28, 2019, 16 pages.

U.S. Appl. No. 15/372,341, Notice of Allowance dated Nov. 7, 2019, 6 pages.

U.S. Appl. No. 15/372,341, Office Action dated Nov. 29, 2018, 18 pages.

U.S. Appl. No. 15/372,341, Office Action dated Jul. 9, 2019, 21 pages.

U.S. Appl. No. 16/274,207, Notice of Allowance (and 892) dated Oct. 3, 2019, 10 pages.

U.S. Appl. No. 16/274,207, Notice of Allowance (and 892) dated Jan. 13, 2020, 9 pages.

U.S. Appl. No. 16/274,207, Notice of Allowance (and 892) dated Feb. 26, 2020, 9 pages.

Severinghaus, J., "in Simple, Accurate Equations for Human Blood O2 Dissociation Computations", J. Appl. Physiol: Respirat. Environ. Exercise Physiol. 46(3):599-602, 1979.

U.S. Appl. No. 16/198,335, Amendment and Response filed Nov. 23, 2020, 15 pages.

Baheti, Pawan K., et al., "An ultra low power pulse oximeter sensor based on compressed sensing", 2009 sixth International workshop on wearable and implantable body sensor networks, IEEE, 2009, pp. 144-1448.

"Baheti, Pawan K., et al., "Blood oxygen estimation from compressively sensed photoplethysmograph", Wireless Health 2010, 2010, pp. 10-14."

Beck, Amir, "On the convergence of alternating minimization for convex programming with applications to iteratively reweighted least squares and decomposition schemes", SIAM Journal on Optimization 25.1 (2015): 28 pgs., pp. 185-209.

Bergström, Per, et al., "Robust registration of point sets using iteratively reweighted least squares", Computational Optimization and Applications 58.3 (2014): 543-561.

Bertsekas, Dimitri P., "Constrained optimization and Lagrange multiplier methods", Academic press, 2014, pp. 1-410, specifically pp. 96-380.

Bissantz, Nicolai, et al., "Convergence analysis of generalized iteratively reweighted least squares algorithms on convex function spaces", SIAM Journal on Optimization 19.4 (2009): 24 pgs., pp. 1828-1845.

Blumensath, Thomas, et al., "Iterative hard thresholding for compressed sensing", Applied and computational harmonic analysis 27.3 (2009): pp. 265-274.

Boyd, Stephen, et al., "Convex optimization", Cambridge University Press, 2004, 730 pages, specifically pp. 127-447, 521-623.

Candes, Emmanuel J., et al., "Enhancing sparsity by reweighted λ 1 minimization", Journal of Fourier analysis and applications 14.5-6 (2008): 877-905.

Choi, Jongyoon, et al., "Development and evaluation of an ambulatory stress monitor based on wearable sensors", IEEE transactions on information technology in biomedicine 16.2 (2011): 279-286.

Coleman, David, et al., "A system of subroutines for iteratively reweighted least squares computations", ACM Transactions on Mathematical Software (TOMS) 6.3 (1980): 327-336.

Daubechies, Ingrid, et al., "Iteratively reweighted least squares minimization for sparse recovery", Communications on Pure and Applied Mathematics: A Journal Issued by the Courant Institute of Mathematical Sciences 63.1 (2010): 1-38.

Dollinger, Michael B., et al., "Influence functions of iteratively reweighted least squares estimators", Journal of the American Statistical Association 86.415 (1991): 709-716.

Donoho, David L., "Compressed sensing", IEEE Transactions on information theory 52.4 (2006): 1289-1306.

Kutyniok, Gitta et al., "Compressed sensing: theory and applications", Cambridge University Press, 2012, pp. 1-22.

"Fan, Audrey P., et al. "Quantitative oxygenation venography from MRI phase", Magnetic resonance in medicine 72.1 (2014): 149-159."

Fornasier, Massimo, et al., "Low-rank matrix recovery via iteratively reweighted least squares minimization", SIAM Journal on Optimization 21.4 (2011): 25 pgs., pp. 1614-1640.

Green, Peter J., "Iteratively reweighted least squares for maximum likelihood estimation, and some robust and resistant alternatives", Journal of the Royal Statistical Society: Series B (Methodological) 46.2 (1984): 44 pgs., specifically pp. 149-170.

Heiberger, Richard M., et al., "Design of an S function for robust regression using iteratively reweighted least squares", Journal of Computational and Graphical Statistics1.3 (1992): 181-196.

Holland, Paul W., et al., "Robust regression using iteratively reweighted least-squares", Communications in Statistics-theory and Methods 6.9 (1977): 813-827.

Webpage: https://en.wikipedia.org/wiki/Iteratively_reweighted_least_squares, last edited Dec. 6, 2020, 7 pages.

Webpage: https://en.wikipedia.org/wiki/Lagrange_multiplier, last edited Jan. 2, 2021, 27 pgs.

Webpage: https://en.wikipedia.org/wiki/Regularization_(mathematics), last edited Dec. 25, 2020, 14 pgs.

Ito, Kazufumi, et al., "A variational approach to sparsity optimization based on Lagrange multiplier theory", Inverse problems 30.1 (2013): 015001, pp. 1-23.

Kim, Seung-Jean, et al., "\ell_1 trend filtering", SIAM review 51.2 (2009): 26 pgs, pp. 339-360.

(56) References Cited

OTHER PUBLICATIONS

Kim, Seung-Jean, et al., "An efficient method for compressed sensing", 2007 IEEE International Conference on Image Processing. vol. 3. IEEE, 2007, 4 pages.

Koh, Kwangmoo, et al., "A Method for Large-Scale l~ 1-Regularized Logistic Regression", AAAI. 2007, 8 pgs.

Koh, Kwangmoo, et al., "An interior-point method for large-scale l1-regularized logistic regression", Journal of Machine learning research Jul. 8, 2007: 1519-1555.

Kumar, Mayank, et al., "Pulsecam: a camera-based, motion-robust and highly sensitive blood perfusion imaging modality", Scientific reports 10.1 (2020): 18 pgs., pp. 1-17.

Lai, Ming-Jun, et al., "Improved iteratively reweighted least squares for unconstrained smoothed \ell_q minimization", SIAM Journal on Numerical Analysis 51.2 (2013): 31 pgs., pp. 927-957.

Lamego, M. M., "Automata control systems", IET Control Theory & Applications 1.1 (2007): 358-371.

Lu, Canyi, et al., "Smoothed low rank and sparse matrix recovery by iteratively reweighted least squares minimization", IEEE Transactions on Image Processing 24.2 (2014): 646-654.

Lustig, Michael, et al., "Compressed sensing MRI", IEEE signal processing magazine 25.2 (2008): 72-82.

Lv, Jinchi, et al., "A unified approach to model selection and sparse recovery using regularized least squares", The Annals of Statistics 37.6A (2009): 3498-3528.

Mbamalu, G. A. N., et al., "Load forecasting via suboptimal seasonal autoregressive models and iteratively reweighted least squares estimation", IEEE Transactions on Power Systems 8.1 (1993): 343-348.

Miosso, Cristiano Jacques, et al., "Compressive sensing reconstruction with prior information by iteratively reweighted least-squares", IEEE Transactions on Signal Processing 57.6 (2009): 2424-2431.

Moço, Andreia, et al., "Pulse oximetry based on photoplethysmography imaging with red and green light", Journal of Clinical Monitoring and Computing (2020): 1-11.

O'Leary, Dianne P., "Robust regression computation using iteratively reweighted least squares", SIAM Journal on Matrix Analysis and Applications 11.3 (1990): 466-480.

Pamula, V. Rajesh, et al. "Computationally-efficient compressive sampling for low-power pulse oximeter system", 2014 IEEE Biomedical Circuits and Systems Conference (BioCAS) Proceedings. IEEE, 2014, 4 pgs.

Pires, Robson C., et al., "Iteratively reweighted least-squares state estimation through givens rotations", IEEE Transactions on Power Systems 14.4 (1999): 1499-1507.

Shah, Pratik, et al., "Inverse scattering using a joint $ L1-L2 $ norm-based regularization", IEEE Transactions on Antennas and Propagation 64.4 (2016): 1373-1384.

Street, James O., et al., "A note on computing robust regression estimates via iteratively reweighted least squares", The American Statistician 42.2 (1988): 152-154.

Tsaig, Yaakov, et al., "Extensions of compressed sensing", Signal processing 86.3 (2006): 549-571.

Wolke, R., et al., "Iteratively reweighted least squares: algorithms, convergence analysis, and numerical comparisons", SIAM journal on scientific and statistical computing 9.5 (1988): 907-921.

Xu, Shizhong, "Iteratively reweighted least squares mapping of quantitative trait loci", Behavior genetics 28.5 (1998): 341-355.

Zanon, Mattia, et al., "Regularised model identification improves accuracy of multisensor systems for noninvasive continuous glucose monitoring in diabetes management", Journal of Applied Mathematics 2013 (2013), 12 pgs.

Zanon, Mattia, "Non-Invasive Continuous Glucose Monitoring: Identification of Models for Multi-Sensor Systems", (2013), 191 pgs.

Zibulevsky, Michael, et al., "L1-L2 optimization in signal and image processing", IEEE Signal Processing Magazine 27.3 (2010): 76-88.

U.S. Appl. No. 16/805,052, Office Action dated Sep. 14, 2020, 13 pages.

U.S. Appl. No. 16/198,550, Office Action dated Sep. 18, 2020, 6 pages.

U.S. Appl. No. 16/198,504, Office Action dated Sep. 3, 2020, 10 pages.

U.S. Appl. No. 16/198,335, Office Action dated Aug. 21, 2020, 10 pages.

Great Britain Exam Report in Application 1811247.4, dated Jul. 26, 2021, 4 pages.

PCT Preliminary Report on Patentability in International Application PCT/US2019/048189, dated Dec. 8, 2020, 16 pages.

U.S. Appl. No. 16/551,437, Office Action dated Dec. 8, 2021, 12 pages.

European Communication in Application 16874009.0, dated Nov. 3, 2021, 6 pages.

Great Britain Exam Report in Application 1811247.4, dated Nov. 4, 2021, 1 page.

\* cited by examiner

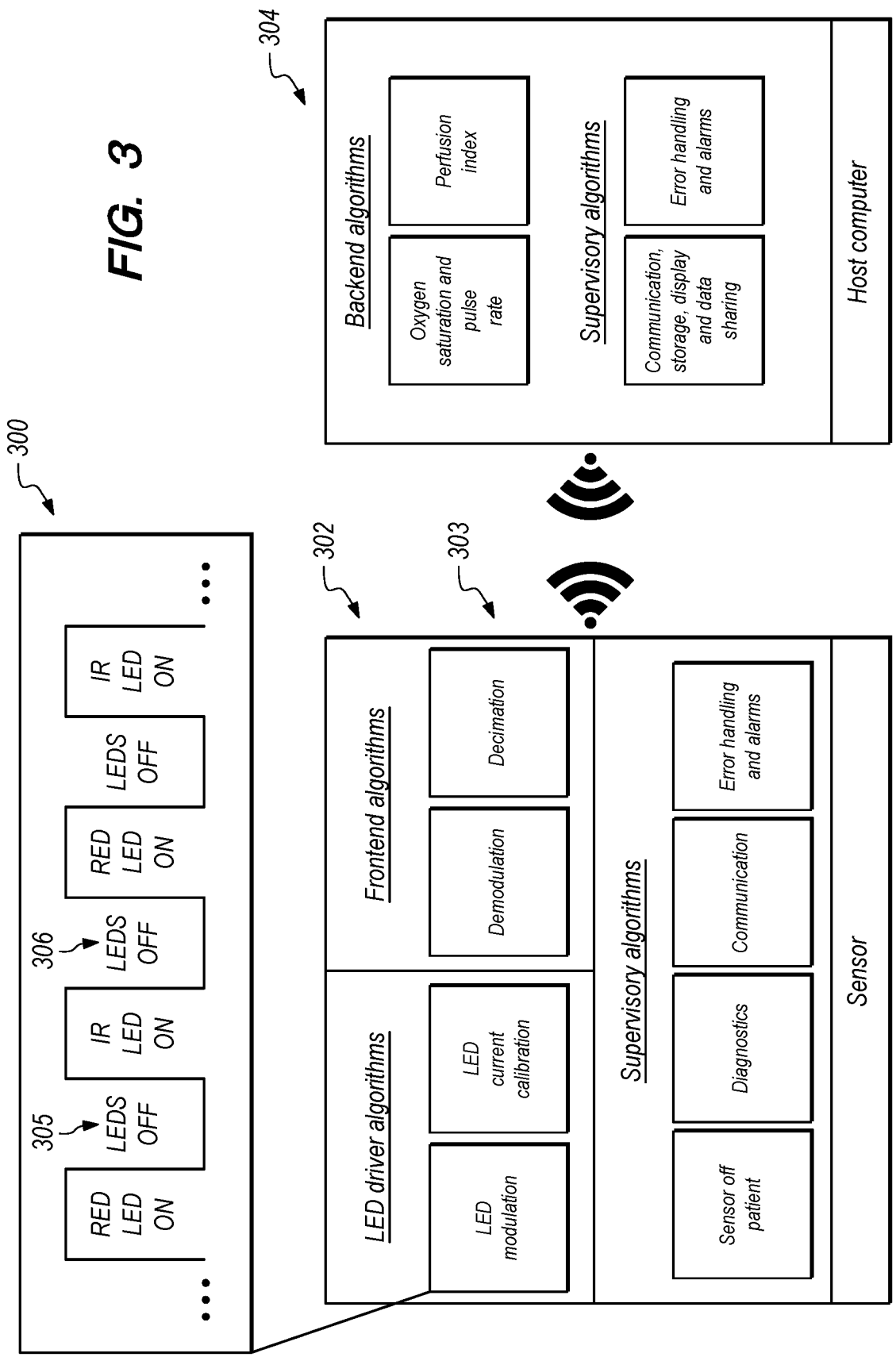

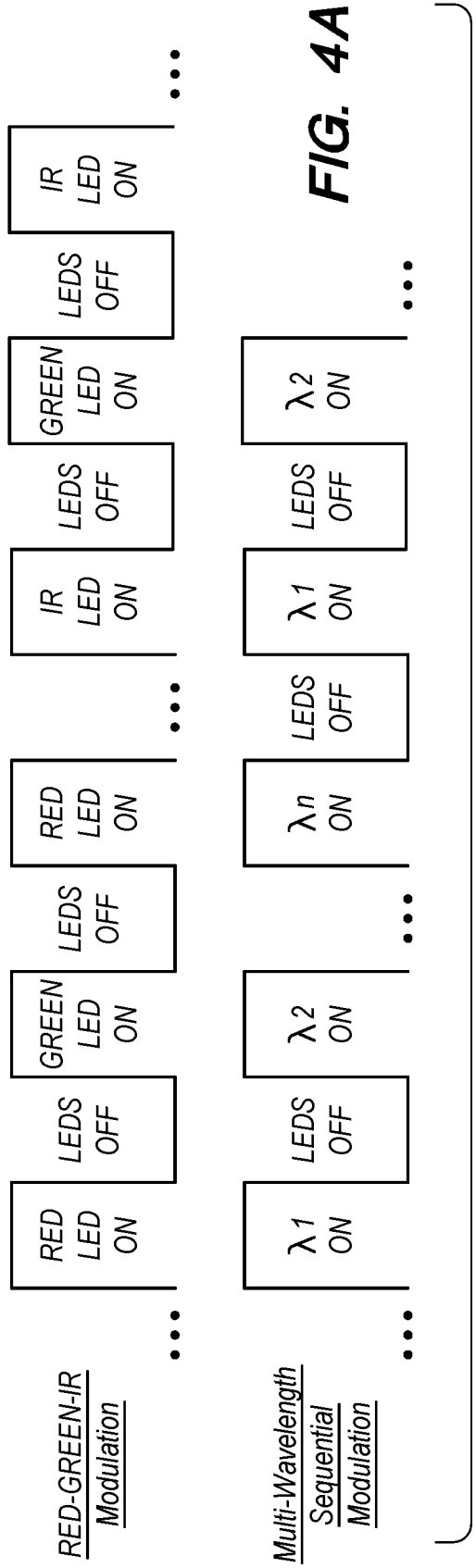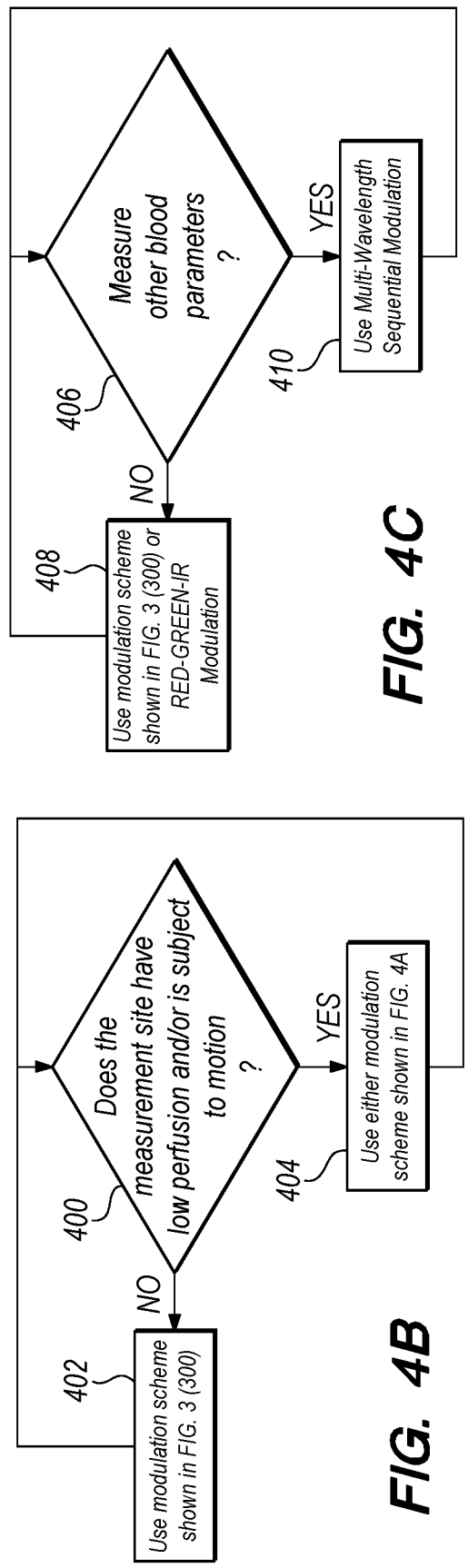
FIG. 4A
FIG. 4B
FIG. 4C

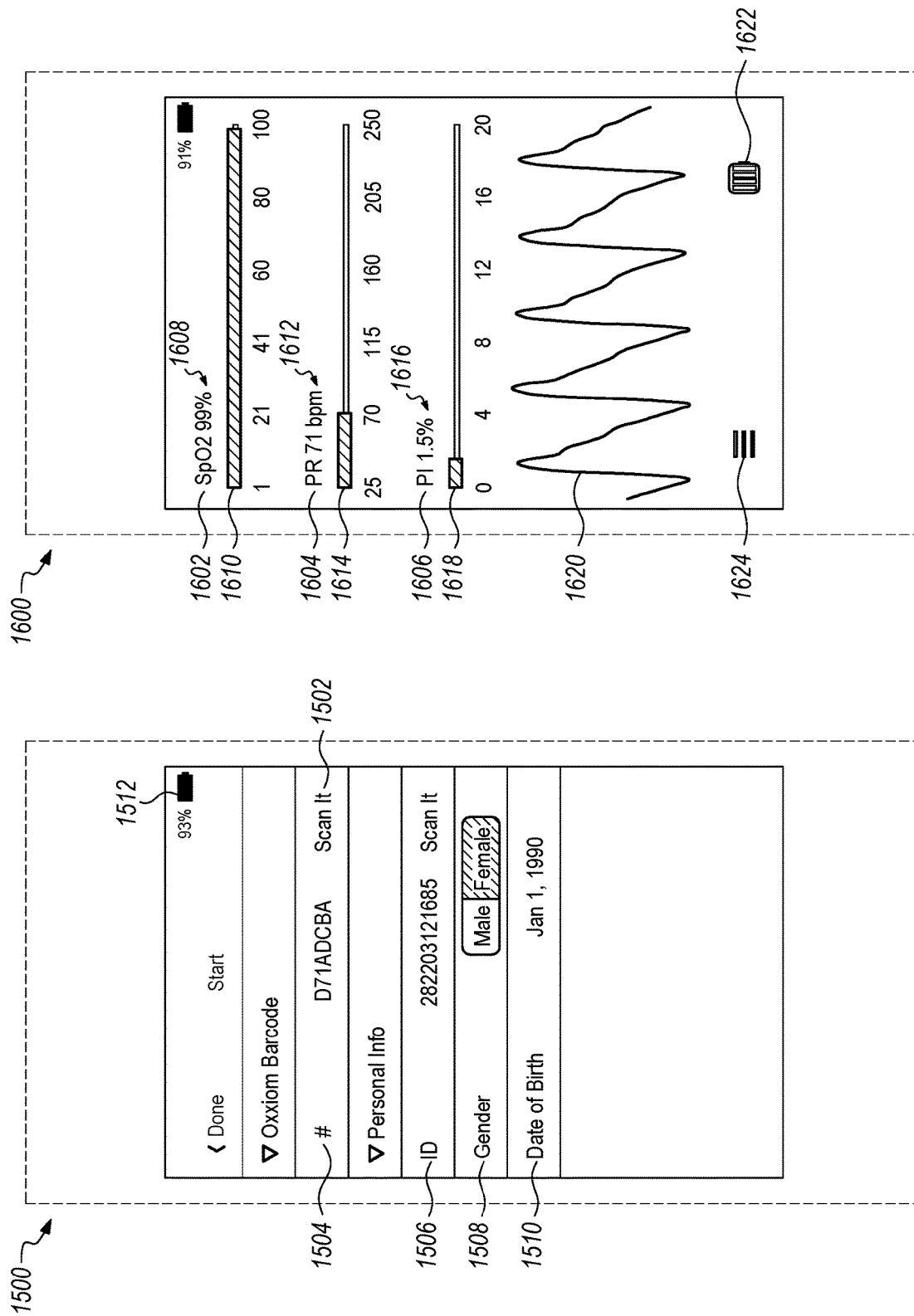

TECHNICAL SPECIFICATIONS

| Features | Specifications |
|---|---|
| | Safety |
| Electrical, EMC, Pulse Oximetry, Biocompatibility | IEC 60601-1, IEC 60601-1-2, ISO 80601-2-61, ISO 0993-5, ISO 10993-10 |
| | Physical |
| Dimensions, Weight | 30 x 17 x 7.5 mm (12 x 0.7 x 0.3 in), 3.5 g (0.12 oz) |
| | Optical Sensor |
| Emitted light energy, Wavelength range | ≤ 15 mW, 500-1,000 nm |
| | Accuracy per ISO 80601-2-61 |
| SpO2 (70-100%) | +/- 3.5% on 68% of the population |
| PR (25-250 BPM) | +/- 3 BPM on 68% of the population |
| | Measurement Range on Host Device |
| SpO2 | 1-100% (SpO2 Out-of-Range Suppression enabled) — 4104 |
| | 1-107% (SpO2 Out-of-Range Suppression disabled) — 4106 |
| PR | 25-250 BPM |
| PI | 0-20% |
| | Alarms on Host Device |
| SpO2, PR | Configurable high and low limits |
| Out of range, Low Battery, Off Patient, Host battery low (warning) | Non configurable |
| | Enviromental |
| Operating temperature, Operating humidity | 5-40°C (41-104°F), 95% RH max. at 40°C (104°F) |
| | Wireless |
| Protocol, Range | Bluetooth Low Energy (BLE), 10 m (33 f) |
| Frequency range, Output power | 2402-2480 MHz, 1mW (conducted) |
| Antenna type, Frequency-hopping spread spectrum technology | Internal, 79 radio frequency channels starting at 2402 MHz and continuing every 1 MHz |
| | Battery |
| Technology, Nominal voltage, Nominal capacity | Non-rechargable lithium/manganese dioxide (LiMnO2), 3 V, 150 mAh |
| Life | 24 h of continuous monitoring |
| | Intended Use |
| Measurement and display of functional oxygen saturation of arterial hemoglobin (SpO2), pulse rate (PR), and perfusion index (PI) of adult and pediatric patients. It is intended for continuous monitoring of patients during non-motion and motion, and under well- or poorly-perfused conditions. Its intended environment of use are hospitals, clinics, doctor's offices, and domestic/residential settings. | |

*FIG. 41*

SINGLE USE MEDICAL DEVICE APPARATUS AND METHODS

CROSS-REFERENCE TO RELATED APPLICATION(S)

This application is a continuation of and claims priority to U.S. application Ser. No. 16/274,207 (now U.S. Pat. No. 10,659,963), filed on Feb. 12, 2019, entitled "Single Use Medical Device Apparatus and Methods", which in turn claims priority to U.S. Provisional Application No. 62/629,395 entitled "Low-Cost Single-Use Medical Device Apparatus and Methods," filed on Feb. 12, 2018, of which the entire disclosure of each is hereby incorporated by reference in its entirety.

BACKGROUND

Pulse oximetry is a technology that enables the non-invasive monitoring of a patient's arterial blood oxygen saturation and other parameters. Medical devices that relate to pulse oximetry are implemented in clinical settings as well as in fitness and wellness applications. For clinical or otherwise "critical" applications, a medical device typically includes complex electronics and signal processing, which can involve relatively high manufacturing costs and power consumption.

In fitness and wellness applications, a reusable medical device is typically used. In some instances, the reusable medical device is a wireless reusable medical device. However, due to the power consumption, weight, size, and ergonomic issues associated with the wireless reusable medical device, the wireless medical device is used for a limited amount of time, such as during breaks that occur throughout an exercise activity. For example, conventional reusable wireless oximeters can be heavy, only present measurement values as integer numbers (e.g., no decimals), cannot display oxygen saturation values above one hundred percent, and may not be designed to be attached to the user during exercise or similar activities. As a result, users typically take breaks during exercise (e.g., stop exercising) to measure their oxygen saturation with a pulse oximeter. The users may also measure their oxygen saturation before and after exercise. However, this process may not be very effective given that the users cannot obtain measurements during exercise. Additionally, the users cannot expand their physiological limits, such as maximum heart rate and improved oxygen saturation, in real-time during exercise.

SUMMARY

In one aspect, a system includes a medical device and a host computing device. The medical device can include a printed circuit board-battery assembly, a tape encapsulation assembly wrapped around the PCB-battery assembly, and a second removable tab positioned on a surface of the tape encapsulation assembly. The second removable tab includes a two-sided adhesive layer that provides an adhesive layer on a surface of the medical device when the second removable tab is removed from the medical device. The printed circuit board includes the electronic circuitry that performs the functionalities of the medical device, including an optical sensor that comprises at least one light source to emit light towards a measurement site of a user and at least one photodetector to receive light returned from the measurement site. The printed circuit board also includes at least one contact pad comprising an ON switch of the medical device. A battery is electrically attached to the printed circuit board. The tape encapsulation assembly includes a sensor window positioned over the optical sensor, and a contact opening extending through a tape encapsulation component for receiving a first removable tab. The first removable tab includes a liner layer portion disposed on a first surface of the tape encapsulation component covering the contact pad or pads on the printed circuit board and a tab portion disposed on an opposite second surface of the tape encapsulation component. The liner layer portion is positioned between the at least one contact pad on the printed circuit board and a conductive tape or conductive contact in the tape encapsulation component. The host computing device executes an Application software program that performs various operations, including authenticating the medical device, causing measurement values such as blood oxygen saturation (SpO2), pulse rate (PR), and a perfusion index (PI) to be provided to an output device (e.g., displayed), and providing various user interfaces views that display one or more measurement values, enable a user to set one or more settings such as upper and lower limits for an alarm, enable sound or audible alarms, and the like, and enable a user to share one or more measurement values or other data.

In another aspect, a method for authenticating a medical device and pairing the medical device includes computing an original credential, such as a hash number, based on data associated with the medical device. The data can include a serial number, a model number, a lot number, an expiration date, a version number, and/or combinations thereof. The credential, along with the data used to compute the credential, are included in an identifier that is included on a label. The label is scanned at a host computing device and the image and the identifier processed to obtain the original credential. An authentication credential is also determined using the data in the identifier. The calculated credential and the original credential are compared with each other. When the calculated credential and the original credential match, a first pairing credential is computed at the host computing device using data in the identifier and stored in a storage device of the medical device. The first pairing credential is transmitted to the medical device. Using the data stored in the storage device, a second pairing credential is computed at the medical device. When the first and the second pairing credentials match, the medical device is paired with the host computing device.

In yet another aspect, a method includes determining whether a "SpO2 Out-of-Range Suppression" setting is disabled. If suppression is enabled, a SpO2 value(s) is determined using a curve or plot that has a maximum SpO2 value of 100%. The SpO2 value or values are provided to an output device (e.g., a display) as an integer number that is equal to or less than 100%. When suppression is disabled, the SpO2 value(s) is determined using a curve or plot that has a maximum value greater than 100%. The SpO2 value(s) is provided to an output device (e.g., a display) and represented with a whole number and one or more decimal place values (e.g., tenths place value, hundredths place value, etc.). Optionally, the upper limit of the SpO2 value for an alarm can be automatically adjusted to a value over 100% (e.g., the maximum value over 100%).

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

Non-limiting and non-exhaustive examples are described with reference to the following Figures. The elements of the drawings are not necessarily to scale relative to each other. Identical reference numerals have been used, where possible, to designate identical features that are common to the figures.

FIG. 3 depicts a distributed system suitable for processing signals produced by a medical device and an example modulation scheme that is suitable for use with a medical device;

FIG. 4A illustrates examples of other modulation schemes that are suitable for use with a medical device;

FIG. 4B is a flowchart of a first method of determining which modulation scheme to use;

FIG. 4C is a flowchart of a second method of determining which modulation scheme to use;

FIGS. 15-19 illustrate example user interface views of the Application software that can be displayed on the host computing device;

FIG. 41 depicts example technical specifications of the medical device when used in combination with a host computing device;

DETAILED DESCRIPTION

As used herein, the term "optimal" is intended to be construed broadly and is intended to cover values and models that provide best, substantially best, and acceptable values and models. As used herein, the term "data stream" refers to data sequentially indexed by an exogenous quantity (e.g., time, space, etc.). For instance, data streams that are function of time, are assumed to be indexed by time such as in a discrete-time system. Data streams that are function of space, are assumed to be indexed by space. Depending on the application, data streams can be indexed by quantities that have physical meaning or that are abstract in nature. The embodiments disclosed herein can be applied to any data stream regardless of its indexing or sampling method.

Reference will now be made in detail to representative embodiments illustrated in the accompanying drawings. It should be understood that the following descriptions are not intended to limit the embodiments to the described example embodiments.

Figure 1:
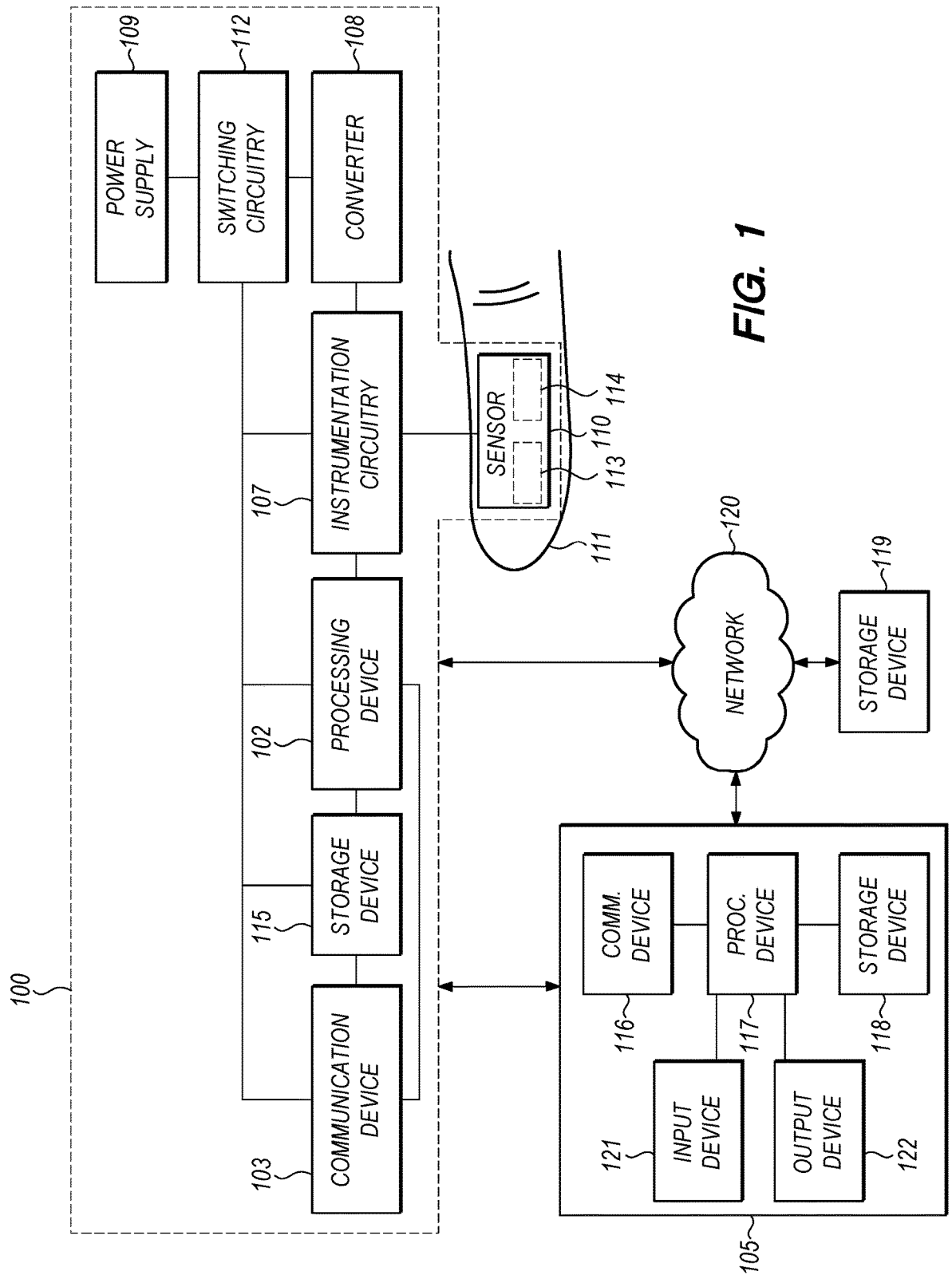
FIG. 1 is a block diagram illustrating an example system.
Figure 2A:
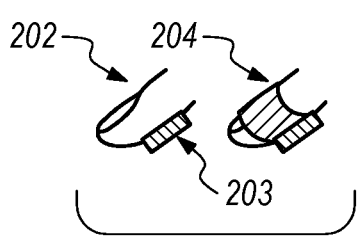
FIGS. 2A-2F and 2M-2O depict example measurement sites on a patient's body where a medical device can be applied.
Figure 2B:
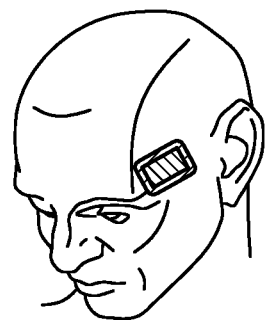
Figure 2C:
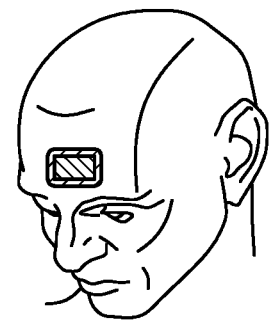
Figure 2D:
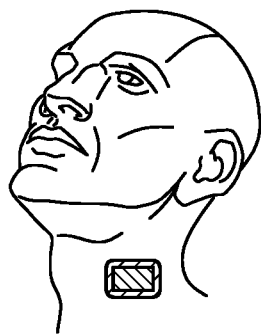
Figure 2E:
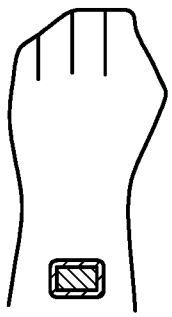
Figure 2F:

FIG. 1 is a block diagram illustrating an example system. A medical device 100 is attached to one or more measurement sites from which the sensor can readily access blood perfusion information. In the illustrated embodiment, the measurement site 111 is a finger or digit (see also FIG. 2A). Other example measurement sites include, but are not limited to, a patient's temple (FIG. 2B), forehead (FIG. 2C), neck (FIG. 2D), arm (FIGS. 2E and 2F), ear or ear lobe (FIG. 2M), nose (FIG. 2N), and/or the posterior auricle of an ear (FIG. 2O).

In one embodiment, the medical device 100 includes a processing device 102, instrumentation circuitry 107, a communication device 103, and a storage device 115. The instrumentation circuitry 107, the communication device 103, and the storage device 115 are connected to the processing device(s) 102. A converter 108 is connected to the instrumentation circuitry 107 and switching circuitry 112. The communication device 103, the storage device 115, the processing device 102, and the instrumentation circuitry 107 along with a power supply 109 are connected to the switching circuitry 112. The medical device 100 may also include adhesive tape to attach the medical device 100 to a measurement site.

The medical device 100 may be turned on using the switching circuitry 112. In one instance, the switching circuitry 112 is a single-use, conductive tape-switch. The instrumentation circuitry 107 may include one or more light sources, such as a light-emitting diode (LED), control circuitry and logic, and one or more photodetectors, such as a photodiode. The communication device 103 can be any suitable type of communication device, including, but not limited to, a wireless low energy radio (examples of which include, but are not limited to, BLE, ANT, Zigbee, etc.). Wireless connection and authentication (when required) between communication devices 116 and 103 can be accomplished through standard pairing methods (i.e., Just Works, etc.) and out-of-band methods, such as Near-Field Communication (NFC), barcode/image scanning, or via an optical link between the optical sensor 110 and camera (or optical sensor) housed in the computing device 105. Depending on the configuration of the medical device 100, the storage device 115 may comprise, but is not limited to, volatile storage (e.g., random access memory), non-volatile storage (e.g., read-only memory), flash memory, or any combination of such memories.

The medical device 100 can be communicatively coupled to a computing device 105, such as a smart phone, a tablet computing device, a desktop or laptop computer, a wireless computing and/or data aggregator appliance device, a bedside monitor, or a similar computing device through a wired or wireless connection. The computing device 105 can include a communication device 116 and a storage device 118 connected to a processing device 117. The medical device 100 transmits, via the communication device 103, measurement data to the computing device 105 (via the communication device 116) to be processed, displayed and/or stored. The measurement data can be used for alarms, for electronic medical record data transfer, for data sharing, and/or for other uses of the data.

The computing device 105 may further include one or more input devices (represented by input device 121) and/or one or more output devices (represented by output device 122). The input and output devices 121, 122 are connected to the processing device 117. The input device 121 can be implemented as any suitable input device, such as a keyboard (physical or virtual), a mouse, a trackball, a microphone (for voice recognition), an image capture device, and/or a touchscreen or touch display, or any other computer-generated perceptual input information. The output device 122 may be implemented as any suitable output device, such as a display, one or more speakers, and/or a printer, or any other computer-generated perceptual output information. In some embodiments, the measurement data or data representative of the measurement data can be provided to the output device 122. For example, the measurement data or data representative of the measurement data may be displayed on a display.

In some embodiments, the computing device 105 and/or the medical device 100 can access an external storage device 119 through one or more networks (represented by network 120) to store and/or retrieve measurement data. In one or more embodiments, the network 120 is illustrative of any suitable type of network, for example, an intranet, and/or a distributed computing network (e.g., the Internet) over which the computing device and/or the medical device 100 may communicate with other computing devices.

As will be described in more detail later, the measurement data produced by the medical device 100 can be processed to determine or estimate one or more physiological parameters (e.g., pulse rate, blood oxygen saturation). As part of the processing, one or more signals are processed with a numerical solver device. The numerical solver device can be implemented with one or more circuits (circuitry), a software algorithm or program executed by one or more processing devices (e.g., processing device 102 and/or processing device 117), or a combination of circuitry and a software algorithm.

For example, in one embodiment, the storage device 115 in the medical device 100 can include a number of software programs or algorithms and data files, including a numerical solver device. While executing on the processing device 102, the numerical solver device may perform and/or cause to be performed processes including, but not limited to, the aspects as described herein. In another embodiment, the storage device 118 in the computing device 105 can include a number of software programs or algorithms and data files, including a numerical solver device. While executing on the processing device 117, the numerical solver device may perform and/or cause to be performed processes including, but not limited to, the aspects as described herein. In yet other embodiments, the operations of the numerical solver device are distributed such that some of the operations are performed by the processing device 102 and some of the operations are performed by the processing device 117.

Figure 2G:
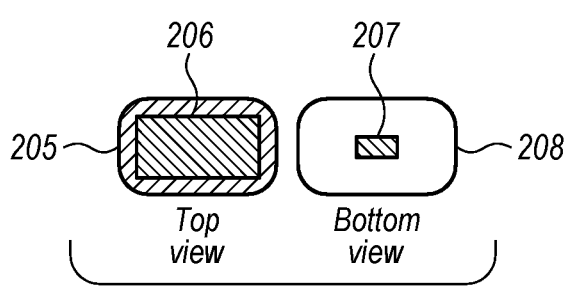
FIGS. 2G-2L illustrate example adhesive tape layouts suitable for use with a medical device.
Figure 2H:
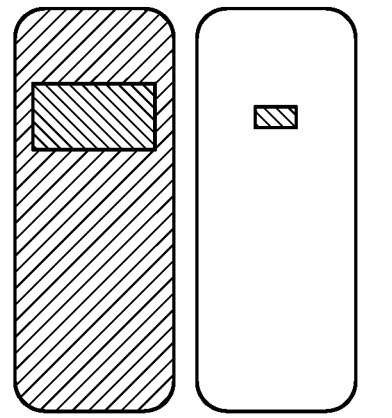
Figure 2I:
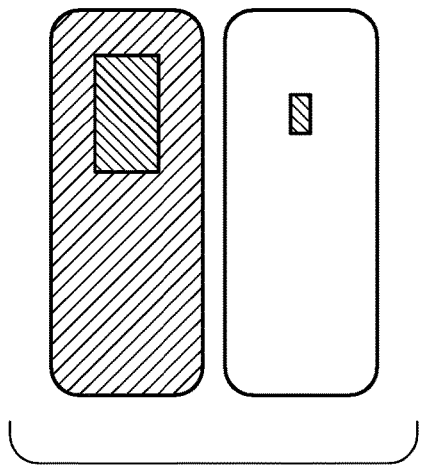
Figure 2M:
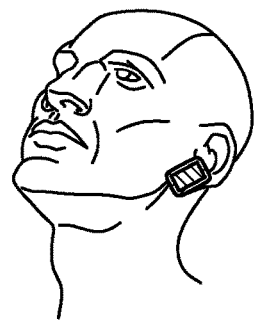
Figure 2J:
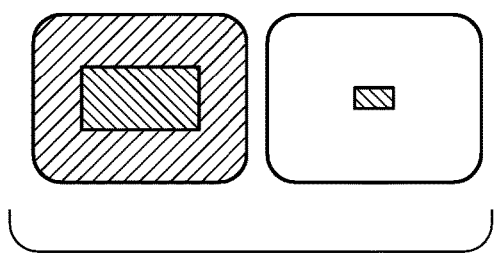
Figure 2K:
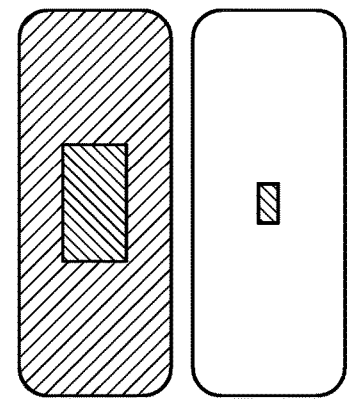
Figure 2L:
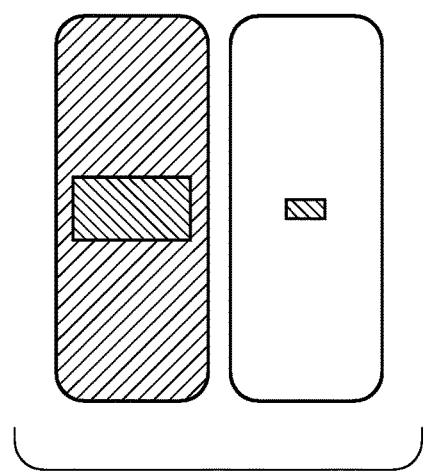
Figures 2N, 2O:
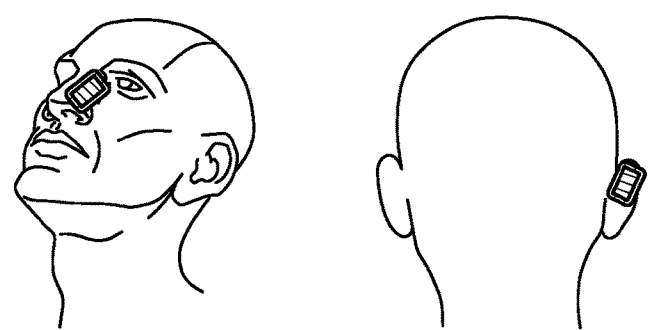

FIGS. 2G-2L illustrate example adhesive tape layouts suitable for use with a medical device. In the figures, each medical device uses a different adhesive tape layout, such as those depicted in FIGS. 2G and 2H, respectively. Specifically, in the illustrated embodiment, a medical device 203 is attached to a patient's fingertip 202 using a flat adhesive bandage 205 encapsulated in a polytetrafluoroethylene (PTFE) pocket or in an origami made out of biocompatible tape 206, as shown in FIG. 2G. An optical sensor 207 on the underside 208 of the medical device 203 may contact the patient's skin when the underside 208 is adhered to the patient's skin. In some of the many alternative embodiments, such as those shown in FIGS. 2H through 2L, an adhesive bandage or tape 204 may be used to attach the medical device 203 to a measurement site.

Small Footprint

Embodiments of the medical device can provide a relatively small footprint (size). Among other aspects, a smaller size can require less material in manufacturing, improved ease of use, less room required for storage, less costs for transport, and a less intrusive device and instrument for patients' increased comfort and mobility when using the medical device. In one embodiment, the medical device 100 may include a printed circuit board (PCB) comprising the processing device 102 with an integrated communication device 103, a compact integrated circuit that includes the instrumentation circuitry 107 for signal conditioning and LED current driving, the power supply 109, and the converter 108. The power supply 109 combined with the converter 108 provide the required higher voltage to drive the light sources 113 and/or a photodetector 114 of the optical sensor 110. In one embodiment, the converter 108 is a single DC-DC switched converter, the power supply 109 is a disposable battery, the light sources 113 are LEDs, and the photodetector 114 is a silicon photodiode.

The processing device 102 and the instrumentation circuitry 107 can be powered directly by the power supply 109.

The optical sensor 110 may be encapsulated with the PCB by any one of a wide variety of suitable apparatus and methods, including (by way of example) by attaching flexible adhesive tapes of various types (optionally combined with PTFE) to the PCB. Persons of ordinary skill in the art will understand that the PCB may be rigid or flexible, or be in the form of a substrate where some or all the components are die attached and wire bonded to the substrate, and encapsulated for protection using epoxy or some other encapsulation material. Further, the optical sensor 110 may be attached to a measurement site 111 using any of a wide variety of suitable apparatus and methods, including (by way of example) by using the adhesive tapes that are part of the optical sensor 110 encapsulation structure (as described herein).

Low Power Consumption

In some aspects, the processing device 102 is a low-power ARM processor with dual functionality for controlling a wireless low energy radio (communication device 103) and instrumentation circuitry 107. The optical sensor 110 can include high efficiency LEDs and at least one silicon photodiode that are arranged in a reflective configuration such that the LEDs and the at least one silicon photodiode are physically separated from each other to minimize the required LED currents and frontend gains in the instrumentation electronics. The instrumentation circuitry 107 may have very low bias currents and operate at low voltages. In one embodiment, ambient light interferences may be avoided or at least reduced by modulating and time-multiplexing the LEDs' currents at a higher frequency to shift the spectral content of the generated and detected optical signals to a range in the spectrum where ambient light interferences are less likely to occur.

FIG. 3 depicts a distributed system suitable for processing signals produced by a medical device and an example modulation scheme that is suitable for use with a medical device. The modulation scheme 300 may reduce the complexity of the demodulation, decimation, LED current calibration, sensor off patient, error handling and alarms, diagnostics, and/or communication algorithms shown in the algorithm block diagram 302. Some or all of the blocks in the algorithm block diagram 302 are included in a medical device 303. The LED driver algorithms, the frontend algorithms, and the supervisory algorithms can each be software programs that are stored in the storage device 115.

In the modulation scheme depicted in FIG. 3, each LED (light source 113) is kept turned on for approximately 25% of the modulation time cycle (LED duty cycle). Smaller LED duty cycles can be used to reduce overall power consumption. The LEDs can be kept turned off for approximately 50% of the modulation time cycle. The intervals where the LEDs are turned off can also be increased if the LED duty cycles are to be reduced and if the modulation frequency is kept the same. The two slots 305, 306 in the waveform represent times when the LEDs are turned off. The two slots 305, 306 can be used to probe and cancel the effects of ambient light. Modulation frequencies as low as 1 KHz can be adopted with signal-to-noise ratio figures similar to medical-grade pulse oximeters in embodiments that perform sophisticated filtering and signal processing in the demodulation scheme to recover the optical signals generated by the interplay of the LEDs optical signals and the attenuation caused by the measurement site's blood perfused tissue.

In some embodiments, a distributed computing architecture may be used to calculate one or more physiological parameters such as blood oxygen saturation (SpO2), a pulse rate (PR), and a perfusion index (PI). For example, the SpO2, PR and PI are estimated on a host computing device 304 (e.g., a mobile phone or laptop) to increase the battery life of the medical device. In one embodiment, one or more numerical solver devices can be included in the backend algorithms of the host computing device 304. For example, a numerical solver device can be included in the oxygen saturation and pulse rate algorithm and in the perfusion index algorithm. In another example, one or more numerical solver devices can be a separate algorithm that is called by the oxygen saturation and pulse rate algorithm and by the perfusion index algorithm.

In other embodiments, one or more numerical solver devices can be included in the medical device 303. For example, one or more numerical solver devices may be implemented in the frontend algorithms, such as, for example, the demodulation algorithm.

A processing device in the medical device 303 (e.g., processing device 102 in FIG. 1) may execute the time critical, high frequency, low latency and low complexity tasks. Data processed by the processing device in the medical device 303 may be reduced in bandwidth by decimation algorithms, and sent wirelessly to the host computing device 304 (e.g., to a processing device). In one embodiment, the host computing device 304 may execute more complex, high latency tasks to calculate and continuously display the measurement values for SpO2, PR and PI.

In an example embodiment, the medical device frontend from Texas Instruments (AFE4403) can be used as the instrumentation circuitry 107 (FIG. 1). In such embodiments, the medical device frontend may be programmed to generate and control directly the required LED modulation scheme without the need for additional resources from the sensor processing device 102.

Other example modulation schemes are shown in FIG. 4A. The RED-GREEN-IR Modulation scheme and/or the Multi-Wavelength Sequential Modulation scheme can be used with measurement sites that have low perfusion and/or subject to excessive motion. FIG. 4B and FIG. 4C depict flowcharts of methods of determining which modulation scheme to use. FIGS. 4B-4C show example scenarios where a particular type of modulation can be advantageous. In the method shown in FIG. 4B, the adopted modulation scheme depends on the aforementioned factors (e.g., low perfusion and/or subject to excessive motion). Initially, as shown in block 400, a determination is made as to whether the measurement site has low perfusion and/or is subject to motion. If not, the process passes to block 402 where the modulation scheme shown in FIG. 3 can be used. When the measurement site has low perfusion and/or is subject to motion, the method continues at block 404 where a RED-GREEN-IR Modulation scheme or a Multi-Wavelength Sequential Modulation scheme may be used.

In the method shown in FIG. 4C, a determination is made at block 406 as to whether one or more measurements of other blood parameters are to be obtained or determined. The blood parameters can include, but are not limited to, glucose, water, and hemoglobin. If one or more measurements of other blood parameters is to be determined, the process passes to block 408 where the modulation scheme shown in FIG. 3 or the RED-GREEN-IR Modulation scheme shown in FIG. 4A can be used. If one or more measurements of other blood parameters will not be determined, the method continues at block 410 where the Multi-Wavelength Modulation scheme may be used.

For the RED-GREEN-IR Modulation scheme shown in FIG. 4A, green and red LEDs are activated and modulated for a period of time according to the on-off pattern described, and then, the red LED (RED) is replaced with the near-infrared LED (IR) and also modulated for a period of time. This sequence of events repeats itself while the measurement site is subject to motion and/or low perfusion levels. When light in the wavelength range between violet and yellow (i.e., between 400 to 590 nm approximately) is applied to a blood-perfused measurement site, the higher light scattering and absorption seen in this region, create photoplethysmographs that are much larger in amplitude when compared to the ones in the red and near-infrared wavelength regions. Typically, the green wavelength is used because LEDs in this range offer good efficiency and reliability as well as lower cost when compared to other wavelengths in the violet-yellow range. Also, the optical properties of blood in the green region are desirable in terms of scattering and absorption levels. The photoplethysmograph associated with the green LED can be used to improve detection of the heart rate and/or the detection of the red and near-infrared true photoplethysmograph amplitudes and waveforms, which are required for an accurate measurement of the blood's oxygen saturation under low-perfusion and motion conditions.

The Multi-Wavelength Sequential Modulation scheme shown in FIG. 4A can be used in some embodiments when the parameters of interest require other wavelengths in addition to the red and near-infrared LEDs. Examples include the non-invasive measurement of other blood constituents (parameters), such as glucose, for diabetes disease management, water, for body hydration management, total hemoglobin, for anemia and/or blood transfusion management, etc. As shown in FIG. 4A, a number of light sources of various centroid wavelengths (i.e., $\lambda 1, \lambda 2, \ldots, \lambda n$ LEDs) are turned on and off sequentially over time. In the case of the non-invasive measurement of glucose, multiple LEDs in the range of 900 nm to 1700 nm can be adopted. In the case of the non-invasive measurement of total hemoglobin and/or water, wavelengths in the range of 600 nm to 1350 nm should be sufficient. The spectral ranges defined are sufficient because blood and bloodless components at the measurement site have spectral features that are typically quite distinctive depending on the wavelength sub-range under consideration. For instance, water and glucose have higher absorption in the 1550 nm to 1700 nm range than the other components, the hemoglobin species have pronounced features in the 600 nm to 1350 nm, fat has in general pronounced scattering properties throughout the whole range when compared to other blood components, and so on and so forth. The modulation schemes shown in FIG. 3 and FIG. 4A can be switched over time depending on the particular application and/or measurement conditions.

In some embodiments, the method shown in FIG. 4C can be used in a multi-parameter medical device that continuously measures SpO2, PR and PI, using the modulation shown in FIG. 3 and/or the RED-GREEN-IR Modulation scheme shown in FIG. 4A. The medical device can perform lower-frequency periodic spot-check measurements of other blood parameters, such as the ones previously mentioned (i.e., glucose, water, etc.) using the Multi-Wavelength Modulation scheme. Such a topology is possible because typically water, glucose, hemoglobin, etc. concentrations in blood vary slower when compared to SpO2, PR and PI. Because typical measurement periodicity for the said parameters is in general much longer (i.e., once every 30 minutes, once an hour, etc.), the increase in the medical device power consumption is not significant. The additional LEDs and photodetector technologies (i.e., silicon and indium gallium arsenide photodiodes for the 600 nm to 1700 nm wavelength measurement range) required represent small incremental cost and negligible increase in sensor footprint.

The Multi-Wavelength Modulation scheme shown in FIG. 4A can also be used to measure SpO2, PR and PI. In this configuration, the red and near-infrared LEDs are combined with other wavelengths to create "n" photoplethysmographs that can be used to improve SpO2 accuracy or motion performance. Accuracy is improved at least in part because additional LEDs throughout the visible and near-infrared range enable estimation algorithms to counter the optical interference effects of other blood and bloodless components not needed in the measurement of oxygen saturation, pulse rate and/or perfusion. Operation under motion is improved because the effects of motion acceleration on the venous and capillary blood creates optical interferences in the measurement site that have distinct morphological features depending on the wavelength range, and hence are more likely to be eliminated from the photoplethysmographs through advanced signal processing such as the numerical solver device described herein.

Persons of ordinary skill in the art will understand that the wavelengths and other measurements and ranges discussed herein are generally intended to be representative of certain embodiments of the inventions, and not as delimiting as to the many ways in which the inventions can be practiced.

As described earlier, a distributed computing architecture may be used to compute SpO2, PR and PI, where SpO2, PR and PI are estimated on a host computing device (e.g., host computing device 304 in FIG. 3 and computing device 105 in FIG. 1) to increase the medical device's battery life. The processing device in the medical device (e.g., processing device 102 in FIG. 1) may execute the time critical, high frequency, low latency and low complexity tasks. Data processed by the processing device in the medical device may be reduced in bandwidth by decimation algorithms, and sent wirelessly to the host computing device. In one embodiment, one or more processing devices in the host computing device (e.g., processing device 117 in the computing device 105) may execute more complex, high latency tasks to calculate and continuously display the measurement values for SpO2, PR and PI.

Figure 5:
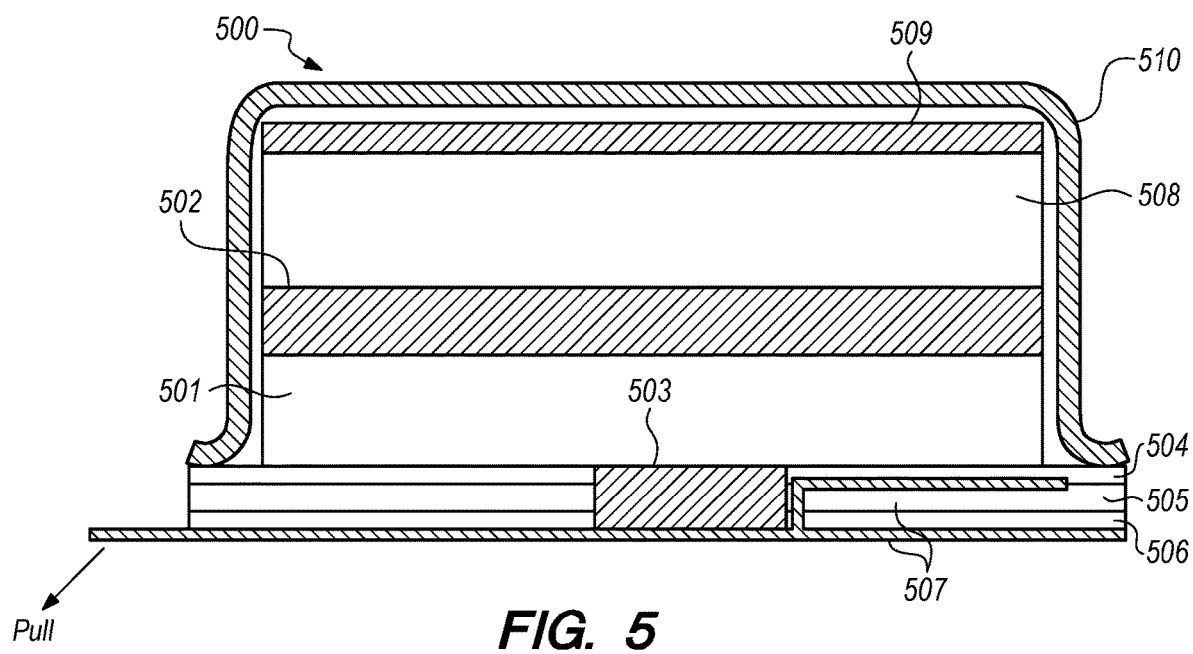
FIG. 5 is a cross-section view of an example medical device.

FIG. 5 is a cross-section view of an example medical device. FIG. 5 depicts one of the many ways of fabricating a stack-up of the various components of a wireless, disposable, continuous medical device 500. A PTFE encapsulation pocket or an origami made out of biocompatible tape 510 may house the components of the medical device 500. From top-down, the medical device 500 may include: an antenna 509, a battery 508, a printed circuit board (PCB) 501 and PCB circuitry 502, and an optical sensor 503. For attachment to a patient's measurement site such as a fingertip, the medical device 500 may include a PCB-to-skin adhesive layer 506. Adhesive layer 505 is made out of electrically conductive tape (such as an isotropically conductive pressure sensitive tape), and adhesive layer 504 contains electrical contacts that (when closed) feed power to PCB 501. A release liner 507 may be disposed between the adhesive layers 504 and 505, and on adhesive layer 506 such that when the release liner is pulled, it exposes the optical sensor 503 and the adhesive layer 506 for attachment to a patient's measurement site, as well as connecting layers 504 and 505, to power on the medical device.

Figure 6A:
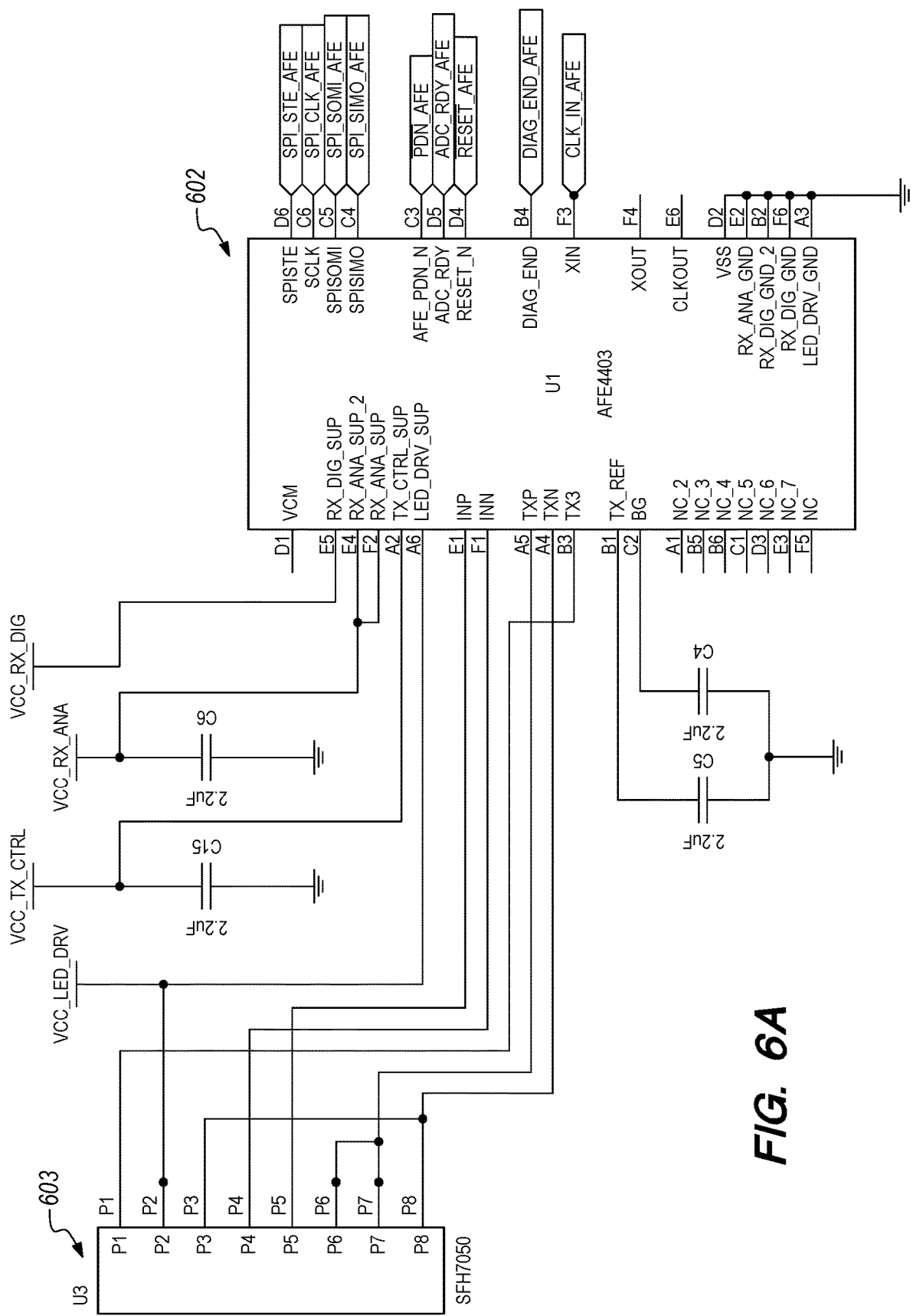
FIG. 6A-6C are schematic diagrams depicting an example medical device.
Figures 1, 6B:
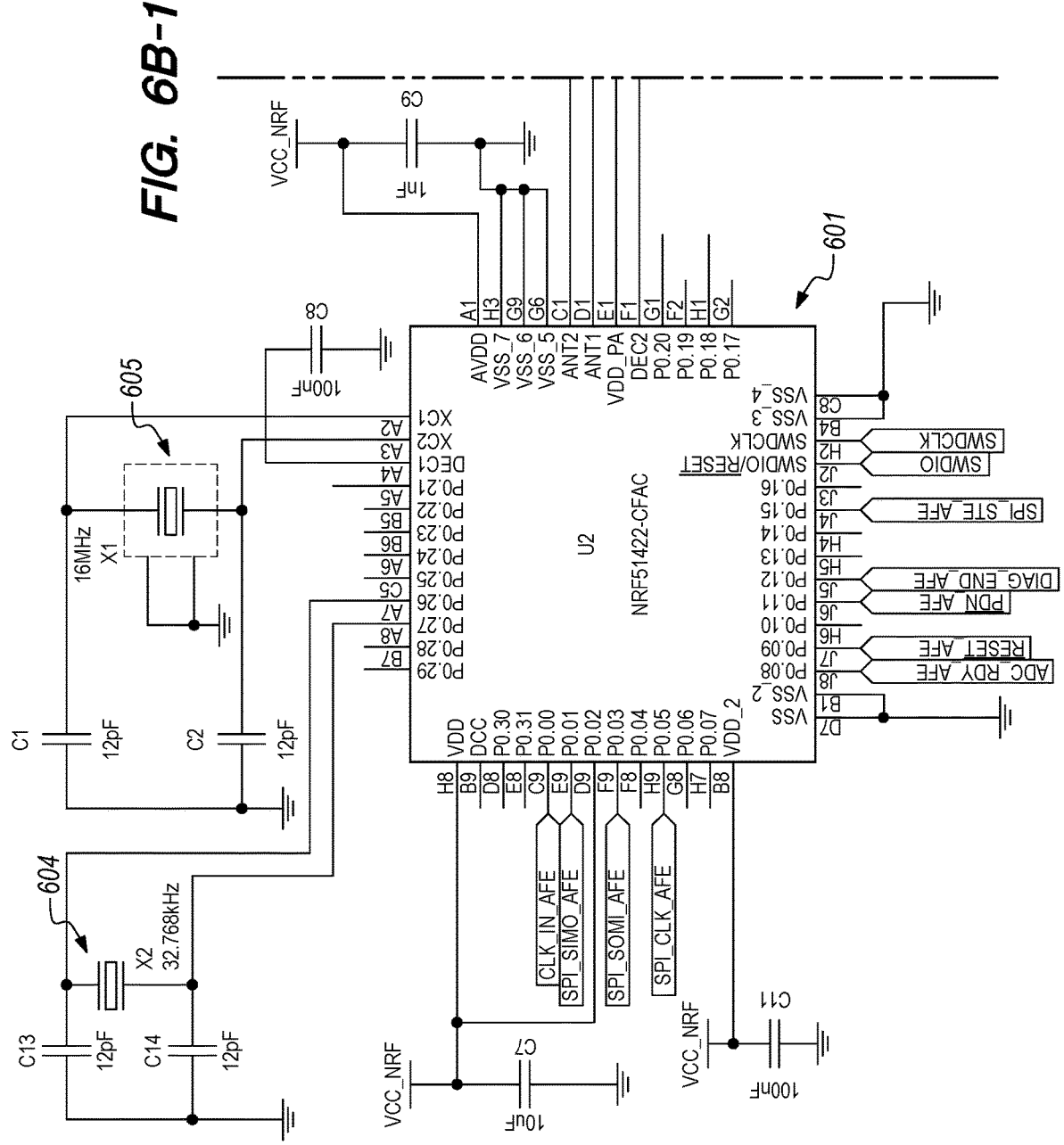
Figures 2, 6B:
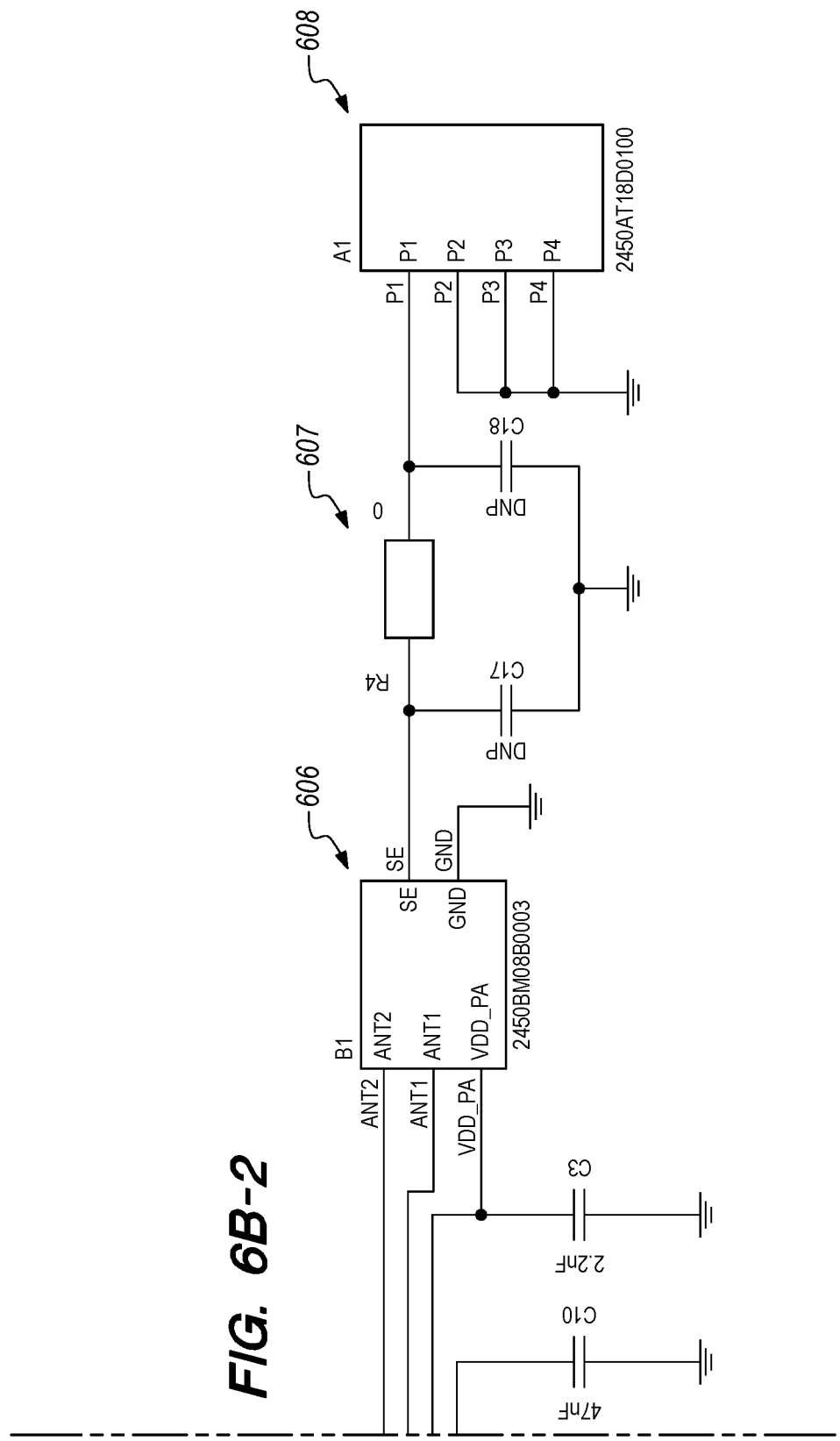
Figure 6C:
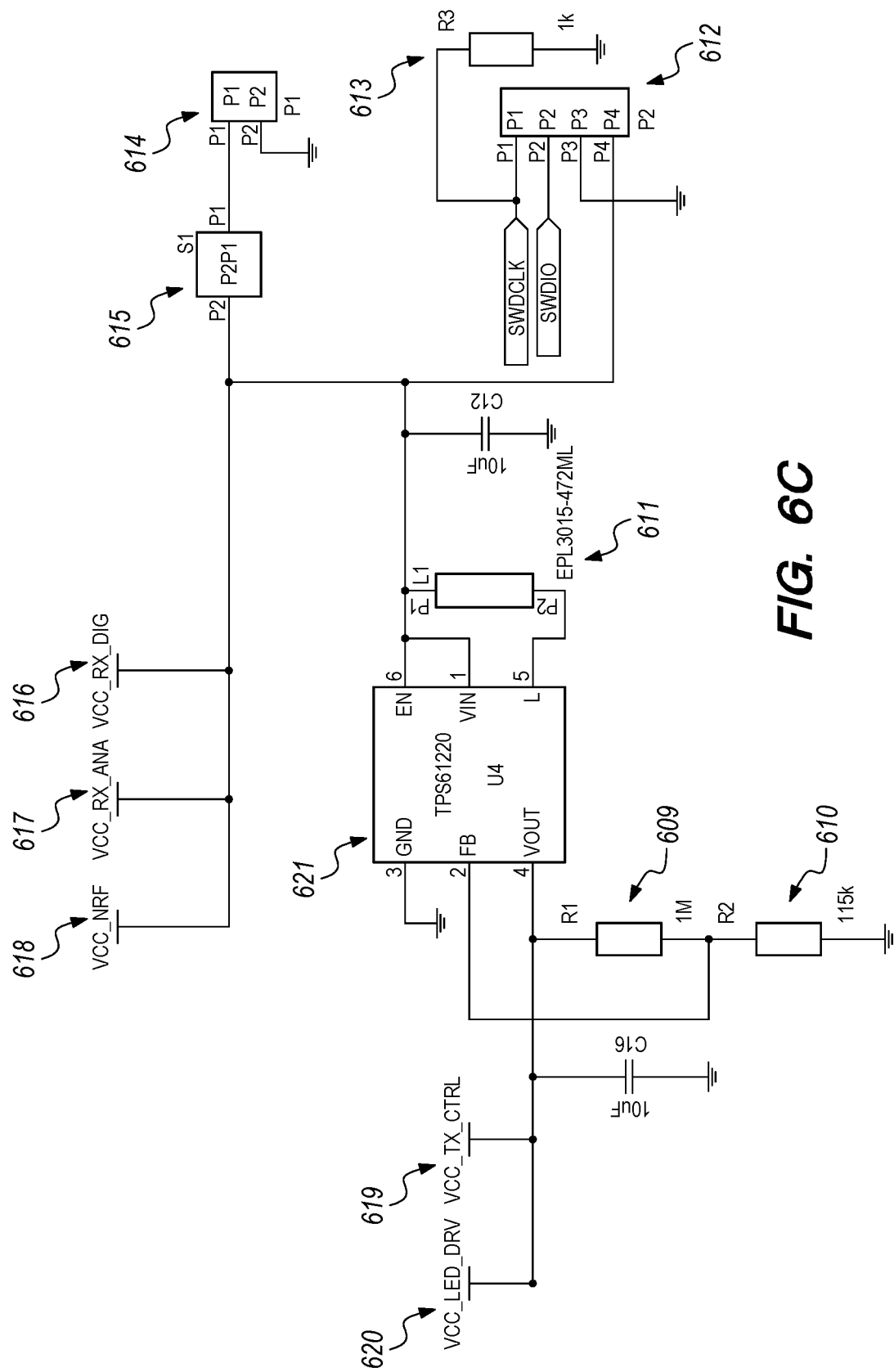

FIGS. 6A-6C are schematic diagrams illustrating an example medical device. The medical device may include an integrated circuit 602 (FIG. 6A) such as the AFE4403 or the AFE4490 circuits by Texas Instruments, including a photodiode frontend, LED drivers, and control logic. An optical sensor 603 (FIG. 6A), such as the SFH7050 sensor by OSRAM, may include green, red, and near-infrared LEDs and a silicon photodiode. The medical device may include a main processing device 601 (FIG. 6B), such as the ARM Cortex M0 processor available from Nordic Semiconductors. Further, the medical device may include a 16 MHz crystal oscillator 605, a 32.768 kHz crystal oscillator 604 (when ANT low-energy radio is used), a 2.45 GHz impedance balloon filter (single to differential) 606, a matching impedance circuit 607, and an antenna 608 (FIG. 6B). A power management circuit of the medical device shown in FIG. 6C may include: a boost converter 621 such as TPS61220 from Texas Instruments, a ferrite inductor 611, boost converter voltage setting resistors 609, 610, debug pads 612 for the main processing device 601, noise rejection pull down resistor 613, battery voltage terminals 614, ON switch pads 615, and voltages 616, 617, 618, 619, 620 for the main processing device 601 (FIG. 6B) and integrated circuits. In one embodiment, the ON switch pads 615 are single use pads.

As should be appreciated, the components depicted in FIGS. 6A-6C, and the corresponding descriptions of FIGS. 6A-6C, are for purposes of illustration only and are not intended to limit embodiments to a particular sequence of steps or a particular combination of hardware or software components.

Figure 7:
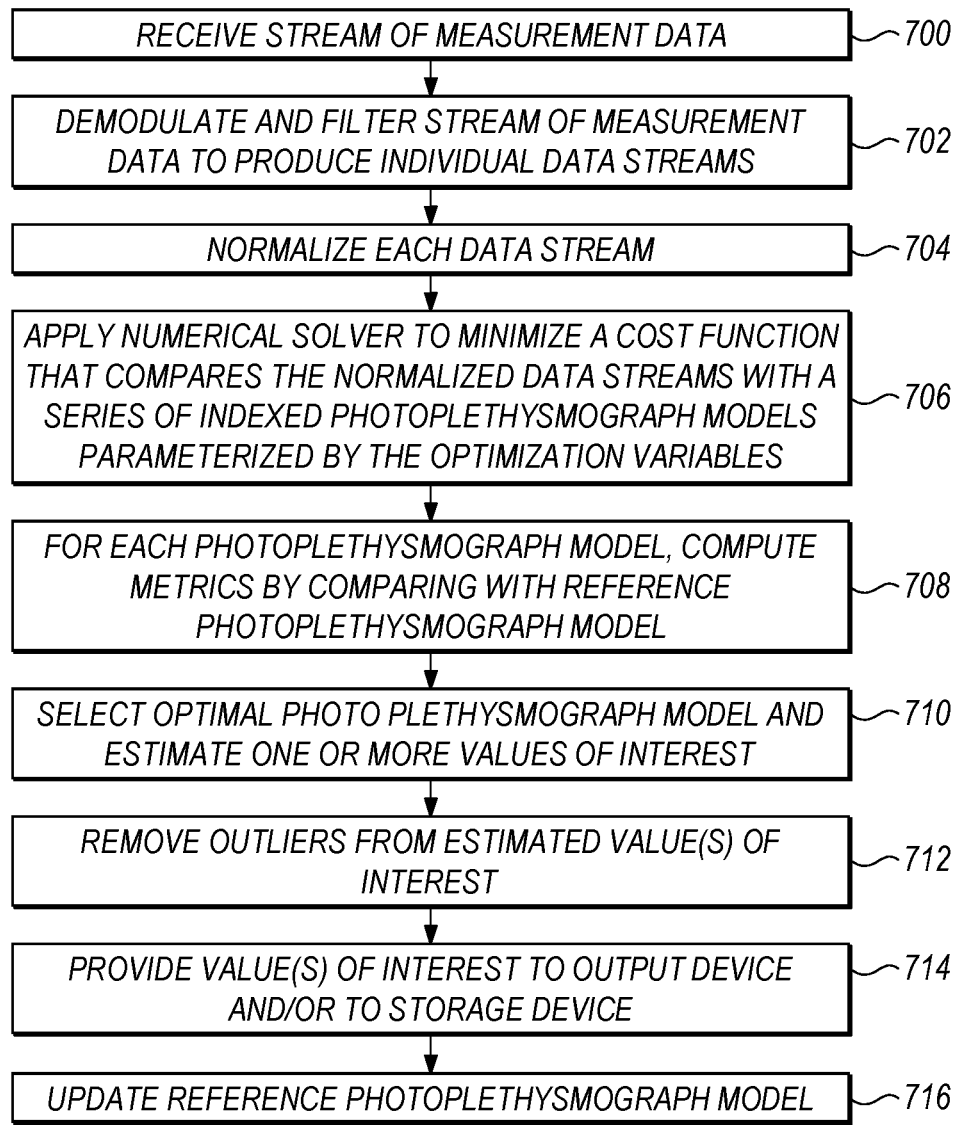
FIG. 7 is a flowchart illustrating an example method of processing measurement data received from a medical device.

FIG. 7 is a flowchart illustrating an example method of processing measurement data received from a medical device. The illustrated method fits measurement data to a model and based on the model, determines one or more physiological parameters (e.g., PR, SpO2, PI). Depending on the application, the method of FIG. 7 is performed once, or the method repeats for a given number of times. For example, with a medical device, the method shown in FIG. 7 can repeat as long as a stream of measurement data is received. In a non-limited example of a medical device, the method of FIG. 7 repeats substantially every 0.75 seconds.

Initially, as shown in block 700, a stream of measurement data is received. In one embodiment, the stream of measurement data is a time-multiplexed and modulated digital stream of measurement data. In a medical device embodiment, the stream of measurement data represents any suitable number of measurement samples that are captured by the medical device at a given sampling frequency (e.g., 4 kHz). In one embodiment, the stream of measurement data is captured continuously by the medical device, although other embodiments are not limited to this implementation.

The stream of measurement data is then demodulated and filtered at block 702 to produce individual data streams for each wavelength channel (e.g., red, infrared, etc.). Any suitable demodulation technique can be used. In a non-limiting example embodiment, a demodulation system can include a multi-channel symmetric square wave demodulator device operably connected to a filter device. The filter device can be implemented as a single stage or a multi-stage filter device. In some embodiments, the demodulator device and/or the filter device perform decimation, where the sampling frequency is reduced to a lower value (e.g., from 4 kHz to 1 kHz, from 1 kHz to 50 Hz) to reduce signal processing requirements, wireless bandwidth, and/or power consumption. Additionally or alternatively, the demodulation system and techniques are capable of removing most or substantially all interference signals within a pre-defined continuous frequency range (i.e., 0 Hz to 800 Hz).

In some aspects, each individual data stream is a photoplethysmograph data stream. At block 704, each individual data stream is normalized. In one embodiment, a log of each data stream is taken and bandpass filtered to produce a photoplethysmograph data stream for each wavelength channel.

Next, at block 706, the photoplethysmograph data streams are processed by a numerical solver device to calculate or estimate optimization variables that minimize a cost function to produce one or more photoplethysmograph models. In one embodiment, the photoplethysmograph data streams are processed in data batches of any size that is suitable for a particular application. For example, with a medical device, the data batch size can be the equivalent of a few seconds of data (e.g., 250 samples collected over 5 seconds) and updated in real-time every certain time interval (e.g., 0.75 seconds).

In one aspect, the numerical solver can compare the data streams with a series of indexed photoplethysmograph models parameterized by the optimization variables. For example, for each Pulse Rate (PR) value, from 25 to 250 BPM in steps of 1 BPM, the numerical solver device calculates values for the optimization variables that minimize a cost function to produce the best photoplethysmograph model for the given data streams. In one non-limiting embodiment, the cost function can be defined by the following equation:

$$J(x, z) = \sum_{i=1}^{n} (z_i A x - b_i)^T (z_i A x - b_i),$$

Equation 1 where $A \in R^{k \times m}$, $k \geq m$, is a constant matrix, $b_i \in R^k = 1, 2, \ldots n$ are constant vectors, $x \in R^m$ and $z = [z_1 \ z_2 \ \ldots \ z_n]^T \in R^n$ are the optimization variable vectors, and the T superscript is the transpose operator.

Each photoplethysmograph model produced based on the numerical solver device and its corresponding PR value is considered a data point (pair). As a result, in this example, the photoplethysmograph models are indexed by the PR values. If the cost function is given by Equation 1, then each photoplethysmograph model is represented by the vector $Ax$ and scaling factors $z_i$, and the photoplethysmograph data streams are represented by the vectors $b_i$. The optimization variables are the vector $x$ and scaling factors $z_i$. Each column in Matrix A provides information regarding the underlying application or phenomenon. In one embodiment, Matrix A is indexed by (function of) the PR values. As a result, the entries in Matrix A change for each PR value, which in turn change the optimal solutions for $x$ and scaling factors $z_i$ that minimize the cost function in Equation 1.

Next, as shown in block 708, the one or more metrics are computed for each photoplethysmograph model indexed by a PR value by comparing the photoplethysmograph models with a reference photoplethysmograph model. The reference photoplethysmograph model represents the best or a selected photoplethysmograph model for a user associated with the measurement data. In one embodiment, the one or more metrics are associated with the photoplethysmograph model. Example metrics include, but are not limited to, root mean square accuracy (Arms), correlation, L2 norm, L1 norm, Linf norm, power, correlation, and harmonic and morphology analysis matching. Because the one or more metrics are calculated from photoplethysmograph models that are indexed by PR values, the one or more metrics are also indexed by the same PR values.

For example, in some embodiments, the one or more computed metrics are compared with corresponding metrics associated with the reference photoplethysmograph model (reference metric(s)) to determine how close or similar the one or more computed metrics are to the corresponding reference metric(s). Additionally or alternatively, the shape of each photoplethysmograph model is compared with a shape of the reference photoplethysmograph model to determine how similar or dissimilar each photoplethysmograph model is to the reference photoplethysmograph model. In some embodiments, metrics such as the root mean square accuracy (Arms), correlation, L2 norm, L1 norm, Linf norm, correlation, and harmonic and morphology analysis matching can be used to access the degree of compliance (shape similarity) between photoplethysmograph model and reference photoplethysmograph model.

At block 710, an optimal photoplethysmograph model is selected or determined for each wavelength channel and one or more values of interest are estimated or computed. The values of interest can include values of interest for physiological parameter such as SpO2, PR, PI, and/or other physiological parameters of interest. The values of interest are computed by applying classification criteria (algorithms) to the computed metrics (i.e., maximum value, minimum value, a ratio of values, linear and non-linear classification algorithms, etc.). For instance, the best estimate for PR, for given red and infrared data streams, may be obtained by picking the PR value that produces the photoplethysmograph model with the largest normalized power, provided that the corresponding photoplethysmograph model Arms error value (when compared to the most current reference photoplethysmograph model) is less than a specified threshold. The best estimate for SpO2 and PI may be calculated via the scaling factors (red and infrared amplitudes) from the photoplethysmograph model that produced the best estimate for PR.

One or more outliers are then removed from the estimated values of interest to produce a subset of values of interest. In some embodiments, average estimates of the values of interest are produced at block 712. Any suitable technique can be used to remove the outliers.

The subset of values of interest are then provided to a storage device (e.g., memory) and/or an output device (block 714). For example, the one or more values of interest can be displayed on a display. Next, as shown in block 716, the reference photoplethysmograph model is updated based on the subset of values of interest and/or the optimal photoplethysmograph model (e.g., the associated optimization variables). In one embodiment, the reference photoplethysmograph model is updated via an update rule that produces a weighted average of the current reference photoplethysmograph model and the optimal photoplethysmograph model.

Figure 8A:
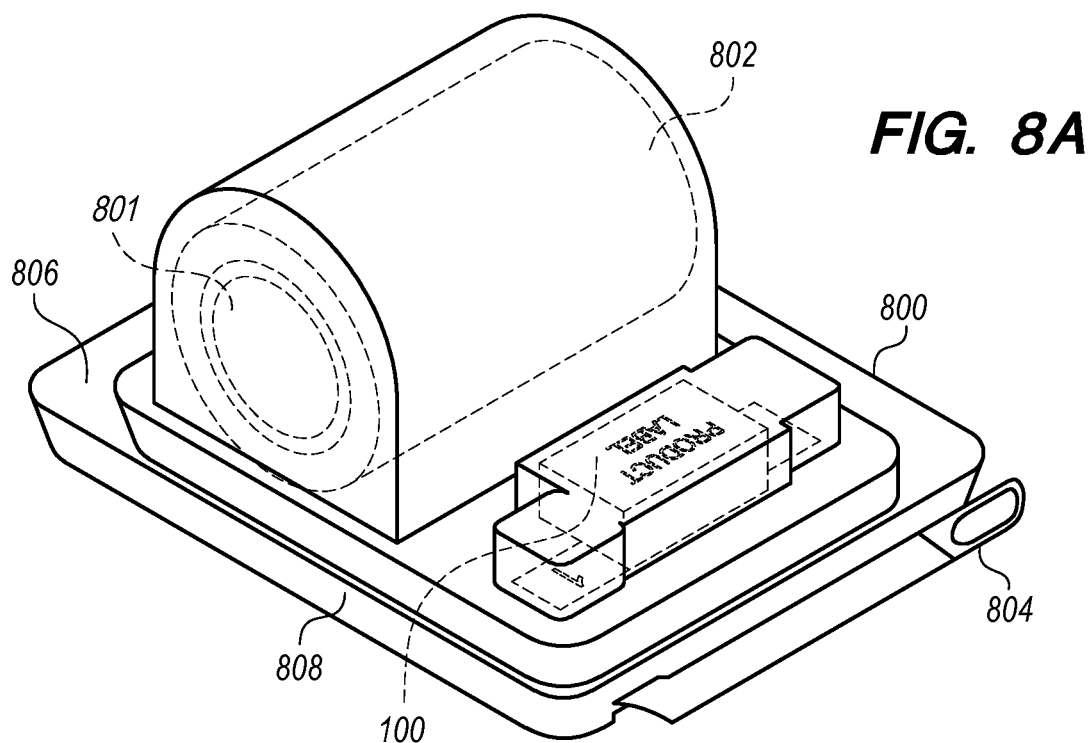
FIG. 8A depicts a perspective top view of a container that includes a disposable medical device.

FIG. 8A depicts a perspective top view of a container that includes a disposable medical device. In some embodiments, the container 800 is used to ship the medical device 100 and/or to sell the medical device 100 to distributors and consumers. Any suitable container 800 can be used. One example of a container 800 is a blister package.

The container 800 includes a roll of a biocompatible tape 802 in addition to the medical device 100. In some embodiments, the container 800, or the area inside the tube or tape roll 801, can store a headband, bandage, or other attachment mechanism that allows the user to wrap or cover the medical device when the medical device is attached to the forehead, ear lobe, nose, neck, or other measurement site.

To open the container 800, a tab 804 can be removed or torn off to enable the top portion 806 of the container 800 to be separated from the bottom portion 808 of the container 800. The medical device 100 and the biocompatible tape 802 can then be removed from the container 800.

Figure 8B:
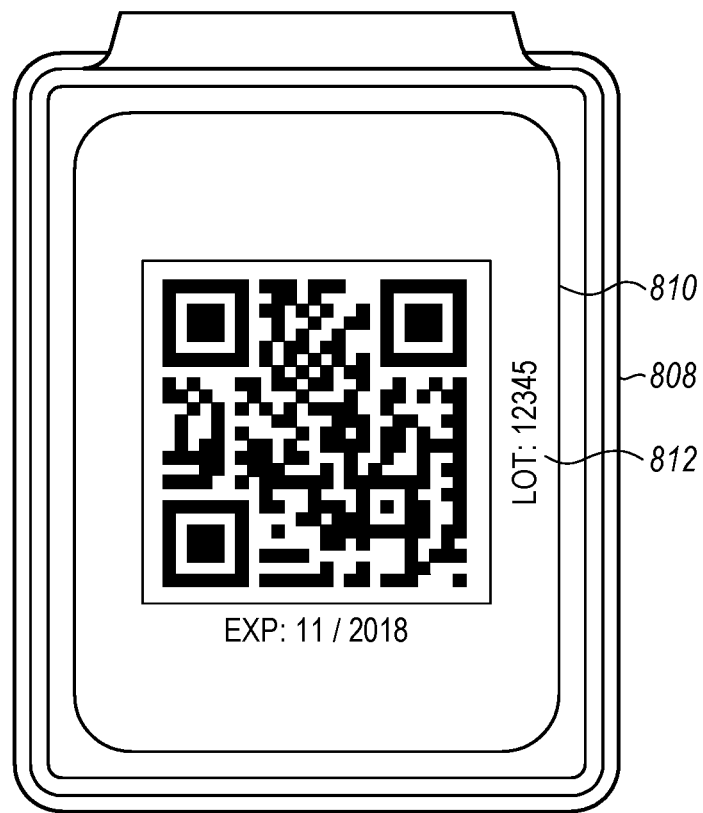
FIG. 8B illustrates a bottom view of the container.

FIG. 8B illustrates a bottom view of the container. A label 810 can be affixed to the bottom portion 808 of the container 800. For example, the label 810 can be attached to a bottom lid of the container 800. In another embodiment, the label 810 may be included in the container 800 but not affixed to the container 800 such that the label 810 is removable from the container 800. In the illustrated embodiment, the label 810 is positioned such that the label 810, or at least an identifier 812, is visible through the bottom portion 808 of the container.

Figure 9:
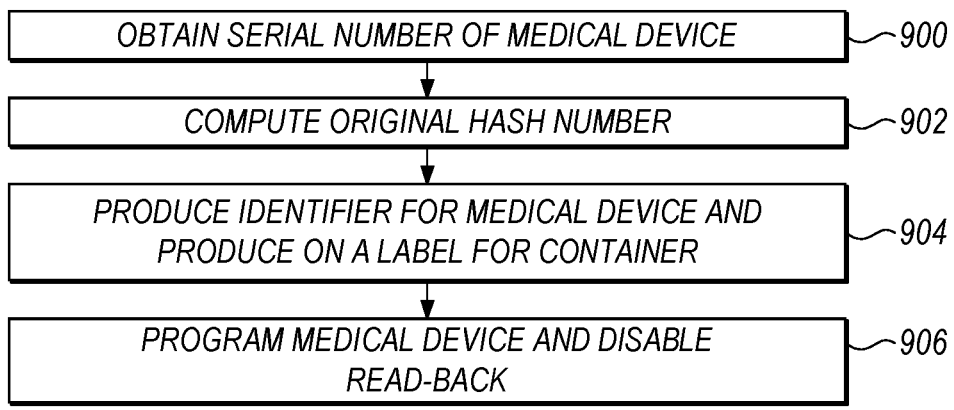
FIG. 9 is a flowchart depicting an example method of generating an identifier for a medical device.

The identifier 812 can be used to authenticate the medical device 100 to enable the medical device 100 to pair with a host computing device. FIG. 9 is a flowchart depicting an example method of generating an identifier for a medical device. In some instances, the method of FIG. 9 is performed at a manufacturing site of the medical device or at a packaging site where the medical device is packaged in the container (e.g., container 800 in FIG. 8A).

Initially, as shown in block 900, the serial number of the medical device is obtained. In one embodiment, the serial number is a non-erasable serial number that is stored in a storage device (e.g., storage device 115 in FIG. 1) in the medical device. The serial number is read out of the storage device and a credential is computed based on the serial number (block 902). A non-limiting example of a credential is a hash number.

In some embodiments, different or additional data can be used to compute the credential. For example, in a non-limiting embodiment, the credential (e.g., hash number) can be based on the serial number of the medical device, a lot number of the medical device, a version number of the medical device, a model number of the medical device, an expiration date of the medical device, or various combinations of the serial number, lot number, version number, and model number. In other embodiments, the credential can be computed using other data associated with the medical device 100.

Any suitable process or function can be used to compute the credential. For example, when the credential is a hash number, the algorithm that is used to compute the hash number may be a non-standard and customized algorithm for computing the hash number. Since the hash number is based on data associated with the medical device itself (e.g., the serial number, an expiration date, etc.), the hash number uniquely identifies the medical device.

Next, as shown in block 904, an identifier is generated for the medical device 100 and produced on a label for the container. Any suitable identifier can be used. In one embodiment, the identifier is a bar code that includes at least the hash number and the corresponding data required to compute the said hash number. In some embodiments, the identifier can include additional data, such as the serial number of the medical device, the version number of the medical device, the model number of the medical device, the expiration date of the medical device, or combinations thereof.

After an identifier is generated for the medical device 100, software code or firmware is stored in a storage device 115 in the medical device 100 at block 906 to enable the medical device to function once it is activated by the user. After the software or firmware code is programmed (stored) into the medical device 100, a read-back protection is activated in the storage device 115 or processing device 102 to prevent users and unauthorized persons or systems from accessing the software code or firmware (block 906).

Figure 10:
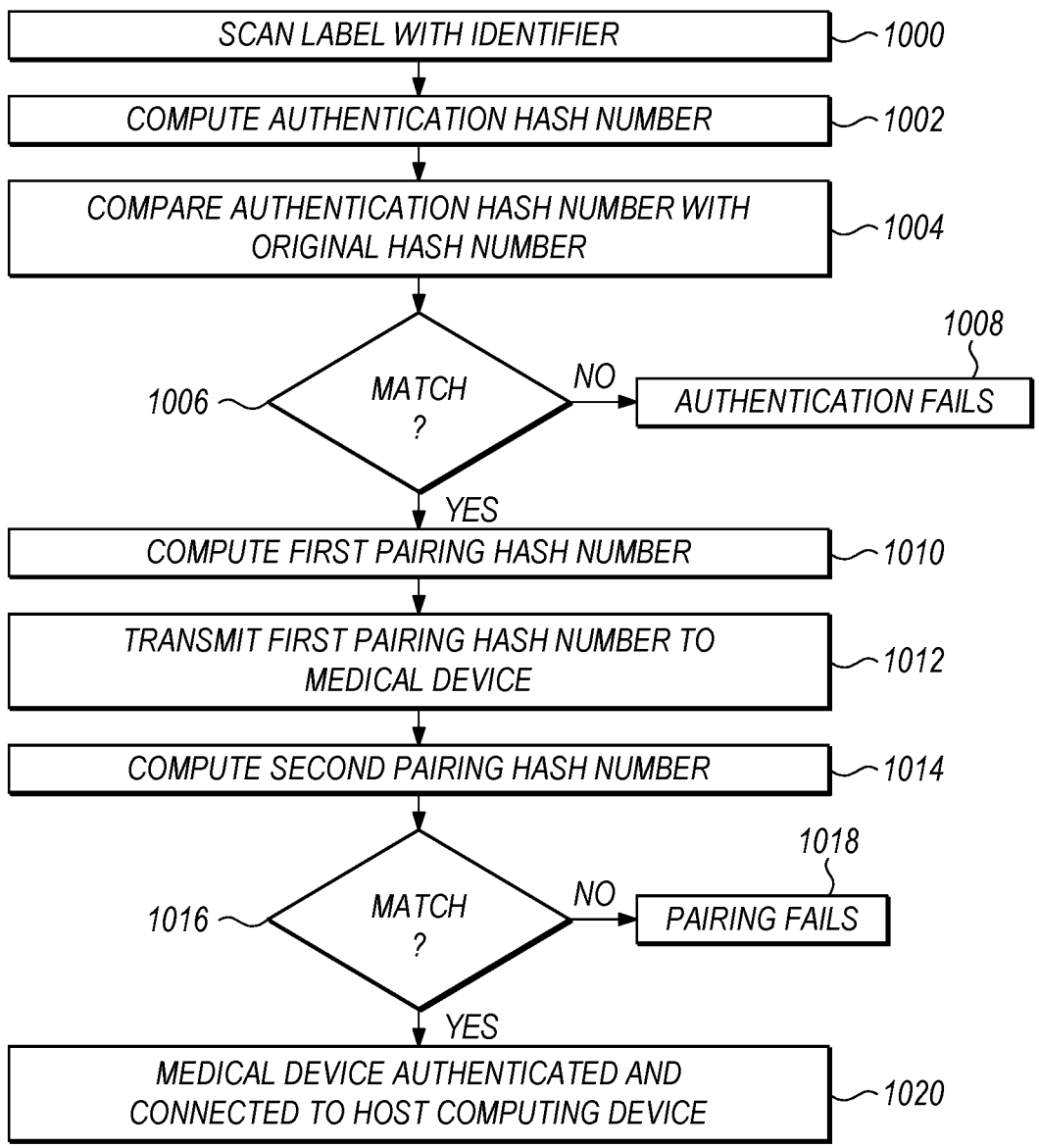
FIG. 10 is a flowchart illustrating an example method of authenticating a medical device using the identifier produced in FIG. 9.
Figure 11A:
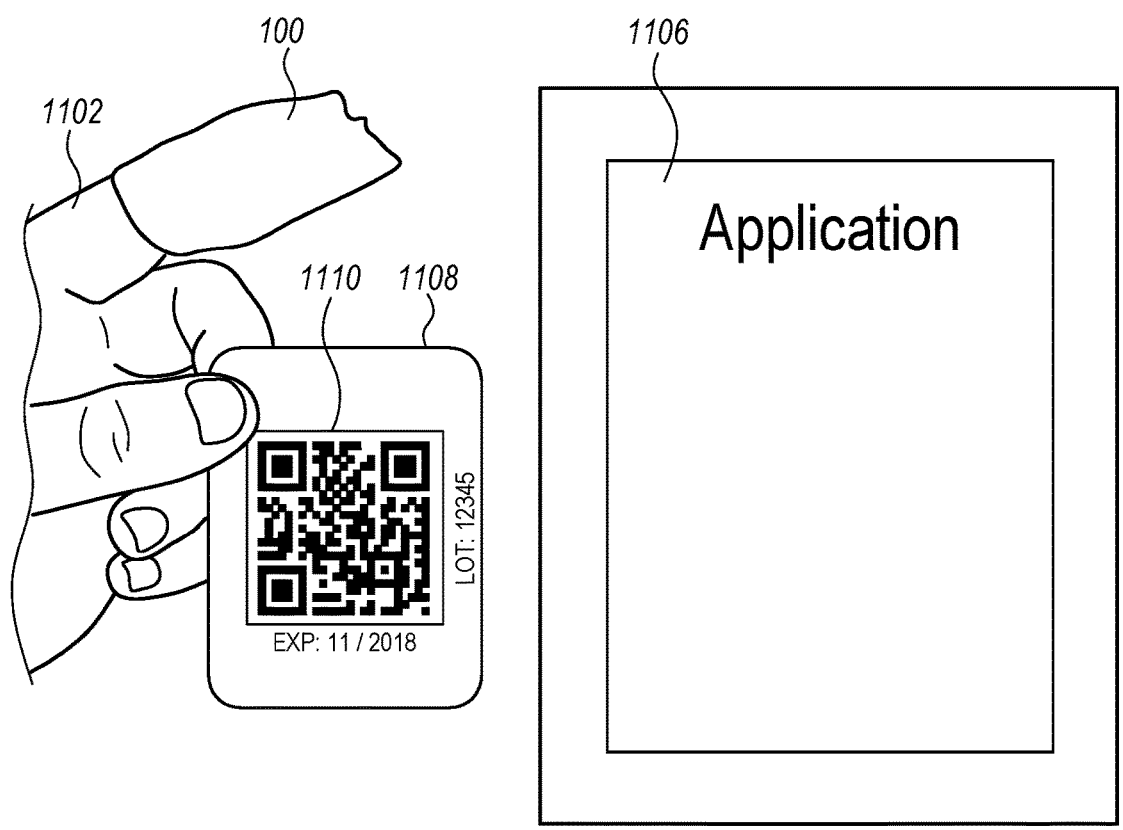
FIGS. 11A-11B depicts one example technique for scanning a label that includes an identifier for the medical device.
Figure 11B:
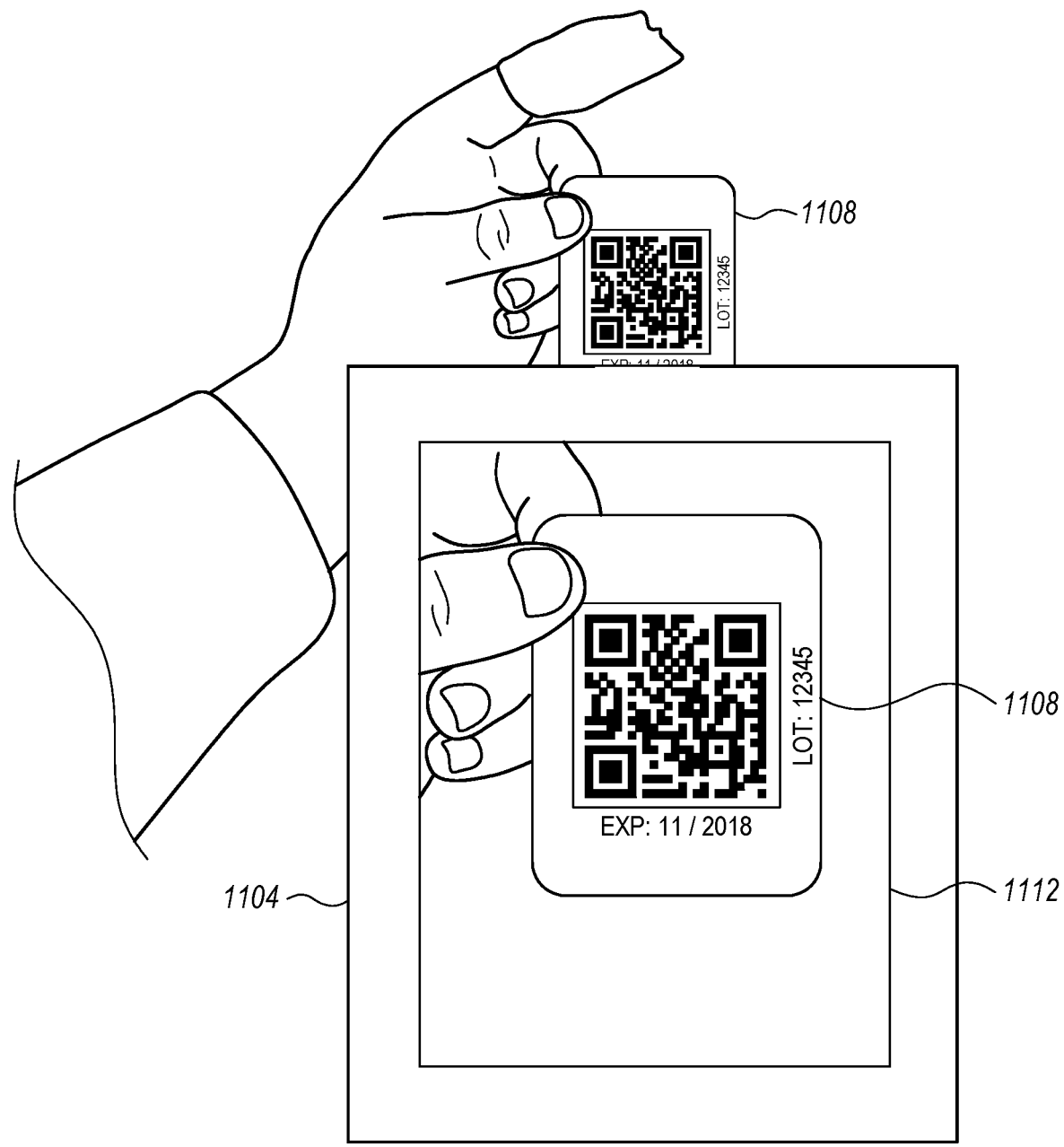

FIG. 10 is a flowchart illustrating an example method of authenticating a medical device once it is activated by the user using the identifier produced in FIG. 9. In one embodiment, the operations shown in FIG. 10 are performed at a host computing device. Initially, as shown in block 1000, the label with the identifier is scanned by the host computing device. FIGS. 11A-11B depicts one example technique for scanning a label that includes an identifier for the medical device. In FIG. 11A, the medical device 100 is attached to a user 1102 (e.g., a finger) via the adhesive surface on the medical device 100. Additionally, as shown in FIG. 11A, an attachment mechanism (e.g., a bandage or the biocompatible tape 802 in FIG. 8) is wrapped around the medical device and the finger. The medical device 100 is turned on so that the medical device 100 is ready to connect to the host computing device 1104.

The host computing device 1104 includes an application 1106 that receives and processes data from the medical device 100. The application 1106 includes a scanning operation that is used to scan the identifier 1110 on the label 1108. As discussed earlier, the label 1108 includes the identifier 1110.

In FIG. 11B, the label 1108 is positioned adjacent the host computing device 1104 for the scanning operation. For example, the label 1108 is positioned in front of an image capture device (e.g., input device 121 in FIG. 1) in, or connected to, the host computing device 1104. In some embodiments, an image of the label 1108 is displayed on a display 1112 (e.g., output device 122) of the host computing device 1104. The image capture device captures an image of the label 1108. The host computing device 1104 processes the image and the identifier 1110 to obtain at least the original hash number (computed in FIG. 9, block 902) and the data used to calculate the original hash number. As discussed earlier, the original has number can be computed based on the serial number, a version number, a lot number, an expiration date, a model number, and/or combinations thereof.

Returning to FIG. 10, the host computing device calculates an authentication hash number from the data in the identifier (block 1002). At block 1004, the host computing device compares the calculated authentication hash number to the original hash number (computed in FIG. 9) stored in the identifier that was scanned in block 1000. A determination is made at block 1006 as to whether the calculated authentication hash number matches the original hash number. If the two hash numbers do not match, the process passes to block 1008 where authentication of the medical device fails and a wireless connection between the medical device and the host computing device is not attempted. In some embodiments, the user can be informed of the failed authentication using any suitable output device, such as, for example, a text message displayed on a display or a verbal message output by a speaker.

When the calculated authentication hash number matches the original hash number at block 1006, the method continues at block 1010 where the host computing device computes a first pairing credential (e.g., hash number) based on data in the identifier 1110 that is also stored at the medical device. For example, in one embodiment, the serial number of the medical device included in the identifier 1110 is also stored in a storage device of the medical device. The first pairing credential is then computed based on the serial number. In other embodiments, other data in the identifier 1110, such as the lot number or the version number, may be stored at the medical device. In such embodiments, the other data can be used to determine a first pairing credential (e.g., hash number).

The host computing device then transmits the first pairing credential to the medical device at block 1012. The host computing device can transmit the first pairing credential wirelessly to the medical device using any suitable wireless communication protocol (e.g., Zigbee, BLE, ANT).

Next, as shown in block 1014, the medical device computes a second pairing credential (e.g., hash number) based on the data (e.g., the serial number) stored in a storage device of the medical device. A determination is made at block 1016 as to whether the first and the second pairing credentials match. If the two pairing credentials do not match, the process passes to block 1018 where the medical device is not paired with the host computing device. When the first and the second pairing credentials match, the method continues at block 1020 where the medical device is authenticated and the medical device connects or pairs with the host computing device. In some embodiments, the user can be informed of the successful authentication using any suitable output device, such as, for example, a text message displayed on a display or a verbal message output by a speaker.

Figure 12A:
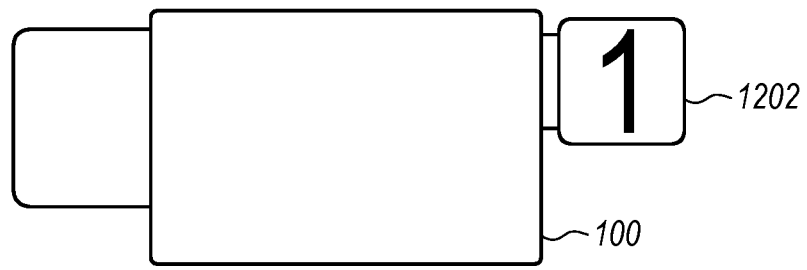
FIGS. 12A-12C illustrate an example method for activating the medical device.
Figure 12B:
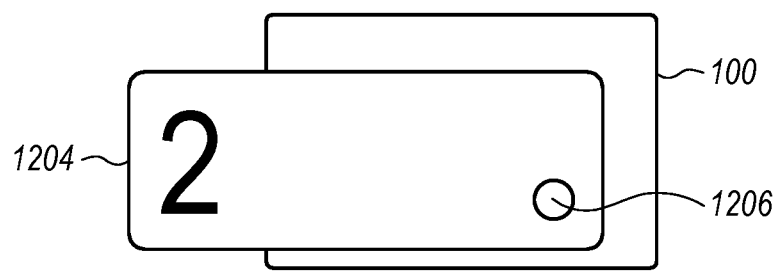
Figure 12C:
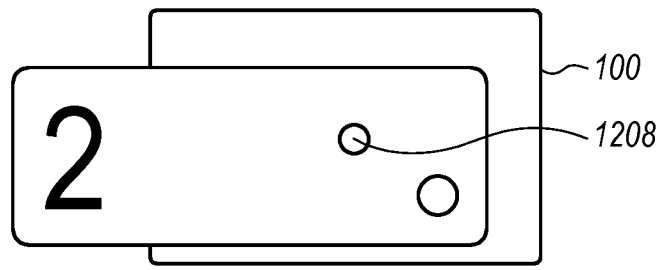

FIGS. 12A-12C illustrate an example method for activating a medical device. FIG. 12A is a bottom view of the medical device. The medical device 100 includes a removable first tab 1202 (indicated by "1"). The first tab 1202 is removed from the medical device 100. For example, the first tab 1202 can be a pull tab that is removed by pulling the tab 1202 away from the medical device 100.

FIG. 12B is a top view of the medical device 100 after the first tab 1202 has been removed. The medical device 100 includes a removable second tab 1204. A user presses on area 1206 (indicated by a circle) until an optical indicator turns on (see optical indicator 1208 in FIG. 12C). By pressing on area 1206, a user may assist in forming an electrical connection between a conductive contact and the two contact pads on the PCB 2402 (see e.g., contact pads 615 in FIGS. 6C and 35A), where the electrical connection activates the medical device 100. The illuminated optical indicator 1208 indicates the medical device 100 is turned on and activated.

FIG. 12C is a top view of the medical device 100 after the optical indicator 1208 is illuminated. The removable second tab 1204 is then removed from the medical device 100 in order to expose an adhesive tape 1210 on the surface 1212 of the medical device 100 (see FIG. 12D). For example, the second tab 1204 can be pull tab that is removed by pulling the tab 1204 away from the medical device 100.

Figure 12D:
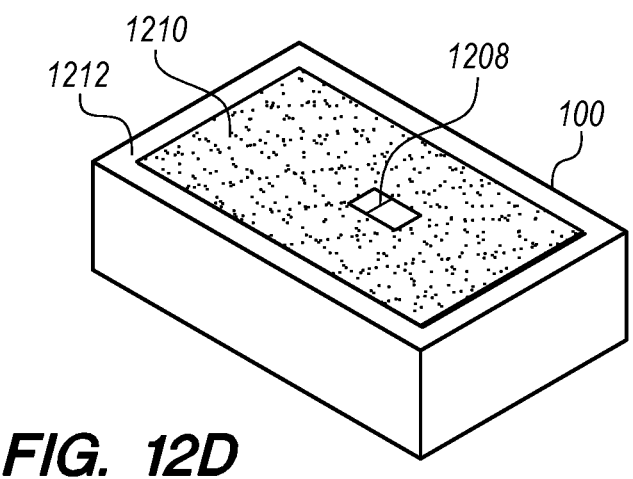
FIG. 12D depicts an isometric view of the medical device after activation.

FIG. 12D is an isometric view of the medical device 100 after the second tab 1204 has been removed. The optical indicator 1208 remains illuminated and indicates the medical device 100 is ready for attachment to a user.

Figure 13:
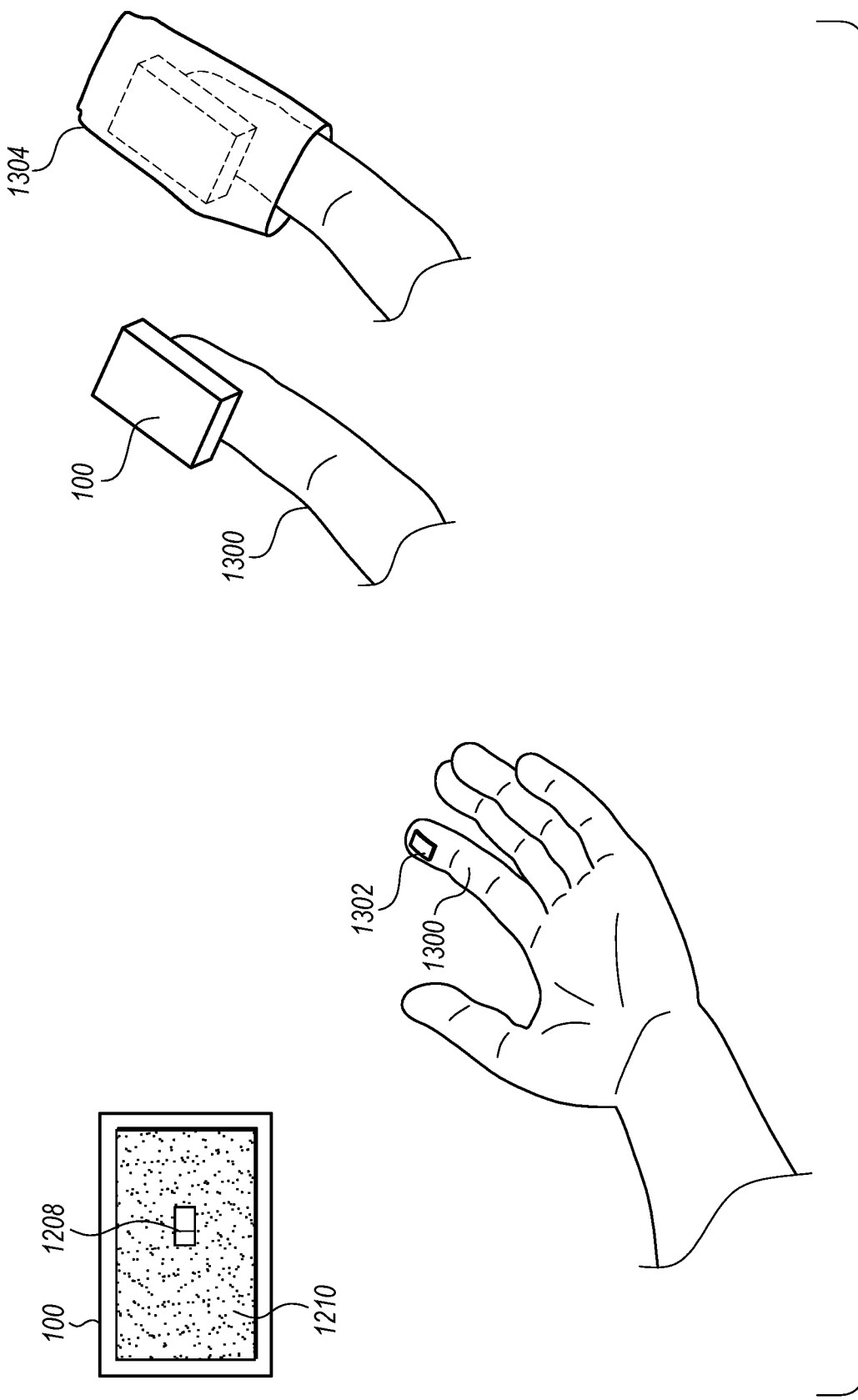
FIG. 13 illustrates an example method of attaching the medical device to a user.

FIG. 13 illustrates an example method of attaching the medical device to a user. Initially, the medical device 100 is positioned at a measurement site of the user with the optical indicator 1208 facing toward the measurement site. For example, as shown in FIG. 13, the medical device 100 is positioned on a user's index finger 1300 with the optical indicator facing area 1302 on the fingertip of the finger 1300 and the adhesive tape 1210 attached to the fingertip. An optional tape 1304, such as biocompatible tape 802 in FIG. 8, is wrapped around the fingertip and the medical device 100 to improve the optical compliance between the medical device 100 and the finger 1300 (e.g., the measurement site) and/or to protect the medical device 100.

Figure 14:
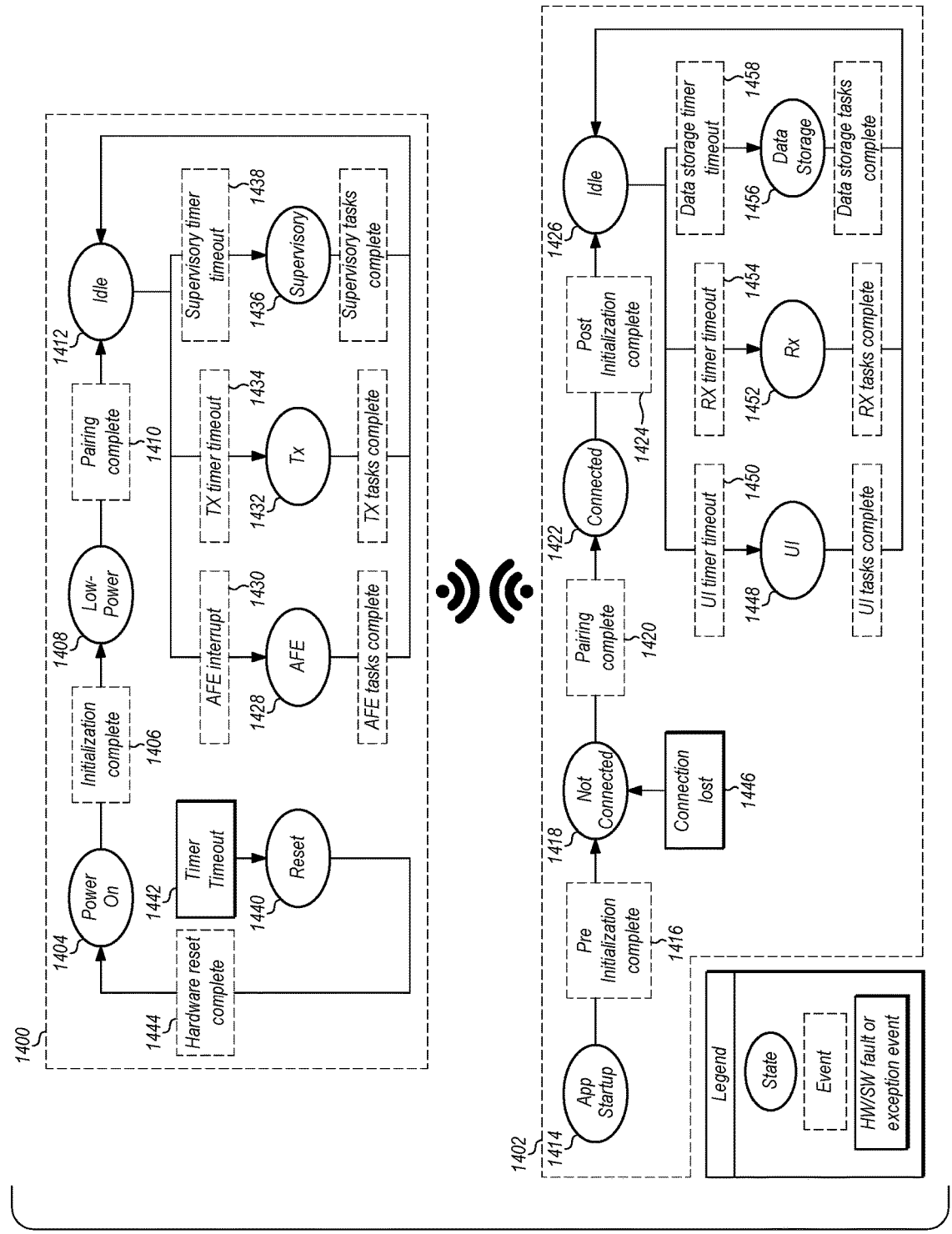
FIG. 14 depicts a state diagram of the medical device and a host computing device.

FIG. 14 depicts two state diagrams of the medical device and a host computing device operably connected and in communication using a wireless connection. Any suitable wireless protocol can be used for the wireless connection, such as BLE and Zigbee protocols. State diagram 1400 represents example firmware that can run in a medical device. State diagram 1402 represents an example Application software that may run in a host computing device. The state diagrams 1400, 1402 describe the architecture and operation of the firmware in the medical device and the Application software on the host computing device.

The following sequence of events in the illustrated state diagram 1400 of the medical device can occur in one embodiment, after the medical device is initially activated 1404. Once initialization is complete 1406, the medical device enters in low-power mode state 1408, and waits for the host computing device to send the authentication and pairing credentials (e.g., the authentication and pairing hash numbers). The authentication process described in conjunction with FIG. 10 can be part of the credential exchange process that occurs during device pairing. Once pairing is complete 1410, the medical device enters an idle state 1412 and waits for events, such as data acquisition and processing, data transmission, and supervisory tasks. As will be described in more detail later, the medical device is reset and re-initialized in the event of a hardware/software (HW/SW) failure or exception.

The following sequence of events in state diagram 1402 of the Application software may occur in one embodiment, after the Application begins executing 1414 and pre-initialization 1416 is completed. The host computing device, through the Application software, is in a "not connected" state 1418 and will search wirelessly for a medical device to connect to. When pairing is complete 1420 and the host computing device is connected to the medical device 1422, the Application software performs post-initialization 1424 and enters an idle state 1426. The host computing device, through the Application software, will then wait for events, such as data processing, data reception, storage, and transmission tasks. In the event of a lost wireless connection with the medical device, the Application software on the host computing device resumes a search for the medical device to reestablish the lost wireless connection.

The following provides a description of the firmware state diagram 1400 of the medical device.

Power On state 1404: Tests the operation readiness of the medical device. In case of an error, the firmware resets the medical device and starts over. If the error persists, the firmware transitions to an idle state. If the medical device does not respond in a given period of time to the host computing device, the lack of response can be considered an exception or fault.

Low-Power state 1408: Upon successful initialization, the medical device enters into a Low Power state until the wireless connection is established, so as to maximize battery life.

Idle State 1412: The medical device enters into an Idle State once the wireless connection is established with the host computing device. All application tasks may follow an event-driven model in order to minimize power consumption and remove the need for a Real-Time Operating System (RTOS) framework, so as to reduce the amount of memory and computational overhead.

AFE State 1428: A processing device in the medical device may communicate with an Analog Front End (AFE) by means of an interface, such as a Serial Peripheral Interface (SPI) bus. The communication between the AFE and the processing device is driven by hardware interruption events 1430, so as to minimize power consumption and enable low-latency response.

TX State 1432: The processing device in the medical device can send data packages (e.g., continuously) to the host computing device using a protocol, such as a UART/Serial Port Emulation over BLE protocol stack. The data packages may be sent periodically or at select times via timer expiration events 1434.

Supervisory State 1436: The firmware of the medical device asynchronously monitors the AFE, the optical sensor, and the battery voltage for correct and timely exception/error handling. The AFE, the optical sensor, and the battery voltage are periodically monitored via timer expiration events 1438.

Reset State 1440: The processing device of the medical device handles software and hardware recoverable faults, and/or exceptions by means of a timer 1442 that (if not reset from time to time) will reset and re-initialize 1444 the medical device.

The following provides a description of the Application software state diagram 1402 of the host computing device.

Application Startup State 1414: The Application software may display a startup screen that displays or provides information about the medical device and/or the Application software. Additionally or alternatively, the Application software can initialize all services and components used to connect and receive real-time data from the medical device.

Not Connected State 1418: The Application software searches and connects to the medical device, provided that the user inputs the proper authentication and pairing credentials, including, in some embodiments, a wireless password for the wireless connection. The Application software remains in the "not connected" state 1418 until a connection with the medical device is established. The Application software can re-establish a connection with the medical device whenever the connection is lost 1446 due to recoverable exceptions and/or faults.

Connected State 1422: The Application software initializes all services and components used to process, visualize, and/or store real-time data received from the medical device. In some embodiments, the Application software can generate warnings and alarms when required.

Idle State 1426: The Application software can be placed in an Idle State after a wireless connection is established with the medical device to release host computing device resources and/or reduce power consumption.

UI State 1448: The Application software can update measurements and trends, issues alarms and warnings, and may be responsive to User Interface (UI) requests whenever needed. The UI may be updated periodically via timer expiration events 1450.

RX State 1452: The Application software can receive data packages (e.g., continuously or at select times) from the medical device using a protocol, such as, for example, an UART/Serial Port Emulation over a BLE protocol stack. The data packages are processed to extract/estimate parameters of interest. Each data package can be received and processed periodically by means of timer expiration events 1454.

Data Storage State 1456: The Application software can store the real-time data received from the medical device using any suitable storage technique, such as, for example, log files, databases and/or tables. Additionally or alternatively, the Application software may store data that is processed by the Application software itself. Data storage may occur periodically via timer expiration events 1458.

Figure 17:
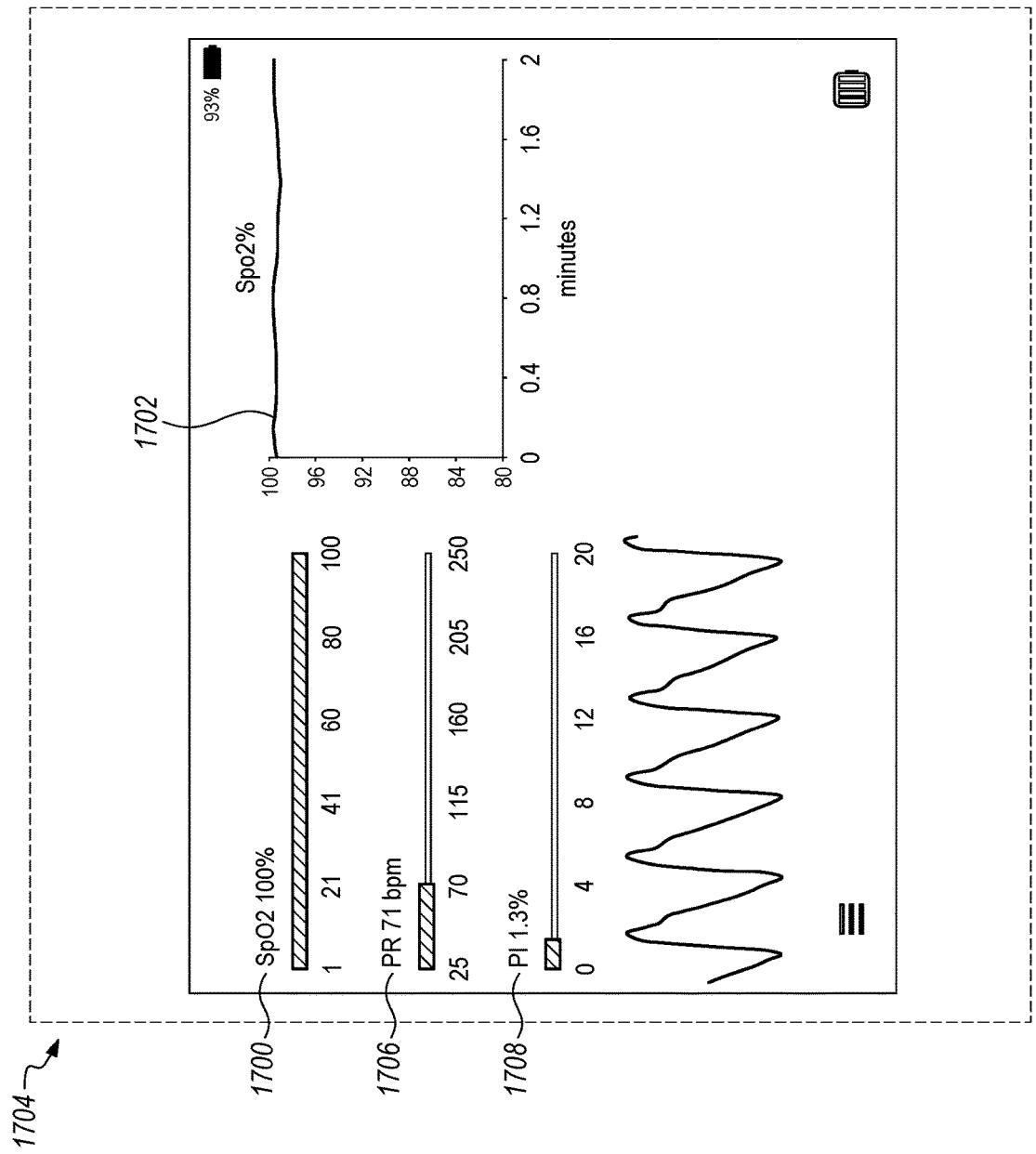

FIGS. 15-19 illustrate example user interface views of the Application software that can be displayed on the host computing device. The dashed line in FIGS. 15, 16, 18, and 19 represents a host computing device and the user interface view is displayed on a display device (e.g., a touchscreen). The dashed line in FIG. 17 represents a display screen of a display device (e.g., a display screen on a touchscreen).

As described earlier, the host computing device is connected wirelessly to a medical device. The medical device, in combination with the host computing device, together form a pulse oximetry system. FIG. 15 depicts an example "Start" user interface view 1500 that can be displayed on the host computing device, where a user can scan 1502 the identifier on the label (e.g., the barcode), display the barcode and/or other data associated with the medical device 1504 (e.g., serial number, model number, etc.), enter or scan a patient's or user's ID 1506, and/or enter a patient's or user's gender 1508 and Date of Birth 1510.

FIG. 16 illustrates a measurement user interface view that can include measurement types, values, gauges, and/or waveforms. The example user interface view 1600 includes three measurement types 1602, 1604, 1606. Other embodiments can display one or more measurement types. The measurement type 1602 displays in real-time the user's oxygen saturation (SpO2) as a numerical value 1608. Additionally or alternatively, in some embodiments, a measurement gauge 1610 can display the numerical value in a graphical form, such as a horizontal bar (shown in FIG. 16) or a pie chart.

The measurement gauge type 1604 displays in real-time the user's pulse rate (PR) as a numerical value 1612. Additionally or alternatively, in some embodiments, a measurement gauge 1614 may display the numerical value in a graphical form (e.g., a horizontal bar).

The measurement type 1606 displays in real-time the user's perfusion index (PI) as a numerical value 1616. Additionally or alternatively, in some embodiments, a measurement gauge 1618 may display the numerical value in a graphical form (e.g., a horizontal bar).

In some embodiments, the measurement user interface view 1600 can also display in real-time the user's photoplethysmographs 1620. The measurement user interface view 1600 may further display a fuel gauge 1622 that displays the battery power levels for the medical device, and an icon 1624 that enables or provides access to one or more menus (e.g., an Options Menu) and/or other functionalities. For example, from the Options Menu, a user can access the "Start" screen 1500, a "Share Data" screen (see FIG. 19), and/or a "Settings" screen (see FIG. 18), as well as other screens that may provide additional functionalities.

FIG. 17 depicts a measurement user interface view that provides all the functionalities from the measurement user interface view 1600 of FIG. 16 as well as trend data functionalities. The measurement type 1700 (shown in boldface font) indicates that a SpO2 trend data 1702 is displayed in the measurement user interface view 1704 (e.g., on the right side of the measurement user interface view 1704). The user can select the measurement types 1706, 1708 to switch the corresponding trend data displayed on the right side of the measurement user interface view 1704. For example, in one embodiment, the user may touch a particular measurement type to select the measurement type when the measurement user interface view 1704 is presented on a touchscreen.

Figure 18:
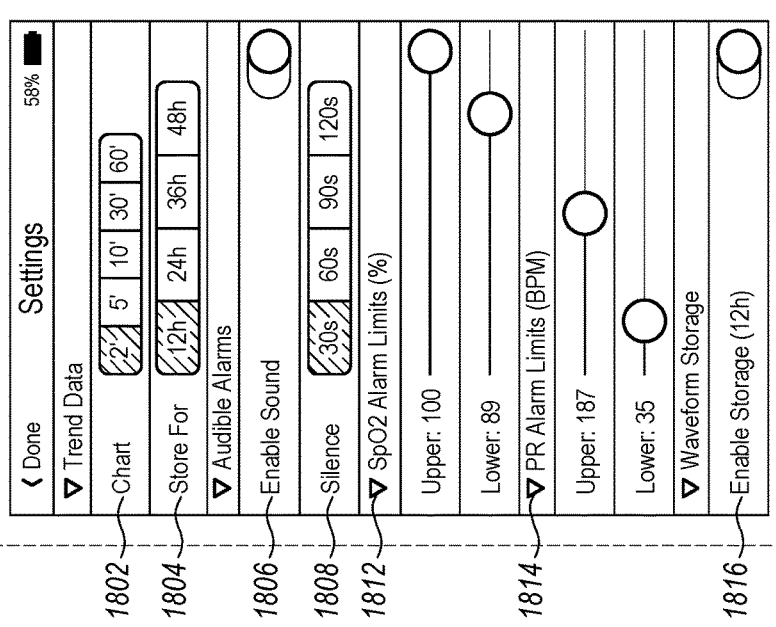

FIG. 18 illustrates an example settings user interface view. In some embodiments, the settings user interface view can be accessed via the icon 1624 in FIG. 16. The settings user interface view 1800 allows a user to set various settings for the Application software, including the measurement types, values, waveforms, and gauges. For example, an amount of time for a trend data chart can be set using setting 1802. In a non-limiting embodiment, the amount of time options that can be selected include 2, 5, 10, 30 or 60 minutes.

A trend data storage period may be set using setting 1804. Example storage options include, but are not limited to, the last 12, 24, 36 or 48 hours. In some embodiments, the trend data storage period is a rolling time period once trend data for the amount of time is stored. For example, once trend data for 12 hours is stored, new trend data is stored in a storage device and the oldest trend data is deleted from the storage device.

Settings associated with an audible alarm may be set via the settings user interface view 1800. The audible alarm can be enabled or disabled using setting 1806. An alarm silence time period in which the audible alarm is temporarily silenced may be set using setting 1808. For example, when an alarm is provided, a user can select any element in the user interface to silence the alarm for a limited time period. Example alarm silence time periods include 30, 60, 90, and 120 seconds. Other time periods can be used for the trend data chart 1802, the trend data storage 1804, and the silence time period 1808.

In some embodiments, upper and lower alarm limits for select measurement types can be set via the settings user interface view 1800. When a measurement is equal to or greater than an upper limit, an alarm can be provided. Similarly, an alarm may be provided when a measurement equals or is less than the lower limit. In the illustrated embodiment, upper and lower alarm limits can be set for the SpO2 and the PR measurements 1812, 1814. In a non-limiting example, each alarm limit can be specified using a sliding switch. Other embodiments can use a different mechanism to specify each alarm limit, such as a dialog box or a pull-down menu. The setting 1816 may be used to set or enable a waveform storage time period (e.g., the last 12 hours).

Figure 19:
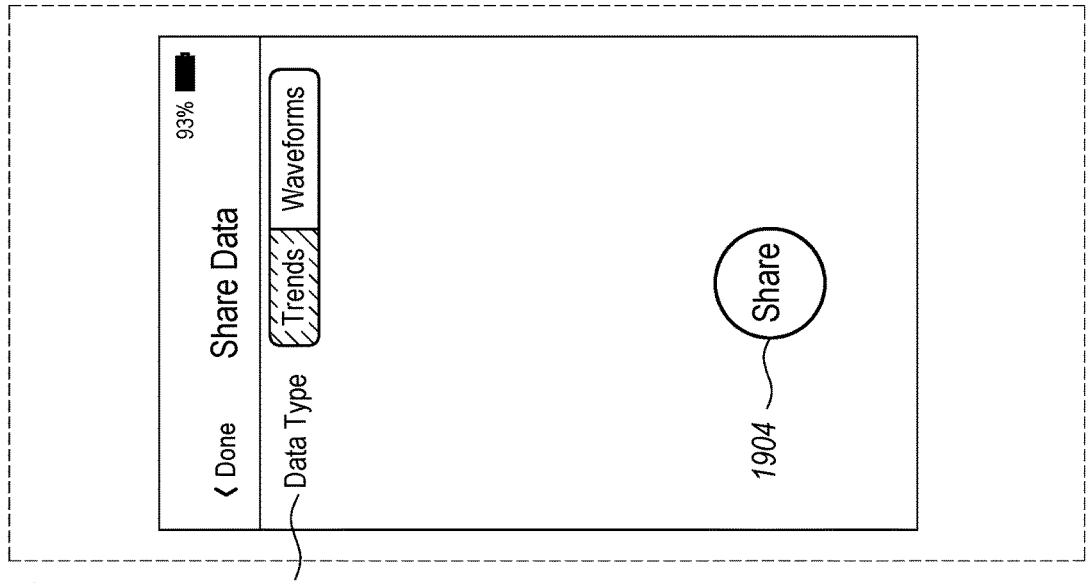

FIG. 19 depicts an example share data user interface view. In some embodiments, the share data user interface view can be accessed via the icon 1624 in FIG. 16. Using the share data user interface view 1900, a user can choose the data type 1902 to be shared with a third party device (e.g., trends or waveforms). The user may select a "Share" input button 1904 when the user is ready to share the data with the third party device. When the "Share" input button 1904 selected, a share operation transfers data to the third party device via one or more sharing methods or applications (e.g., email, text message, cloud, etc.) that are available in the host computing device and/or in the medical device. In some embodiments, the data types to be shared with a third party device may include one or more of PDF reports, EMR records, trend data, waveform data, hardware and/or software diagnostics data, and the like.

Figure 20A:
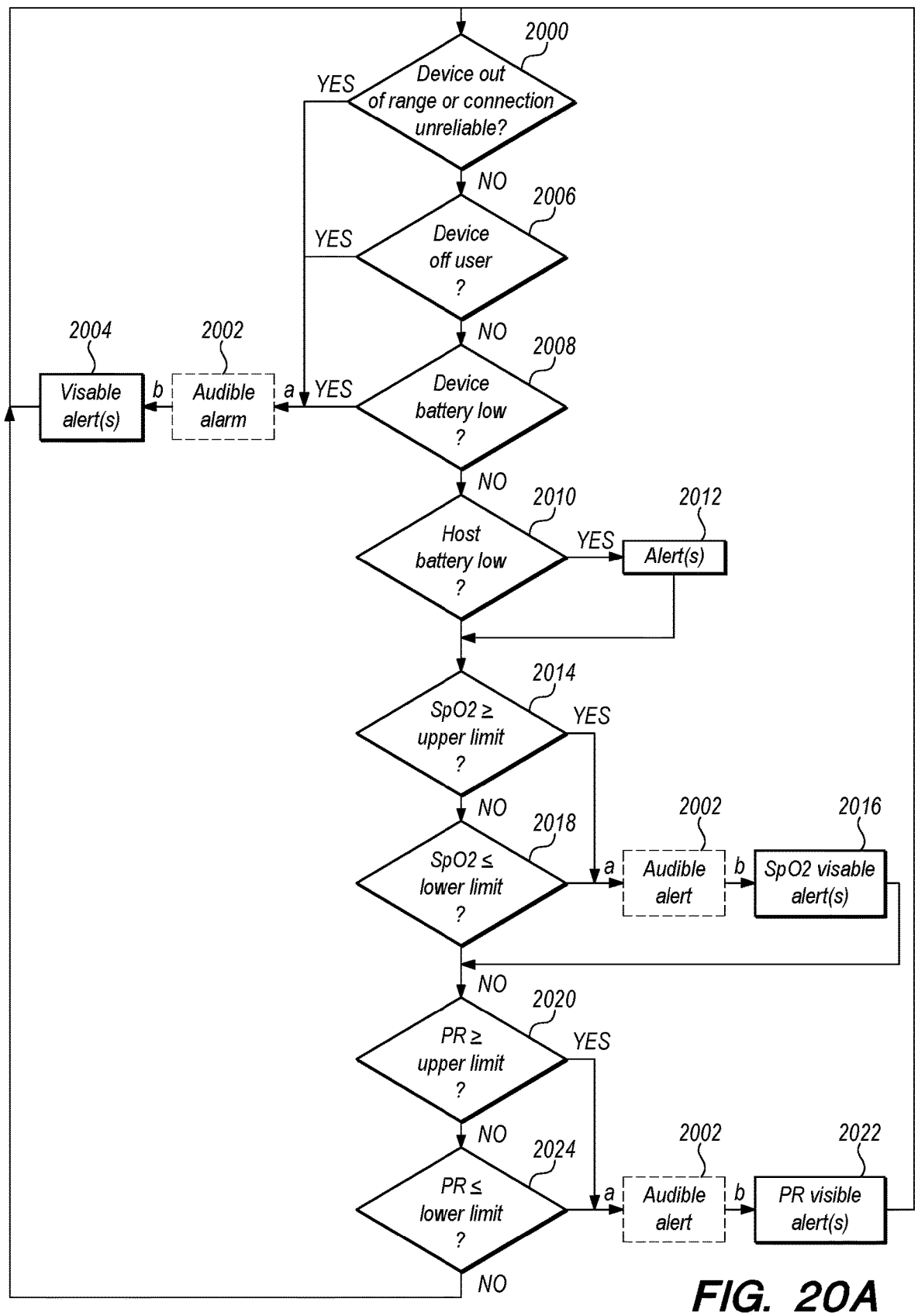
FIG. 20A is a flowchart depicting an example method of operating an alarm system.

FIG. 20A is a flowchart depicting an example method of operating an alarm system. Initially, a determination is made at block 2000 as to whether the medical device is out of range of the host computing device or if the wireless connection between the medical device and the host computing device is unreliable (e.g., slow data transmission rates or repeated disconnections). If so, the process passes to block 2002 where optionally an audible alarm is produced by the host computing device. In some embodiments, the audible alarm can be output by the medical device instead of, or in addition to, the host computing device.

Additionally or alternatively, one or more visible alerts can be produced at the host computing device at block 2004. For example, one or more elements in the user interface of the Application can be changed and/or emphasized. For example, a measurement type, gauge, or value can change color, blink on and off, and/or change font or font style (e.g., bold, italicize). In some embodiments, haptic feedback, a text message, and/or one or more audible sounds can be produced by the host computing device in addition to, or as an alternative to, the visual alerts. The method then returns to block 2000.

When the medical device is within range of the host computing device and the wireless connection between the medical device and the host computing device is reliable, a determination can be made at block 2006 as to whether the medical device is not attached to the user. The phrase "not attached" can refer to situations where the medical device is not attached to a user, or the medical device is attached to a user but is not transmitting valid physiological data obtained from the user to the host computing device. For example, when the medical device is within range of the host computing device and the wireless connection is reliable, but the host computing device is not receiving any valid physiological data from the medical device, a determination can be made that the medical device is not attached to a user. The method continues at optional block 2002 and block 2004 when the medical device is not attached to a measurement site.

When the medical device is attached to the user, the process continues at block 2008 where a determination is made as to whether the amount of power or energy stored on the battery in the medical device is low. For example, the amount of power stored on the battery can be low when the amount of power falls below a threshold value. If so, the method continues at optional block 2002 and block 2004.

When the amount of power or energy stored on the battery in the medical device is not low, the process passes to block 2010 where a determination is made as to whether the amount of power or energy stored on the battery in the host computing device is low. For example, the amount of power stored on the battery can be low when the amount of power falls below a threshold value. If so, the method continues at block 2012 where the host computing device provides one or more warnings or alerts. In a non-limiting example, the host computing device can display one or more text messages, output audible alerts or sounds, provide haptic feedback, and the like.

When the determination at block 2010 is that the amount of power or energy stored on the battery in the host computing device is not low, or after block 2012, the process continues at block 2014 where a determination is made as to whether a measurement of blood oxygen saturation SpO2 is equal to or greater than the upper limit set for the audible alarm (e.g., SpO2 alarm limits 1812 in FIG. 18). When the SpO2 measurement equals or exceeds the upper limit, the method passes to block 2002 where an optional audible alert is provided. Additionally or alternatively, visible alerts can be produced by the host computing device at block 2016. For example, the SpO2 measurement type, gauge, or value can change color, blink on and off, and/or change font or font style (e.g., bold, italicize). In some embodiments, a text message can be displayed by the host computing device in addition to, or as an alternative to, the visual alerts. The process then continues at block 2020.

When the SpO2 measurement equals or is less than the upper limit, the method passes to block 2018 where a determination is made as whether a measurement of blood oxygen saturation SpO2 is equal to or less than the lower limit set for the audible alarm (e.g., SpO2 alarm limits 1812 in FIG. 18). When the SpO2 measurement equals or is less than the lower limit, the method continues at block 2002 where an optional audible alert is provided. Additionally or alternatively, visible alerts can be produced by the host computing device at block 2016. For example, The SpO2 measurement type, gauge, or value can change color, blink on and off, and/or change font or font style (e.g., bold, italicize). In some embodiments, haptic feedback, a text message, and/or one or more audible sounds can be provided by the host computing device in addition to, or as an alternative to, the visual alerts. The process then passes to block 2020.

When the SpO2 measurement equals or is greater than the lower limit, the method continues at block 2020 where a determination is made as whether a measurement of the pulse rate PR is equal to or greater than the upper limit set for the audible alarm (e.g., PR alarm limits 1814 in FIG. 18). When the PR measurement equals or exceeds the upper limit, the method passes to block 2002 where an optional audible alert is provided. Additionally or alternatively, visible alerts can be produced by the host computing device at block 2022. For example, The PR measurement type, gauge, or value can change color, blink on and off, and/or change font or font style (e.g., bold, italicize). In some embodiments, haptic feedback, a text message, and/or one or more audible sounds can be output by the host computing device in addition to, or as an alternative to, the visual alerts. The process then returns to block 2000.

When the PR measurement equals or is less than the upper limit, the method passes to block 2024 where a determination is made as whether the PR measurement is equal to or less than the lower limit set for the audible alarm (e.g., PR alarm limits 1814 in FIG. 18). When the PR measurement equals or is less than the lower limit, the method continues at block 2002 where an optional audible alert is provided. Additionally or alternatively, visible alerts (and/or other types of alerts) can be produced by the host computing device at block 2022. After block 2022 is performed, or when the PR measurement equals or is greater than the lower limit, the method returns to block 2000.

Other embodiments can implement the method shown in FIG. 20A differently by adding, modifying, omitting, or re-arranging the blocks. For example, blocks 2010 and 2012 may be omitted in other embodiments. Additionally or alternatively, the decisions at blocks 2014, 2018, 2020, 2024 can determine whether the SpO2 or the PR measurements are greater than the associated upper limit or less than the associated lower limit (e.g., alarm and/or alert not generated when a measurement is equal to the upper or lower limit).

Figure 20B:
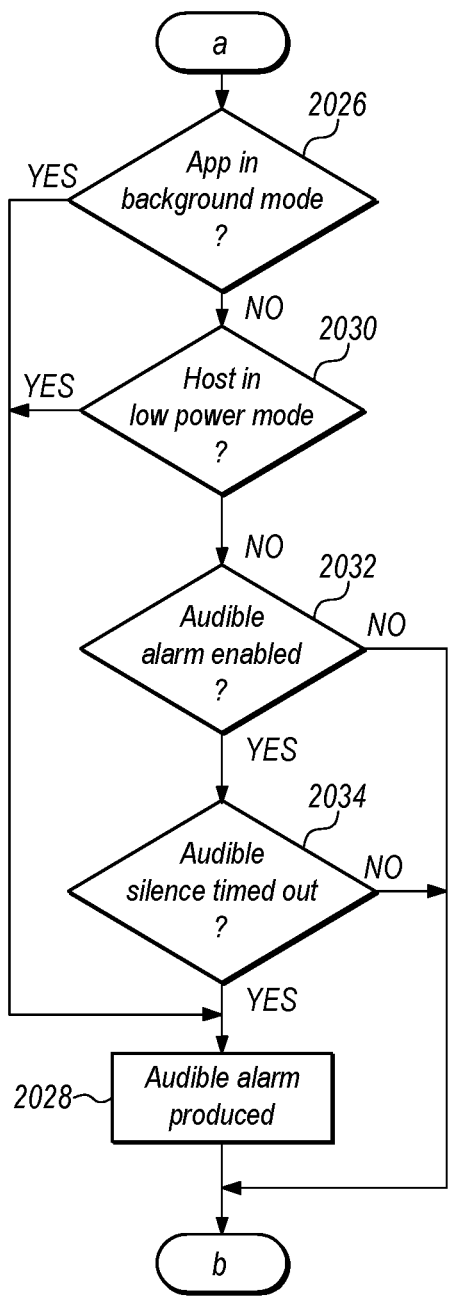
FIG. 20B is a flowchart illustrating an example method of producing an audible alarm.

FIG. 20B is a flowchart illustrating an example method of producing an audible alarm. The operations shown in FIG. 20B can be performed in block 2002 in FIG. 20A. Initially, a determination is made at block 2026 as to whether the Application software on the host computing device is in background mode. In some instances, the host computing device can run multiple applications in addition to the Application software associated with the medical device. The Application software is running in the background ("background mode") when another application is running in the foreground. In some embodiments, when the Application software is running in background mode, the process continues at block 2028 where the audible alarm is provided. Thus, in some embodiments, the audible alarm is provided regardless of whether the Application software is running in background or foreground mode. In other embodiments, an audible alarm may not be produced by the host computing device when the Application software is running in background mode. In such embodiments, the method can begin at block 2030 or block 2032.

When the Application software is not running in background mode (e.g., is running in foreground mode), the method passes to block 2030 where a determination is made as to whether the host computing device is currently in a low power mode. For example, the host computing device may be in a sleep mode, an airplane mode, a silent mode, or another power saving mode. In some embodiments, when the host computing device is in a low power mode, the process continues at block 2028 where the audible alarm is provided. Thus, in some embodiments, the audible alarm is provided regardless of whether the host computing device is in, or not in, a low power state. In other embodiments, an audible alarm may not be produced when the host computing device is operating in a low power state. In such embodiments, the method can begin at block 2032.

When the host is not in a low power mode at block 2030, the process continues at block 2032 where a determination is made as to whether the audible alarm is enabled. If not, the method passes to block 2004, 2016, or 2022 depending on the state of the method. When the audible alarm is enabled, the process continues at block 2034 where a determination is made as to whether the alarm silence is activated. If the alarm silence is activated (i.e., not timed out), the method passes to block 2004, 2016, or 2022 (FIG. 20A) depending on the state of the method. When the alarm silence is not activated, the audible alarm is generated at block 2028.

Other embodiments can implement the method shown in FIG. 20B differently by adding, modifying, omitting, or re-arranging the blocks. For example, blocks 2026 and 2030 may be omitted in other embodiments. Additionally or alternatively, block 2028 may be performed before block 2034 and if the alarm silence has not timed out, the process may wait at block 2034 until the alarm silence has timed out. When the alarm silence times out at block 2034, the method can return to block 2028 and blocks 2028 and 2034 may repeat until the alarm is turned off.

Figure 21:
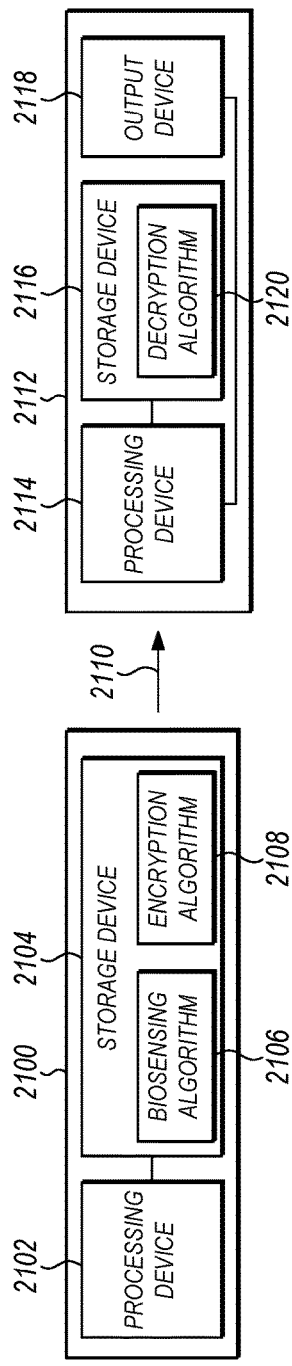
FIG. 21 depicts a block diagram of a first configuration for a medical device and a host computing device.

FIG. 21 illustrates a block diagram of a first configuration for a medical device and a host computing device. In the illustrated embodiment, a medical device 2100 includes a processing device 2102 operably connected to a storage device 2104. The storage device 2104 stores a biosensing algorithm 2106 and an encryption algorithm 2108 that are each executed by the processing device 2102. The biosensing algorithm 2106 processes data collected by the medical device to produce health related measurement results that are in a form that is meaningful or understandable to various users (e.g., individuals wearing the medical device, caregivers, health care professionals). The health related measurement results are encrypted using the encryption algorithm 2108 and transmitted 2110 to the host computing device 2112.

The host computing device 2112 includes a processing device 2114 operably connected to a storage device 2116 and an output device 2118. The storage device 2116 stores a decryption algorithm 2120 that is executed by the processing device 2114 to decrypt the encrypted health related measurement results. The processing device 2114 provides the decrypted health related measurement results to the output device 2118. For example, the host computing device can display the results on a display screen (e.g., a touchscreen).

One limitation with the configuration in FIG. 21 is that unauthorized persons or systems (e.g., a hacker) can obtain the health related measurement results during transmission 2110 from the medical device 2100 to the host computing device 2112. Although the health related measurement results are encrypted during transmission 2110, an unauthorized person or system may be able to decrypt some or all of the health related measurement results. Since the health related measurement results are in a form that is meaningful or understandable to users, the health related measurement results are also meaningful or understandable to the unauthorized person or system.

Figure 22:
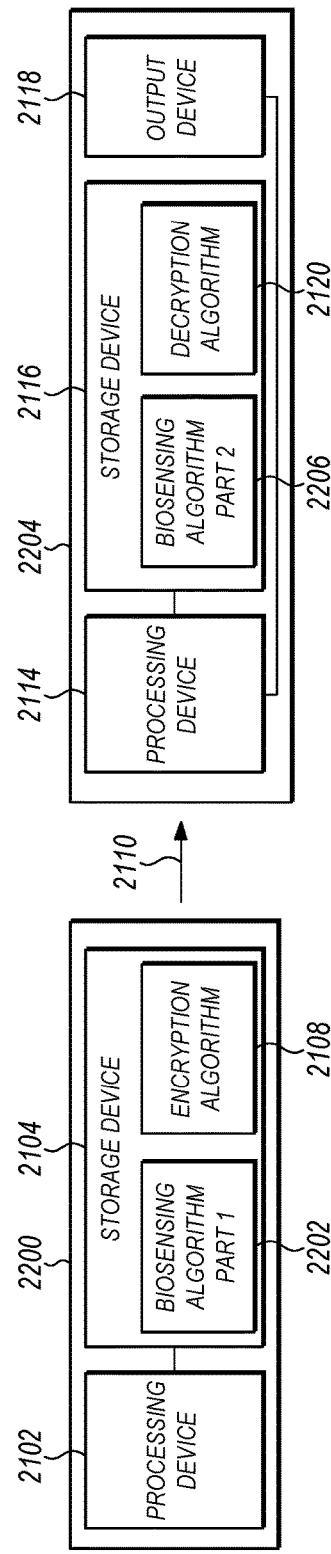
FIG. 22 illustrates a block diagram of a second configuration for a medical device and a host computing device.
Figure 23:
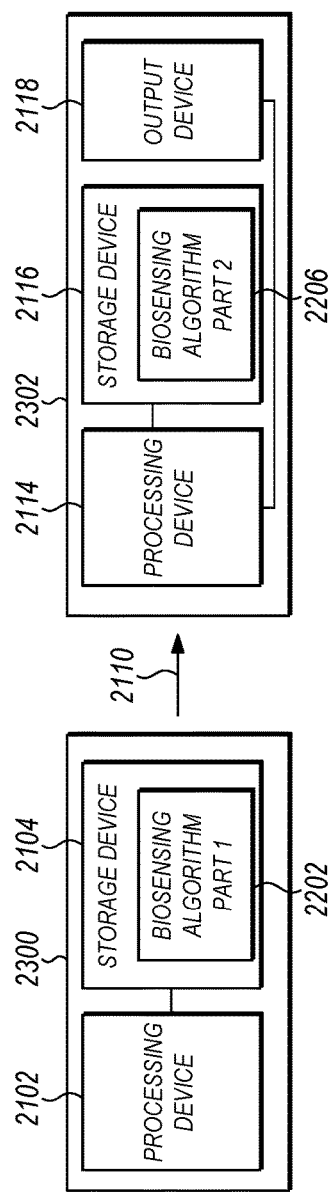
FIG. 23 depicts a block diagram of a third configuration for a medical device and a host computing device.

Embodiments described in conjunction with FIGS. 22 and 23 provide improved security for the health related measurement results. In FIGS. 22 and 23, the biosensing algorithm that processes the data collected by the medical device is grouped into two parts, Part 1 and Part 2. Part 1 process the data collected by the medical device and produces intermediate results. However, the intermediate results are not in a form that is meaningful or understandable to users. Part 2 processes the intermediate results to produce health related measurement results in a form that is meaningful or understandable to users. For example, Part 1 of the biosensing algorithm may produce data that relates to one or more waveforms (e.g., photoplethysmographs) or trend data, and Part 2 can produce the numerical values for one or more measurement types (e.g., SpO2, PR, and/or PI).

FIG. 22 depicts a block diagram of a second configuration for a medical device and a host computing device. In the illustrated embodiment, a medical device 2200 includes a processing device 2102 operably connected to a storage device 2104. The storage device 2104 stores Part 1 of a biosensing algorithm 2202 and an encryption algorithm 2108. Part 1 of the biosensing algorithm 2202 and the encryption algorithm 2108 are each executed by the processing device 2102. Part 1 of the biosensing algorithm 2202 processes data collected by the medical device to produce intermediate health related measurement results that are in a form that is not meaningful or understandable to various users. The intermediate health related measurement results are encrypted using the encryption algorithm 2108 and transmitted 2110 to the host computing device 2204.

The host computing device 2204 includes a processing device 2114 operably connected to a storage device 2116 and an output device 2118. The storage device 2116 stores Part 2 of the biosensing algorithm 2206 and the decryption algorithm 2120. Part 2 of the biosensing algorithm and the decryption algorithm are each executed by the processing device 2114. The encrypted intermediate health related measurement results are decrypted using the decryption algorithm 2120. The decrypted intermediate health related measurement results are then processed using Part 2 of the biosensing algorithm 2206 to produce health related measurement results that are in a form that is understandable or meaningful to various users. The processing device 2114 provides the health related measurement results to the output device 2118. For example, the host computing device can display the results on a display screen (e.g., a touchscreen).

FIG. 23 illustrates a block diagram of a third configuration for a medical device and a host computing device. In this representative embodiment, the intermediate health related measurement data is not encrypted or decrypted by the medical device and the host computing device, respectively. A medical device 2300 includes a processing device 2102 operably connected to a storage device 2104. The storage device 2104 stores Part 1 of a biosensing algorithm 2202. Part 1 of the biosensing algorithm 2202 is executed by the processing device 2102 to processes data collected by the medical device and produce intermediate health related measurement results that are in a form that is not meaningful or understandable to various users. The intermediate health related measurement results are transmitted 2110 to the host computing device 2302.

The host computing device 2302 includes a processing device 2114 operably connected to a storage device 2116 and an output device 2118. The storage device 2116 stores Part 2 of the biosensing algorithm 2206. Part 2 of the biosensing algorithm is executed by the processing device 2114 to process the intermediate health related measurement results and produce health related measurement results that are in a form that is understandable or meaningful to various users. The processing device 2114 provides the health related measurement results to the output device 2118. For example, the host computing device can display the results on a display screen (e.g., a touchscreen).

In the configurations of FIGS. 22 and 23, the intermediate health related measurement data transmitted to the host computing device is in a form that is not understandable or meaningful to both users, unauthorized persons, and unauthorized systems. An unauthorized person or system must be knowledgeable about both Part 1 and Part 2 of the biosensing algorithm to process and understand the intermediate health related measurement data.

Figure 24:
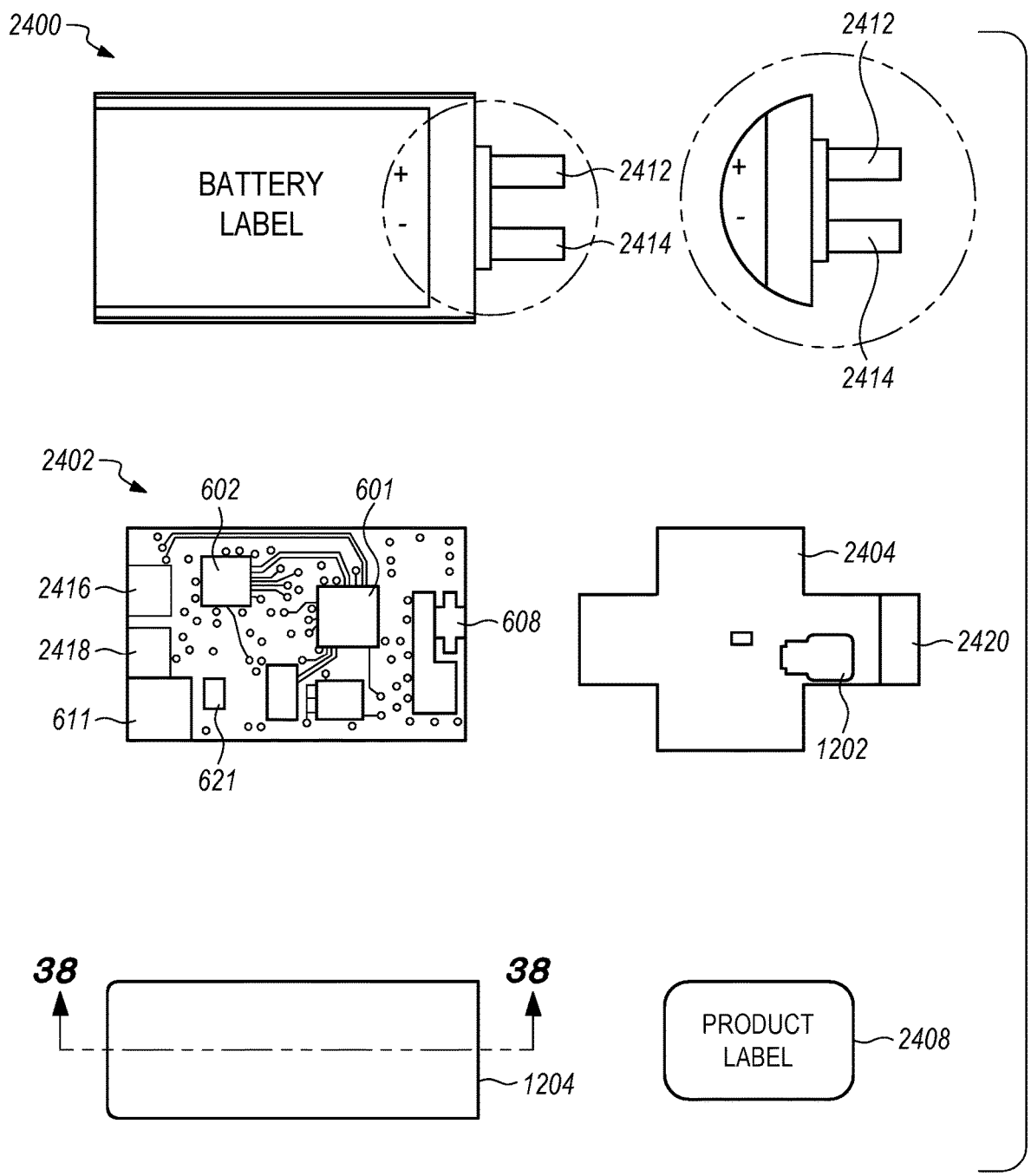
FIG. 24 illustrates top views of example components of a medical device.

FIG. 24 illustrates example components of a medical device. The components include a battery 2400, a printed circuit board (PCB) 2402 that includes electronic circuitry that performs the functionalities of the medical device, a tape encapsulation assembly 2404, the removable first tab 1202, a product label 2408, and the removable second tab 1204. The battery 2400 can be implemented with any suitable battery. The battery 2400 includes a first terminal 2412 (e.g., positive terminal) and a second terminal 2414 (e.g., negative terminal). In one embodiment, the battery 2400 is a lithium manganese dioxide (Li—MnO2) non-rechargeable battery. The Li—MnO2 battery can provide high energy density (about 250 Wh/kg), a wide operating temperature range (−5 to 60 Celsius), and/or a long shelf life due to very low rate of self-discharge. In some instances, the Li—MnO2 battery can withstand high pulse current transients that typically occur in wireless radio circuitries. In other embodiments, different battery technologies (such as silver oxide, etc.) can be used. For example, a silver oxide battery having comparable energy density, temperature range, shelf life, and/or maximum electrical current can be used.

The PCB 2402 may be rigid or flexible, or be in the form of a substrate, where some or all the components are die attached and wire bonded to the substrate. In one aspect, the PCB 2402 is encapsulated for protection using epoxy or some other encapsulation material. In a non-limiting embodiment, the electronic schematics shown in FIGS. 6A-6C can be implemented on the PCB 2402. A layout with the processing device 601, the integrated circuit 602, the antenna 608, the ferrite inductor 611, the boost converter 621, and two contact pads 2416, 2418 is shown in FIG. 24. The optical sensor 603 is attached on the bottom side of the PCB 2402 (see FIG. 25B).

The tape encapsulation assembly 2404 may be a single coated foam medical tape with a biocompatible foam backing. The tape encapsulation assembly 2404 can include a conductive contact (see 2808 in FIG. 33) that operates as a one-time ON switch to activate the medical device when a user removes the removable first tab 1202. The tape encapsulation assembly 2404 further includes a release liner 2420. FIGS. 26A-34B illustrate a method for constructing the biocompatible adhesive tape encapsulation assembly 2404.

Figure 38:
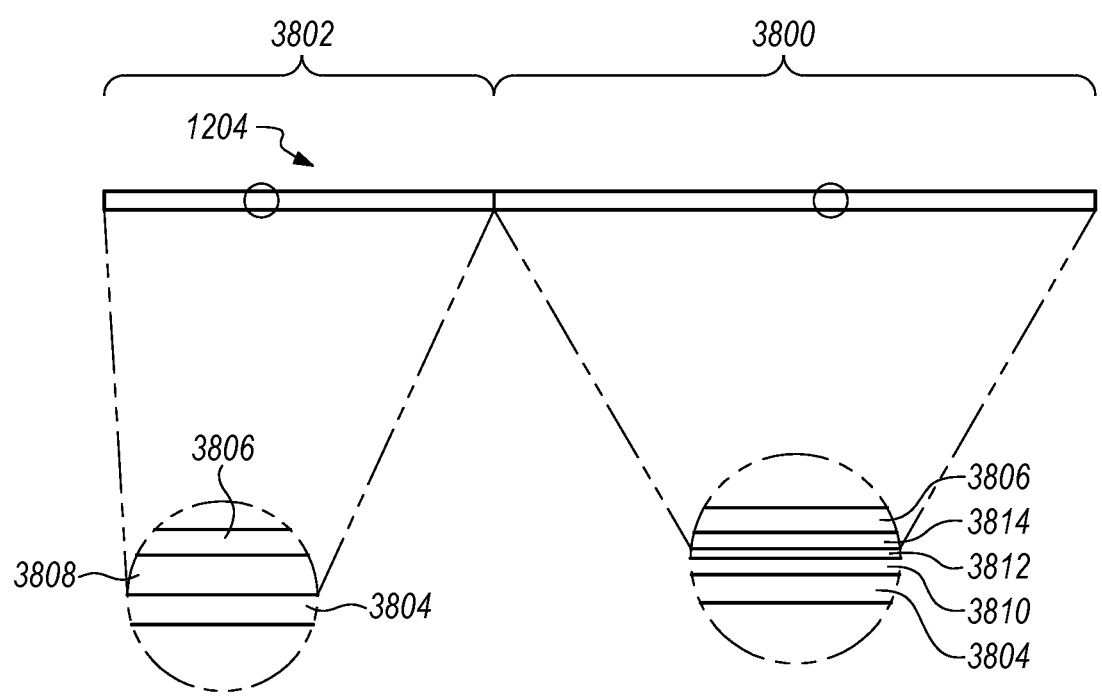
FIG. 38 illustrates a cross-sectional view of an example removable second tab.

The second tab 1204 is removable, and when removed, exposes a portion of the tape encapsulation assembly 2404 that can be used to attach the medical device to a measurement site on a user. FIG. 38 depicts detailed cross-sectional views of an example second tab 1204.

Figure 25A:
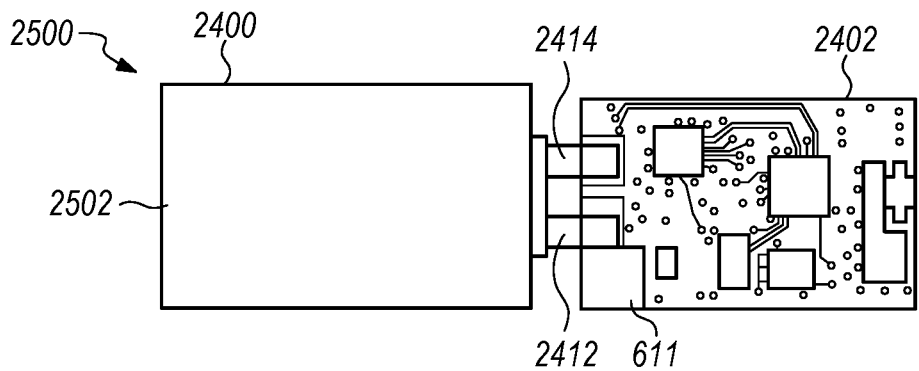
FIGS. 25A-37B depict an example method of assembling a medical device.
Figure 25B:
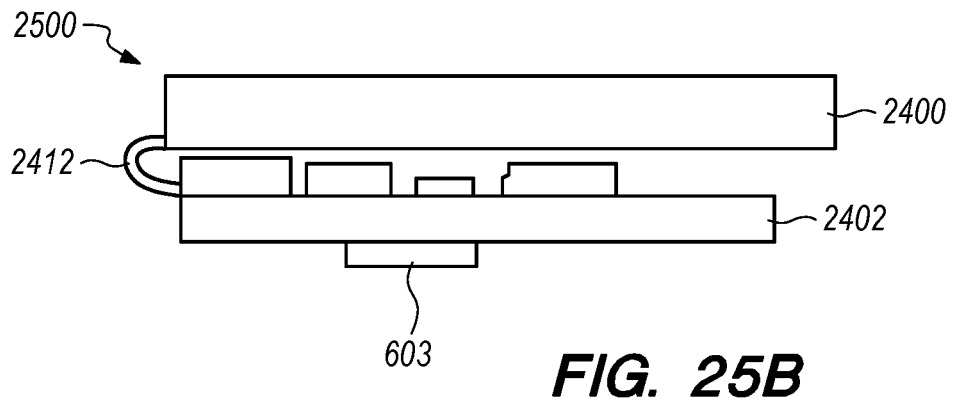
Figure 25C:
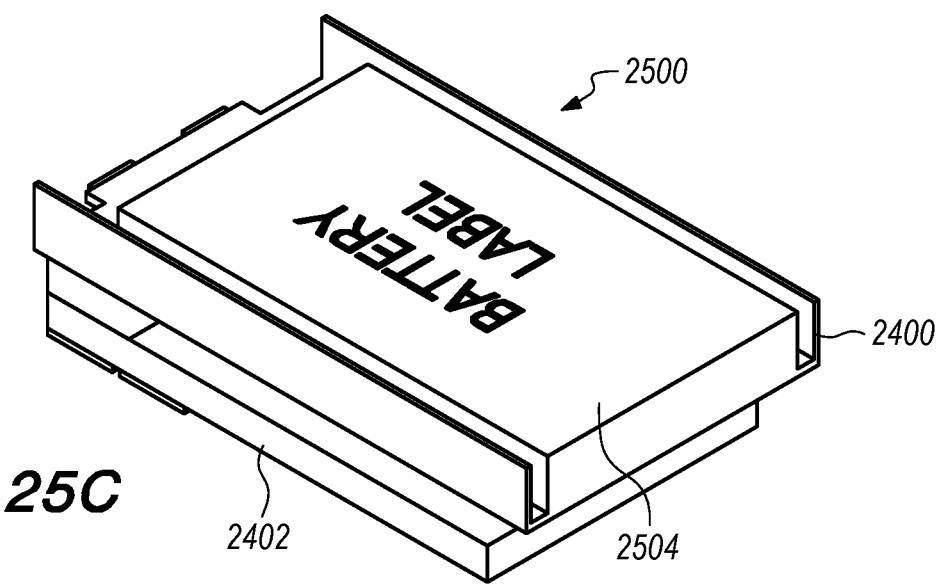

FIGS. 25A-39B depict an example method of assembling a medical device. FIGS. 25A-25B illustrate a method of attaching the battery 2400 to the PCB 2402 and folding the PCB 2402 and the battery 2400. The terminals 2412, 2414 of the battery 2400 are electrically connected to the contact pads 2416, 2418 of the PCB 2402 to form a PCB-battery assembly 2500. For example, the terminals 2412, 2414 can be soldered to the contact pads 2416, 2418. The terminal 2412 can be aligned with the ferrite inductor 611 when the terminals 2412, 2414 are electrically connected to the contact pads 2416, 2418.

In one embodiment, the battery 2400 is positioned bottom side up 2502 (e.g., label side down) when the terminals 2412, 2414 are electrically connected to the contact pads 2416, 2418. FIG. 25B depicts the battery 2400 folded over the PCB 2402. The terminals 2412, 2414 are bent such that the bottom side 2502 of the battery 2400 is positioned over the PCB 2402 and the top 2504 of the battery 2400 is visible (see FIG. 25C). In a non-limiting embodiment, the PCB 2402 can be held in a fixed position while the battery 2400 is pushed or rotated over the PCB 2402 so as to superpose the battery 2400 on the PCB 2402 (e.g., the battery 2400 is stacked over the PCB 2402).

Figure 26A:
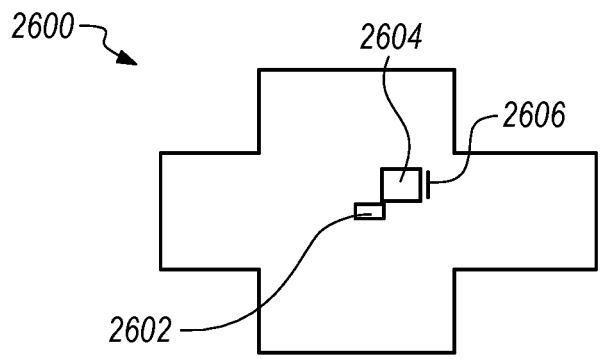
Figure 26B:
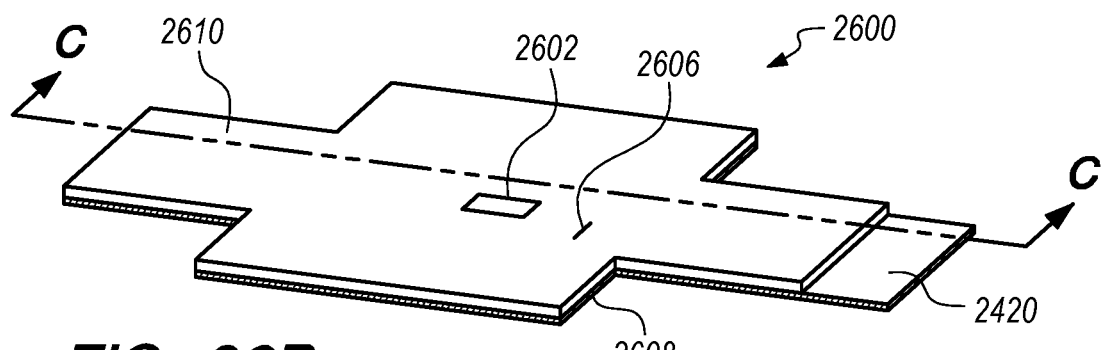
Figure 26C:
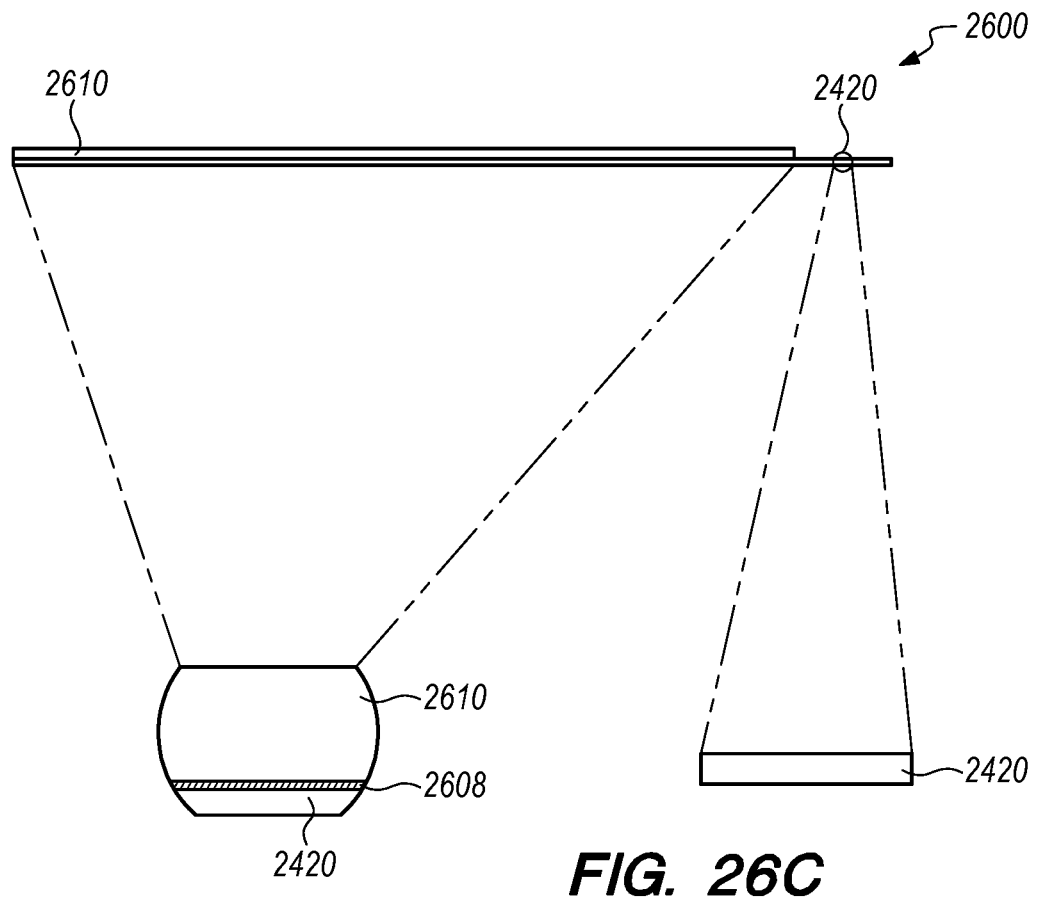

FIGS. 26A-26C illustrate an example tape encapsulation component that is part of the tape encapsulation assembly. FIG. 26A depicts a top view of the tape encapsulation component 2600. The tape encapsulation component 2600 includes a sensor window 2602 and a removable cover 2604. As will be described in more detail later, the optical sensor is aligned with the sensor window 2602.

FIG. 26B shows a bottom view of the tape encapsulation component. The tape encapsulation component 2600 includes a contact opening 2606 that extends through the tape encapsulation component 2600. As will be described in more detail later, the contact opening 2606 enables the removable first tab 1202 to be passed through the contact opening 2606 and extend to out of the opposite side of the tape encapsulation component 2600.

FIG. 26C illustrates a cross-sectional view of the tape encapsulation component taken along line C-C in FIG. 26B. The bottom surface of the tape encapsulation component 2600 includes the release liner 2420 that is disposed under an adhesive layer 2608. The adhesive layer 2608 is positioned under a backing layer 2610. In one embodiment, the backing layer 2610 comprises a foam backing layer. The tape encapsulation component 2600 may be manufactured by die cutting a biocompatible single-coated foam medical tape, although other embodiments are not limited to this implementation.

Figure 27:
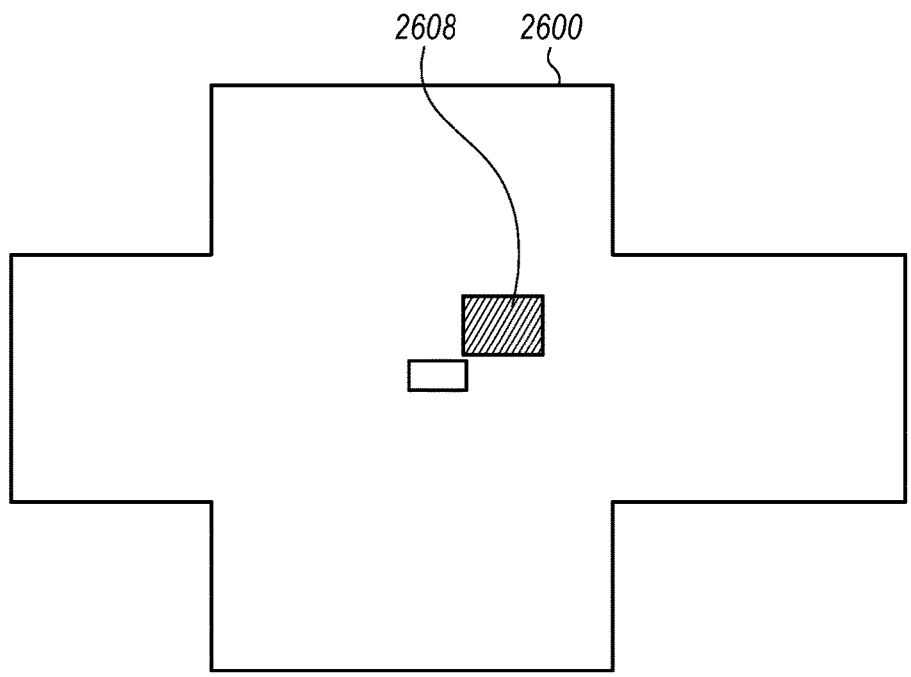

FIG. 27 depicts the top view of the tape encapsulation component with the removable cover removed. In one embodiment, the removable cover 2604 is kiss cut in the release liner 2420. When the removable cover 2604 is removed, a portion of the adhesive layer 2608 of the tape encapsulation component 2600 is exposed. Any suitable technique can be used to remove the removable cover 2604. In one embodiment, tongs or a pincer tool (e.g., a tweezer) is used to remove the cover 2604.

Figure 28:
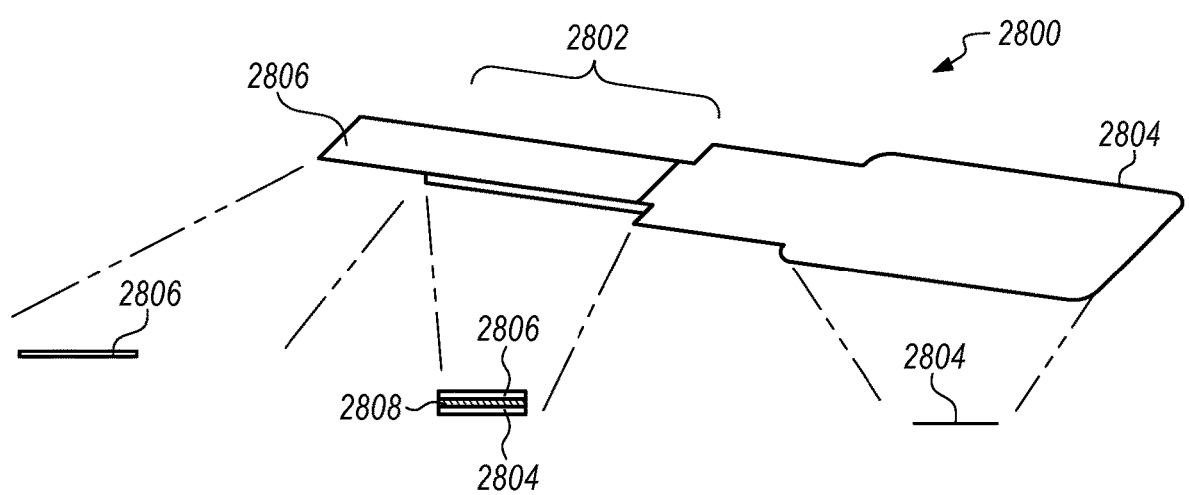

FIG. 28 illustrates an example third tab. The third tab 2800 can be used to transfer a conductive adhesive layer 2808 to the exposed portion of the adhesive layer 2608. The third tab 2800 includes a liner component 2802 and a liner tab 2804. A portion of the liner component 2802 includes the liner tab 2804 disposed under the conductive adhesive layer 2808. The conductive adhesive layer 2808 is positioned under a release liner 2806. In an example embodiment, the conductive adhesive layer 2808 is formed with conductive microfibers disposed on a conductive layer. Other embodiments can use a different type of a conductive adhesive layer.

Figure 29:
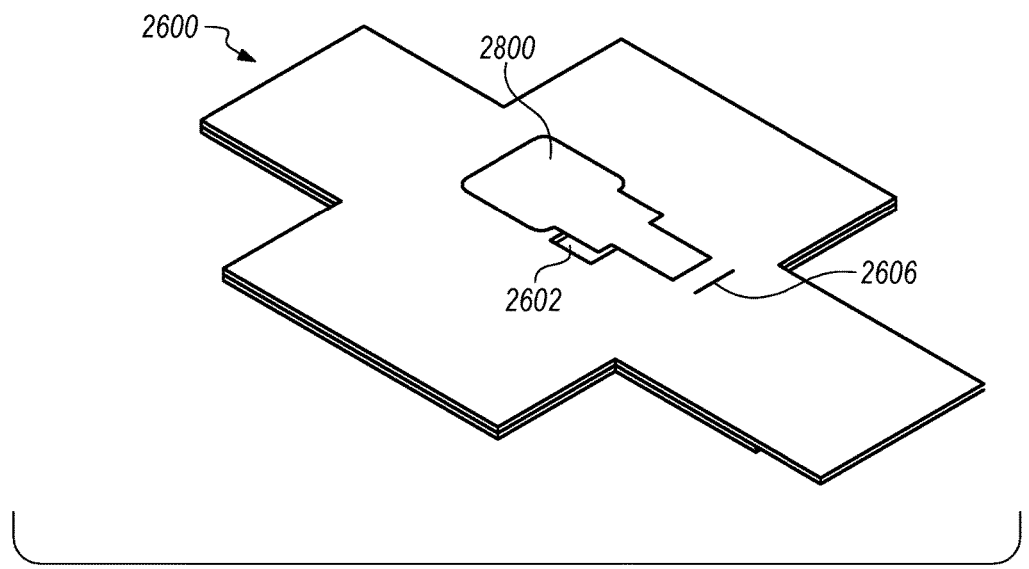
Figure 30:
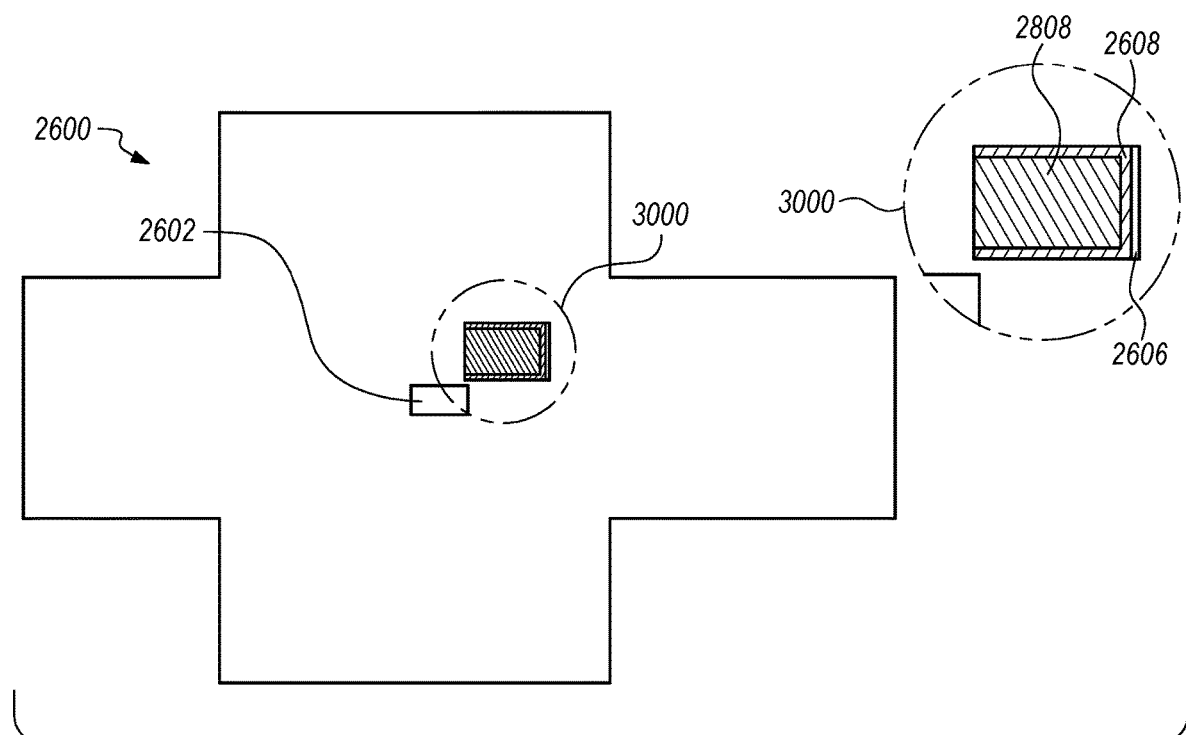

FIG. 29 depicts an example technique for transferring the conductive adhesive layer of the third tab to the tape encapsulation component. The third tab 2800 is aligned with the exposed portion of the adhesive layer 2608. In one embodiment, a gap is created between the edges of the contact opening 2606 and the end of the third tab 2800 (shown in enlarged view 3000 in FIG. 30). The third tab 2800 is then lightly pressed onto the exposed portion of the adhesive layer 2608 and removed to transfer the conductive adhesive layer 2808 to the exposed portion of the adhesive layer 2608. FIG. 30 illustrates the tape encapsulation component after the conductive adhesive layer is transferred to the exposed portion of the adhesive layer in the tape encapsulation component. As shown in the enlarged view 3000, the conductive adhesive layer 2808 is positioned on the adhesive layer 2608 such that the adhesive layer 2808 is disposed along one or more edges of the conductive adhesive layer 2608, leaving a gap between adhesive layer 2808 and contact opening 2606.

Figure 31:
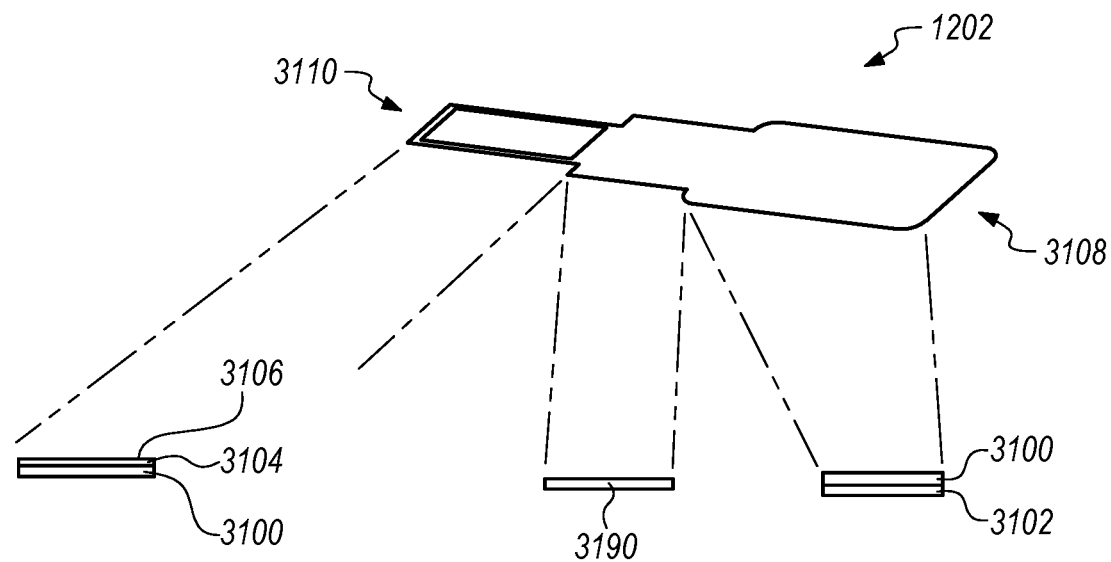
Figure 32:
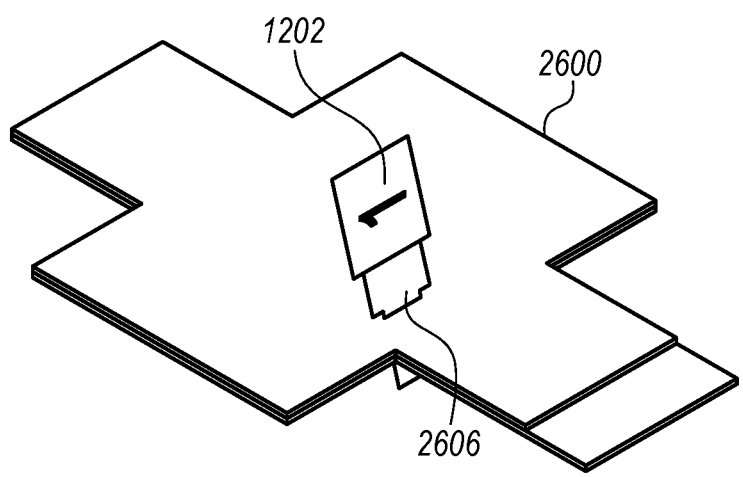

FIG. 31 depicts an example removable first tab. The removable first tab 1202 includes a liner layer 3100. A label 3102 is disposed under the liner layer 3100 at a first end 3108 of the removable first tab 1202. At the other end 3110 of the removable first tab 1202 the liner layer 3100 is positioned under an adhesive layer 3104. The adhesive layer is disposed under a support layer 3106. In a non-limiting embodiment, the surface of liner layer 3100 touching adhesive layer 3104 is a non-tacky silicon layer. The adhesive layer 3104 keeps the support layer 3106 attached to the liner layer 3100. The support layer 3106 is a metallic foil layer (e.g., a copper foil). The adhesive layer 3104 and the metallic foil layer 3106 provide additional mechanical strength to the end 3110 of the removable first tab 1202 to assist in extending the end 3110 into the contact opening 2606 of the tape encapsulation component 2600. FIG. 32 illustrates the removable first tab inserted into the contact opening of the tape encapsulation component.

Figure 33:
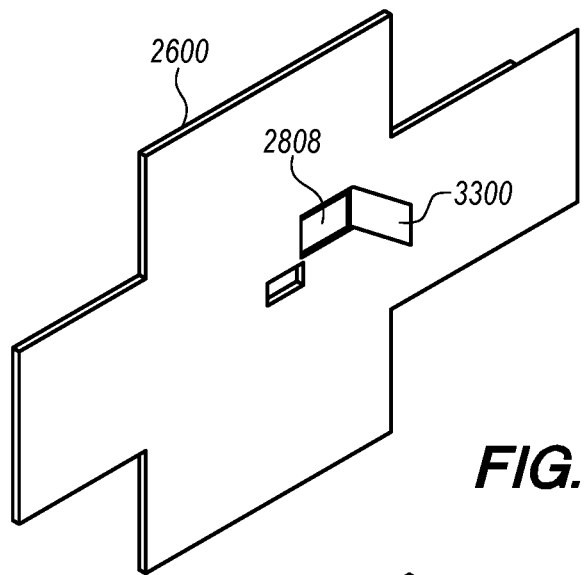

FIG. 33 depicts a perspective top view of the tape encapsulation component. The end 3110 of the removable first tab 1202 extends through the contact opening and forms a tab 3300. When the removable first tab 1202 is inserted into the contact opening, the removable first tab 1202 is positioned such that the support layer 3106 is adjacent the exposed conductive adhesive layer 2808. The support layer 3106 and the adhesive layer 3104 are removed from the tab 3300, which leaves the liner layer 3100 with non-tacky silicon surface facing the exposed conductive adhesive layer 2808.

Figure 34A:
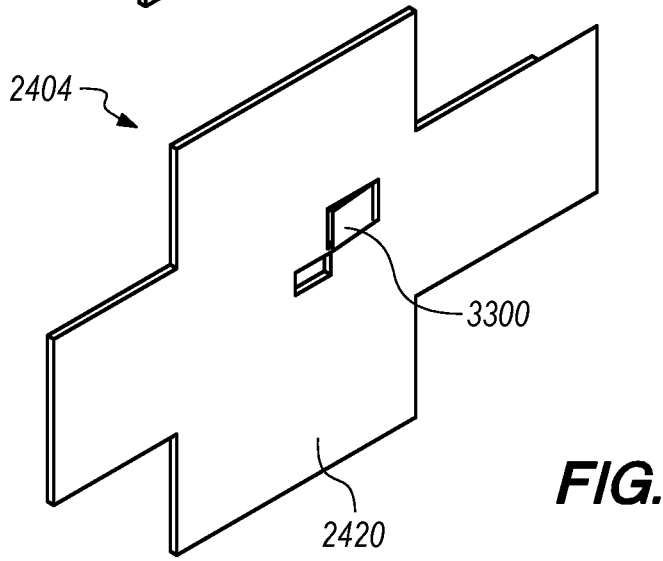
Figure 34B:
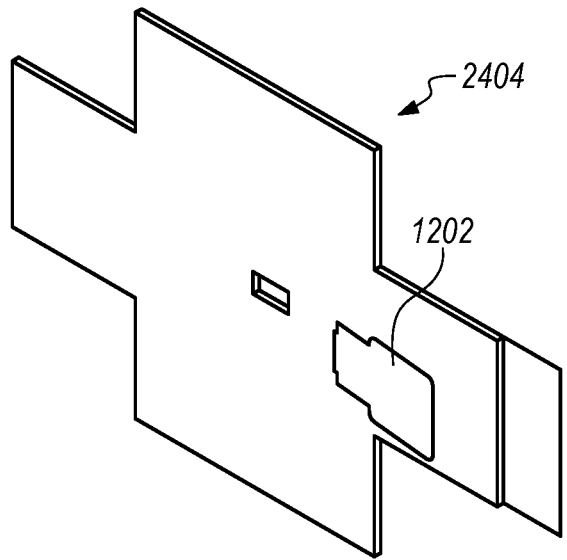

FIG. 34A illustrates the liner layer 3100 folded over the conductive adhesive layer. The liner layer 3100 is used to electrically isolate and protect the conductive adhesive layer 2808. The combination of the removable first tab 1202 attached to the tape encapsulation component 2600 produces the tape encapsulation assembly 2404. FIG. 34B depicts a bottom view of the tape encapsulation assembly. The removable first tab 1202 is bended and folded onto the backing layer 2610 of the tape encapsulation assembly 2404. In the illustrated embodiment, the removable first tab 1202 is folded over the backing layer 2610 with the number "1" facing the backing layer 2610.

Figure 35A:
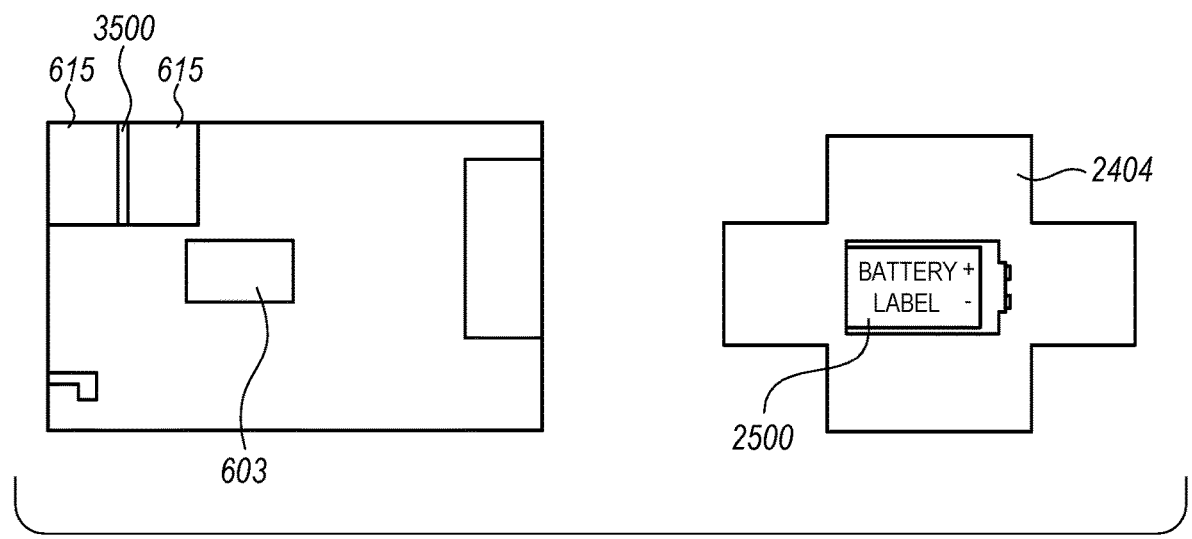
Figure 35B:
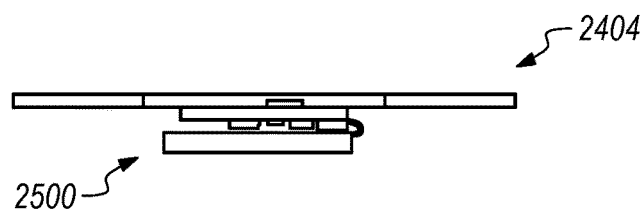

Once the tape encapsulation assembly 2404 is constructed, the PCB-battery assembly 2500 is attached to the tape encapsulation assembly 2404 (see FIG. 35A). Initially, the release liner 2420 is removed to expose the adhesive layer 2608. The PCB-battery assembly 2500 is positioned on the adhesive layer 2608 such that the optical sensor 603 on the PCB (shown on the left) is positioned over the sensor window 2602. The light source(s) 113 emit light through the sensor window 2602 and the photodetector(s) 114 receives reflected light through the sensor window 2602. Additionally, the (ON switch) contact pads 615 (see e.g., FIGS. 6C and 35A) on the PCB 2402 are aligned with the liner layer 3100 positioned over the conductive adhesive layer 2808. FIG. 35B is a side view showing the PCB-battery assembly 2500 attached to the tape encapsulation assembly 2404.

Figure 36A:
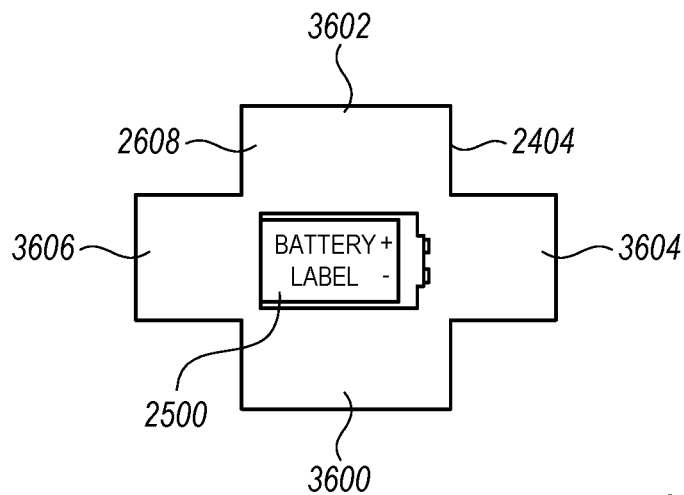

After the PCB-battery assembly 2500 is attached to the tape encapsulation assembly 2404, the tape encapsulation assembly 2404 is wrapped around the PCB-battery assembly 2500. FIGS. 36A-36E illustrate an example method of folding the tape encapsulation assembly around the PCB-battery assembly. As shown in FIG. 36A, the tape encapsulation assembly 2404 includes four tabs 3600, 3602, 3604, 3606. The surface of the four tabs 3600, 3602, 3604, 3606 is the adhesive layer 2608.

Figure 36B:
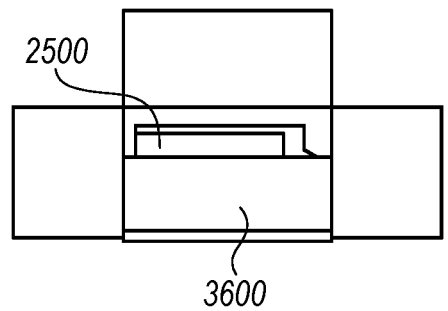
Figure 36C:
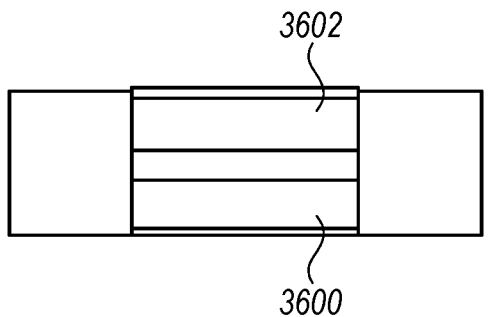
Figure 36D:
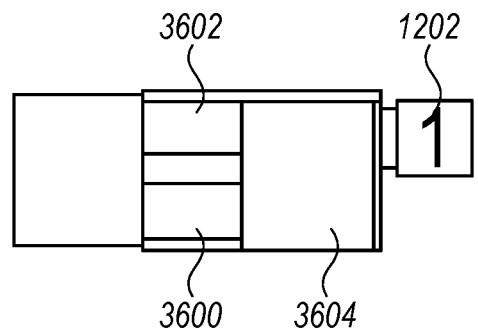
Figure 36E:
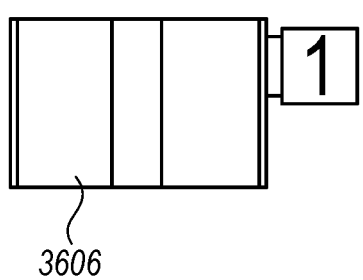

Initially, a first tab 3600 is folded over the PCB-battery assembly 2500 (FIG. 36B). A second tab 3602 is then folded over the PCB-battery assembly 2500 and the first tab 3600 (FIG. 36C). A third tab 3604 is folded over the PCB-battery assembly 2500 and the first and the second tabs 3600, 3602 (FIG. 36D). The removable first tab 1202 is visible (e.g., the "1") when the third tab 3604 is folded. Finally, a fourth tab 3606 is folded over the PCB-battery assembly 2500 and the first and the second tabs 3600, 3602 (FIG. 36E).

Figure 37A:
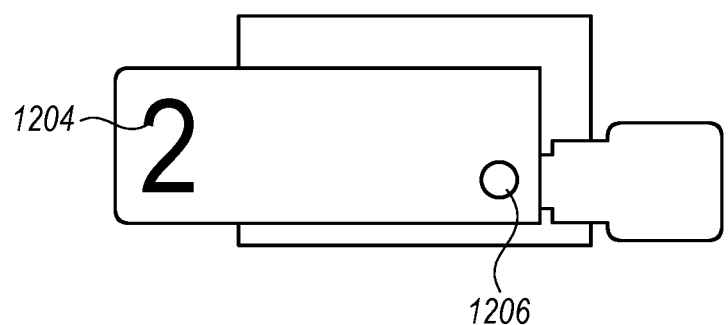
Figure 37B:
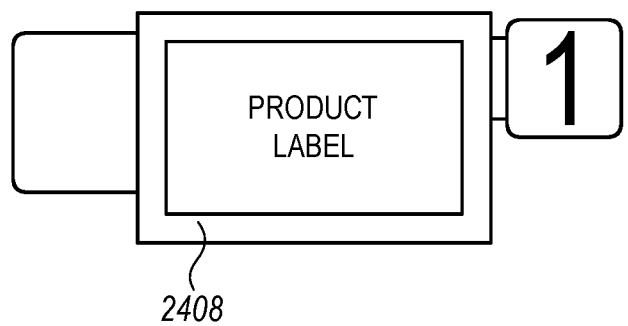

FIGS. 37A-37B illustrate an example method of attaching the removable second tab and the product label to the medical device. A liner (not shown) is removed from the product label 2408 to expose an adhesive surface on the underside of the product label 2408. The adhesive surface is then affixed to a bottom surface of the medical device (see FIG. 37B). Additionally, a liner layer (see 3806 in FIG. 38) is removed from the removable second tab 1204 to expose an adhesive layer (e.g., 3814 in FIG. 38) on the underside of the second tab 1204. The adhesive layer is then affixed to a top surface of the medical device. As shown in FIG. 37A, area 1206 (indicated by a circle) of the second tab 1204 is aligned (e.g., center aligned) with the end of the removable first tab 1202 (the end of the tab farthest from the number "1").

When constructed, the medical device 100 includes the PCB-battery assembly 2500, the tape encapsulation assembly 2404 wrapped around the PCB-battery assembly 2500, and the second removable tab 1204 positioned on a surface of the tape encapsulation assembly 2404. The second removable tab 1204 includes a two-sided adhesive layer that provides an adhesive layer (e.g., layer 1210 in FIG. 12D) on a surface of the medical device 100 when the second removable tab 1204 is removed from the medical device 100. The PCB 2402 includes the electronic circuitry that performs the functionalities of the medical device 100, including an optical sensor 603 that comprises at least one light source to emit light towards a measurement site of a user and at least one photodetector to receive light returned from the measurement site (e.g., 113 and 114 in FIG. 1). The PCB 2402 also includes at least one contact pad comprising an ON switch of the medical device (e.g., contact pad 615 in FIG. 35A). A battery 2400 is electrically attached to the PCB 2402. The tape encapsulation assembly 2404 includes a sensor window 2602 positioned over the optical sensor 603, and a contact opening 2606 extending through a tape encapsulation component 2600 for receiving a first removable tab 1202. The first removable tab 1202 includes a liner layer portion (e.g., tab 3300) disposed on a first surface of the tape encapsulation component 2600 covering the contact pad or pads on the PCB 2402 and a tab portion (e.g., pull-tab of 1202) disposed on an opposite second surface of the tape encapsulation component 2600. The liner layer portion (e.g., tab 3300) is positioned between the at least one contact pad (e.g., 615 in FIG. 35A) on the PCB 2402 and the conductive tape 2808 in the tape encapsulation component 2600.

FIG. 38 shows a cross-sectional view of an example removable second tab 1204. The second tab 1204 includes a first section 3800 and a second section 3802. The first section 3800 is formed with a first adhesive layer 3810 disposed between a first liner layer 3804 and a carrier layer 3812 and a second adhesive layer 3814 positioned between the carrier layer 3812 and a second liner 3806. The second section 3802 is formed with the first liner layer 3804 and the second liner layer 3806. A gap (e.g., an air gap) is positioned between the first liner layer 3804 and the second liner layer 3806. When the removable second tab 1204 is removed from the medical device 100, the adhesive layer 3810 remains on the top surface of the medical device 100. The adhesive layer 3810 is used to attach the medical device to the measurement site of the user (e.g., to a fingertip of the user).

Figure 39A:
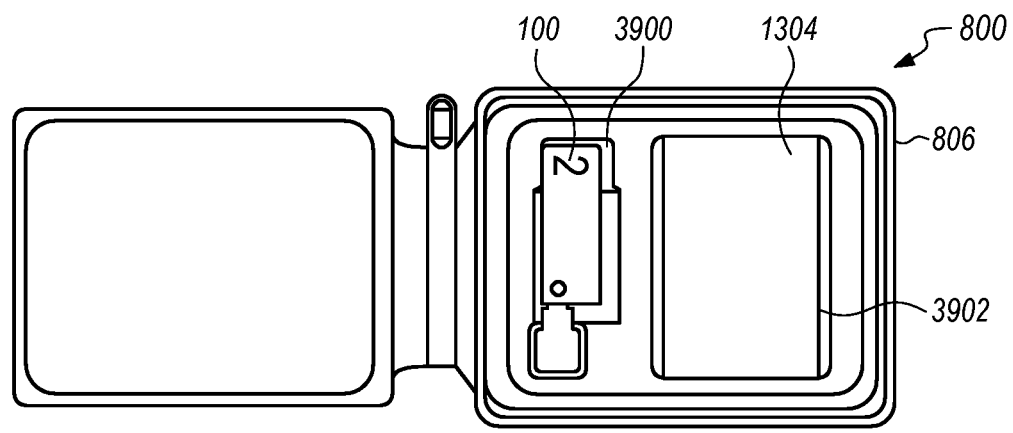
FIG. 39A-B depict a method of packaging the medical device in a container.
Figure 39B:
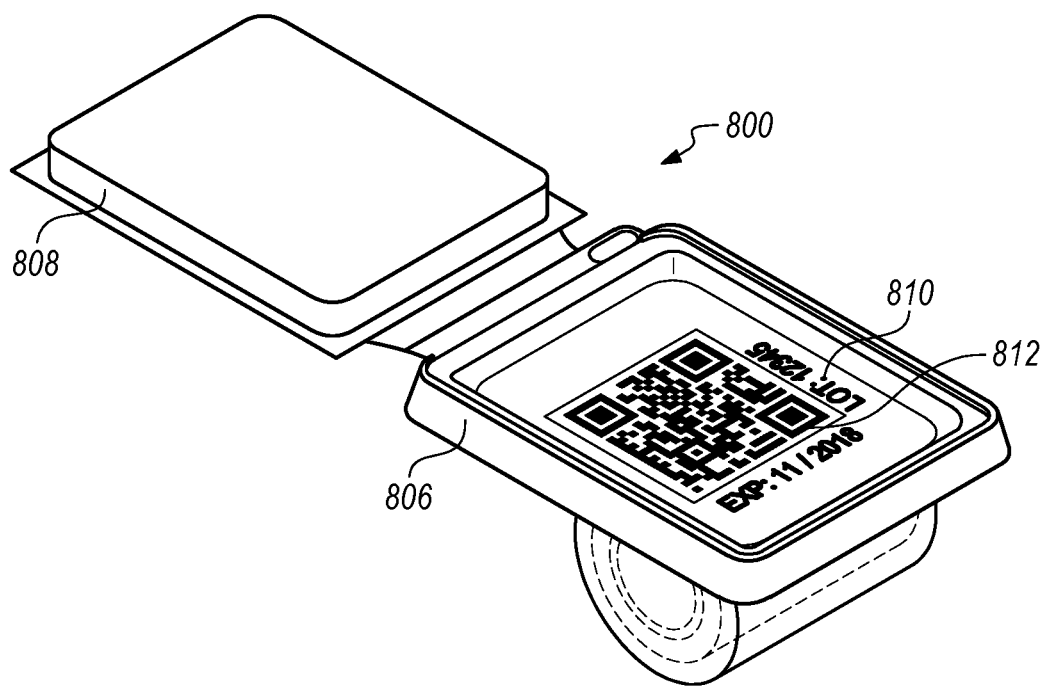

FIGS. 39A-39B depict a method of packaging the medical device in a container. As shown in FIG. 39A, the medical device 100 is positioned in a first molded area 3900 of the top portion 806 of the container 800 (FIG. 8) and a tape 1304 (e.g., biocompatible tape 802 in FIG. 8), is disposed in a second molded area 3902 of the top portion 806 of the container 800. In the illustrated embodiment, the second removable tab 1204 is visible when the medical device 100 is in the first molded area 3900, although this is not required. The label 810 (FIG. 8) is placed over the medical device 100 and the tape 1304. In the illustrated embodiment, the identifier 812 will be visible when the bottom portion 808 of the container 800 is attached to the top portion 806.

In another embodiment, the steps to assemble the tape encapsulation assembly 2404 can be modified by incorporating the conductive tape 2808 (FIG. 30) during the lamination and die cutting processes of tape encapsulation assembly 2404. In this way, the steps shown in FIGS. 29-30, as well as the removable third tab 2800, are eliminated because the conductive tape 2808 is included in the tape encapsulation assembly 2404. This can reduce the cost to manufacture the tape encapsulation assembly 2404.

In addition, to further reduce the manufacturing costs (i.e., tooling, labor) of the tape encapsulation assembly 2404, the release liner 2420 can be kiss cut to adhesive foam, and divided into multiple parts that can be more easily peeled off to facilitate the removal of the release liner 2420 and removable cover 2604 from the encapsulation assembly 2404 in the assembling process.

Figure 40A:
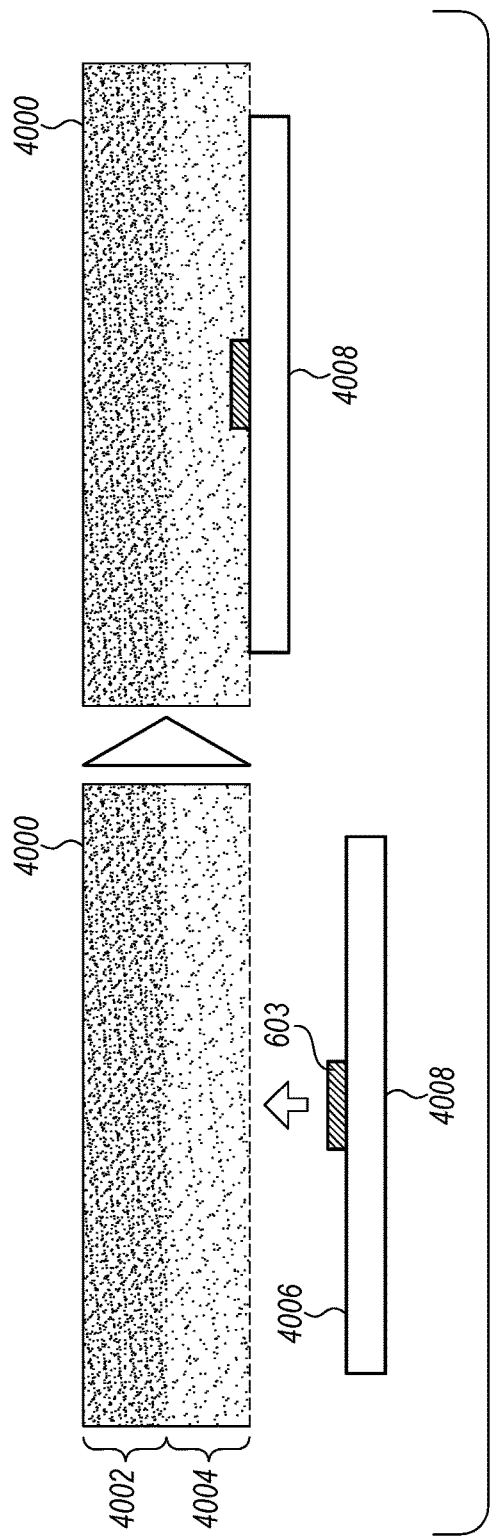
FIGS. 40A-40B illustrate different configurations of a printed circuit board of a medical device.
Figure 40B:
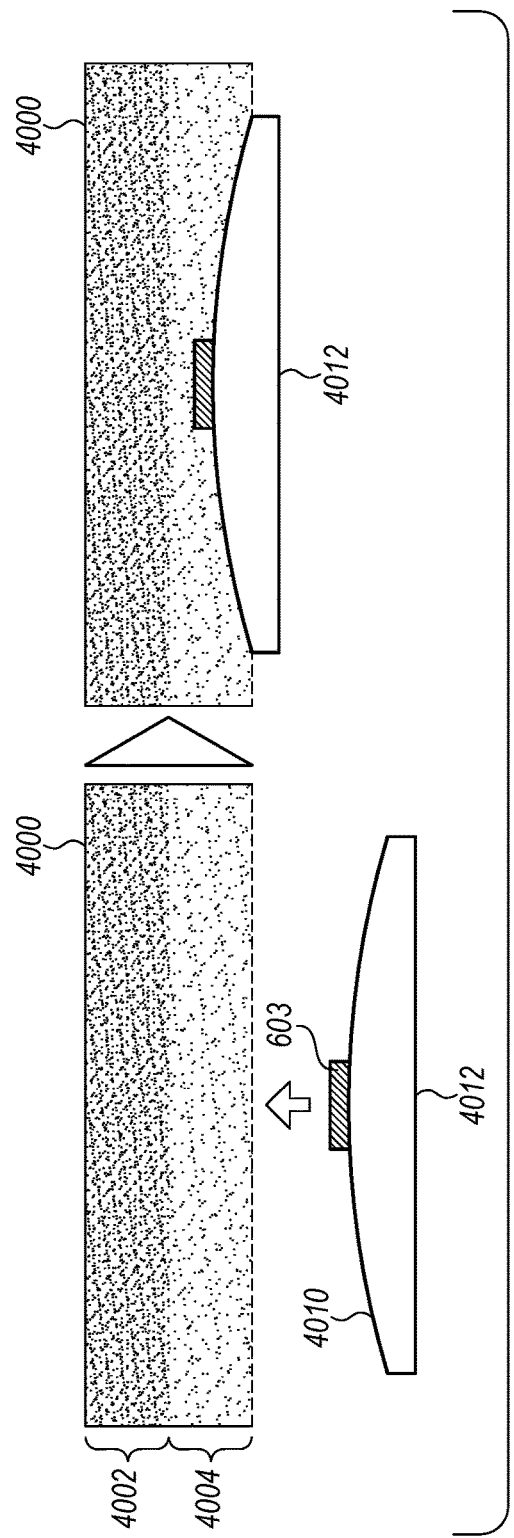

FIGS. 40A-40B illustrate different configurations of a printed circuit board of a medical device. A measurement site 4000 of a user is shown in FIGS. 40A-40B with a gradient filling. The darker region 4002 represents tissue having a higher peripheral blood circulation (dermis), or higher blood perfusion. The lighter region 4004, closer to the optical sensor 603, represents tissue having a lower peripheral blood circulation (epidermis), or lower blood perfusion. In FIG. 40A, the surface 4006 of a PCB 4008 (e.g., PCB 2402 in FIG. 24) in which the optical sensor 603 is attached to is flat. When the medical device is attached to the measurement site 4000, additional placement pressure may be needed to improve the optical compliance of the optical sensor 603 and the blood perfused tissue. This can be accomplished by using any suitable technique. For example, as described earlier, a tape 1304 (FIG. 13) may be wrapped around the medical device and the measurement site 4000. Additionally, an adhesive bandage can be applied over the medical device 100 and the measurement site 4000.

FIG. 40B depicts the surface 4010 of a PCB 4012 as a convex surface. When the surface 4010 is a convex surface, attaching the medical device to the measurement site 4000 with the tape 1304 creates additional placement pressure on the tissue around the location of the optical sensor 603, given that the convex surface bulges out and compresses the tissue. This improves the optical compliance of the optical sensor 603 and the measurement site 4000, as well as increases peripheral blood circulation around the location of the optical sensor 603. However, in other embodiments, the use of the tape 1304 or another attachment mechanism to attach the medical device to the measurement site 4000 is optional or unnecessary based on the convex surface, and only an adhesive layer (such as adhesive layer 1210 in FIG. 12D or 3814 in FIG. 38) that attaches the convex surface to the measurement site may be sufficient.

In one embodiment, the medical device, the host computing device, and associated methods and apparatuses described herein can represent a clinical-grade pulse oximetry system. FIG. 41 depicts example technical specifications of the medical device when used in combination with a host computing device. Other embodiments are not limited to any of the specifications shown in FIG. 41.

In one aspect, the example specifications 4100 can be obtained by design and through biocompatibility, EMC and electrical safety, environmental, bench, and clinical tests. A pulse oximetry system, for instance, is typically certified to comply with several electrical equipment safety standards, electromagnetic compatibility, and FCC standards. Example standards may include, but are not limited to: (i) IEC 60601-1-2:2014 Medical Electrical Equipment—Part 1-2: General requirements for basic safety and essential performance—Collateral Standard: Electromagnetic Compatibility—Requirements and Test. Safety Requirements for Electrical Equipment for Measurement, Control and Laboratory Use—Part 1: General Requirements; (ii) ANSI/AAMI ES 60601-1:2005/® 2012 Medical electrical equipment—Part 1: General requirement for basic safety and essential performance; (iii) 47 CFR Part 15 Subpart B Class B Devices and Innovation, Science; (iv) FCC Part 15, Subpart C and IC RSS-247, Issue 1, May 2015; etc.

The intended use 4102 can indicate uses such as measuring and displaying functional oxygen saturation of arterial hemoglobin (SpO2), pulse rate (PR), and perfusion rate (PI) of adult and pediatric patients. The pulse oximetry system can be intended for continuous monitoring of patients during non-motion and motion, and/or under well-perfused or poorly-perfused conditions. Example intended environments of use can be hospitals, clinics, doctor's offices, and domestic/residential settings.

A clinical-grade pulse oximetry system is commonly subjected to clinical testing to certify whether the pulse oximetry system meets the intended use 4102. For instance, in the case of a SpO2 accuracy clinical study recognized by the Food and Drug Administration (FDA), the pulse oximetry system may be tested in accordance to Code of Federal Regulations (CFR) for Non-Significant Risk (NSR) investigational studies, following ISO 14155:2011 as appropriate, and the pulse oximetry guidelines of ISO 80601-2-61:2011 applicable sections, and Pulse Oximeters—Premarket Notifications Submissions [510(k)s] Guidance For Industry and Food and Drug Administration Staff (issued: Mar. 4, 2013). The purpose of such a clinical study is to evaluate the SpO2 accuracy and performance during desaturations with medical devices placed on human subjects (fingers, forehead, temple, ear, etc.) over the range of 70-100% SaO2, arterial blood samples, assessed by CO-Oximetry. The objective is to show the SpO2 accuracy performance of the pulse oximetry system under test. Typically, a population of a given number of subjects (e.g., at least ten healthy adult subjects (male and female)), ranging in pigmentation from light to dark is enrolled into such a desaturation study. During the clinical tests, each subject is in a reclined position and connected to a breathing circuit, for administering medical grade oxygen and nitrogen. The gas flow delivery is adjusted for subject comfort. The gas mixture is controlled to various levels of induced hypoxia resulting in stable oxygen saturation plateaus between 100% and 70% SaO2. Arterial blood samples are drawn during simultaneous data collection from the pulse oximetry system under test. The arterial blood samples are immediately analyzed by Reference CO-Oximetry providing functional SaO2 for the basis of the SpO2 accuracy comparison.

Figure 42:
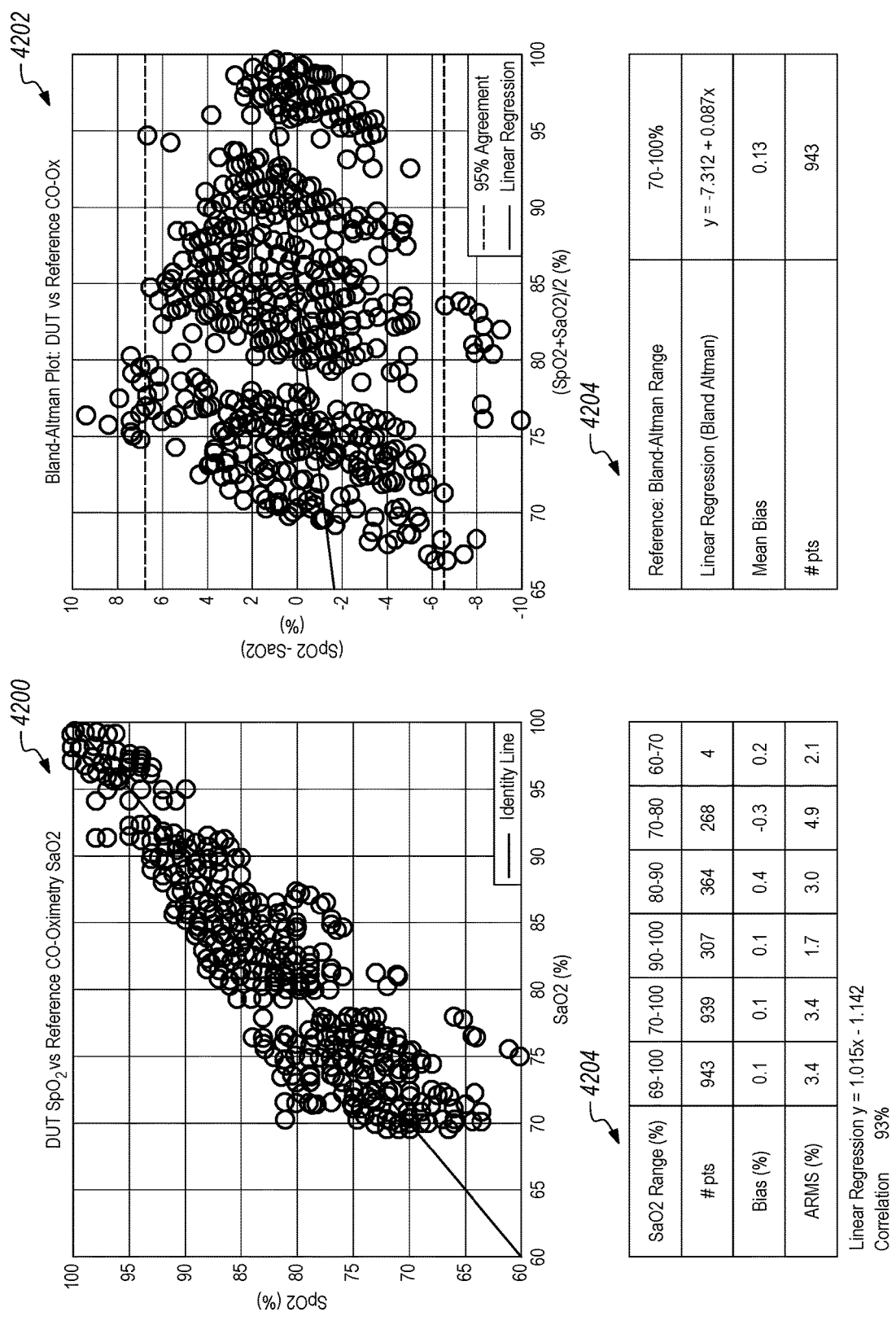
FIG. 42 illustrates an example scatter plot and an example Bland-Altman plot for a representative SpO2 clinical performance.

FIG. 42 depicts an example scatter plot 4200 and an example Bland-Altman plot 4202 illustrating a typical SpO2 clinical performance for a reflectance-based pulse oximetry system in the 70-100% SaO2 range. The performance metrics 4204 are in general the Accuracy Root Mean Square (Arms), bias, linear regression, correlation, etc. computed over a number of paired samples (SaO2, SpO2). For the plots depicted in FIG. 42, nine hundred and forty-three (943) paired samples, evenly spaced over the 70-100% SaO2 range, were used to compute the metrics 4204.

There are clinical and non-clinical applications where users or patients are given a high oxygen concentration by means of nasal cannula or facemask, or inside a hyperbaric chamber. These clinical and non-clinical applications are generally referred to as oxygen therapy. Oxygen therapy is the use of oxygen as a medical or wellness treatment, and is applied to carbon monoxide toxicity treatment, headache treatment, oxygen concentration supply during anesthesia procedures, and treatment of COPD (cystic fibrosis, etc.) in patients with chronically low oxygen saturation. Aviators may use a nasal oxygen cannula or wear an oxygen facemask when piloting airplanes with non-pressurized cabins at high altitudes, or during emergencies in order to keep their oxygen saturation at acceptable levels. Athletes may use nasal oxygen cannulas in order to increase performance or stay for a period of time in pressurized oxygen chambers in order to recover more quickly after workouts.

Typically, medical devices are calibrated via aforementioned clinical studies, where adult patients are subjected to oxygen desaturations over the range of 70-100% SaO2. These patients are typically healthy adults with normal cardiorespiratory systems. Typically, health adult patients will have a measured SaO2 of 97-100% at normal arterial oxygen partial pressure. However, patients still have a percentage of hemoglobin with some of their oxygen-binding sites still empty at normal arterial oxygen partial pressure. This implies that, if such patients or users are exposed to a higher concentration of oxygen (such as during oxygen therapy), additional hemoglobin sites will bind to oxygen molecules. However, this increase cannot be captured by conventional medical devices because they are calibrated to measure 100% SpO2 at normal arterial oxygen partial pressures. Higher values are typically truncated to 100%, because the clinical community and regulatory agencies have adopted the convention that SpO2 should be limited to 100%, since it is a saturation (concentration) measure. What may be missed is the fact that the 100% saturation value is the result of instrument calibration by means of desaturation studies, and is applicable to patients and users with normal cardiorespiratory systems and not subjected to oxygen therapy. For patients under oxygen therapy, the ability to read oxygen saturation values higher than 100% is very useful, because it may guide physicians and/or caregivers in terms of oxygen partial pressure settings to be administered to a particular patient (based on SpO2 readings above 100%), and also to serve as a metric for treatment of patients with compromised cardiorespiratory systems (under oxygen therapy).

Co-oximeters (such as the ABL90 FLEX from Radiometer) provide a range of indication for SaO2 (e.g., the arterial oxygen saturation in the blood measured by a co-oximeter) above 100% (102% for the ABL90 FLEX). Typically, the user has the option to activate the "Out-of-range suppression" option and prevent the co-oximeter from reporting values higher than 100%. These in-vitro instruments have SaO2 accuracy better than 1%. The range of indication above 100% is built-in so as to account for measurement errors, as well as to provide clinicians with SaO2 reading values above 100% for patients under oxygen therapy. The inconvenience of such in-vitro instruments (co-oximeters) has to do with their inability to provide continuous measurements, as well as the need for arterial blood samples. Therefore, a non-invasive pulse oximetry system, such as the medical device disclosed herein operating in combination with a host computing device that can also monitor SpO2 continuously for values above 100%, can be invaluable in clinical settings where oxygen therapy is required.

Figure 43:
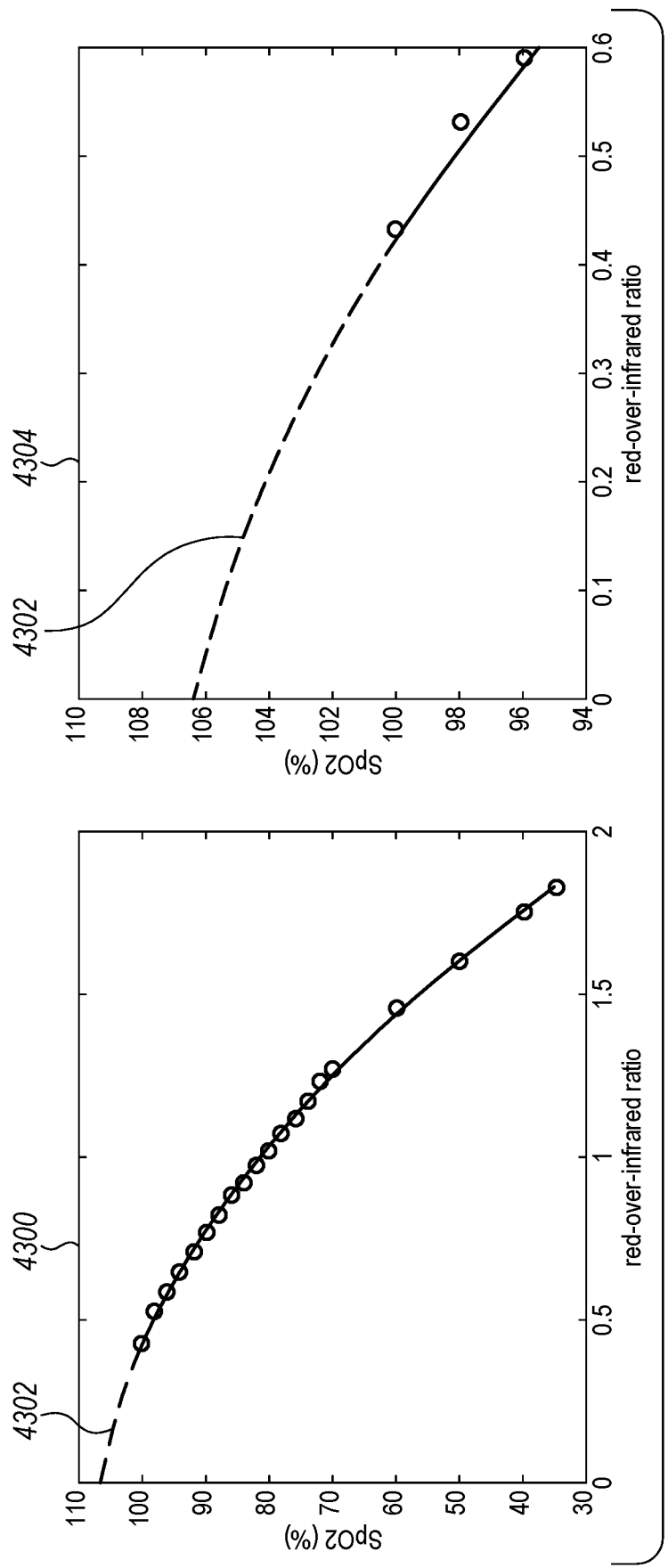
FIG. 43 depicts experimental points of an example calibration curve for a pulse oximetry system.

FIG. 43 illustrates experimental points (circles) of a typical calibration curve (calcurve) 4300 for a pulse oximetry system. FIG. 43 maps optical ratios (red over infrared) produced by the pulse oximetry system into SpO2 values. Such a calcurve is usually obtained experimentally by means of clinical studies, such as the ones aforementioned, where patients are subjected to oxygen desaturations, or via optical and physiological modeling using photon-diffusion methods (e.g., Boltzmann's Transport Equation), or via a combination of modeling and experimental data. To enable a medical device to measure and display SpO2 readings above 100%, the calcurve is extrapolated for SaO2 values above 100%. In the case of this particular experimental calcurve, a red-over-infrared ratio of 0.42 corresponds to 100% SpO2. To extrapolate the calcurve, a curve can be fit to the experimental points and then, the resulting curve's expression can be used to extrapolate for red-over-infrared ratios below 0.42 (i.e., SpO2 values above 100%). FIG. 43 depicts a dashed line 4302 representing a smooth extrapolation after the experimental data (circles) are fit to a quadratic polynomial. In some embodiments, the resulting calcurve polynomial is defined by the following equation:

$$y = -16.79x^2 - 8.19x + 106.43, \qquad \text{Equation 2}$$

where x is the red-over-infrared ratio value, and y is the SpO2 value. The "red-over-infrared" ratio not necessarily is obtained or calculated by dividing two quantities (the red photoplethysmograph over the infrared photoplethysmograph). Because of numerical stability, noise, and interferences, the division may be replaced with iterative methods that find the best linear relation between the two quantities of interest. The calculated linear relation will be an estimate for the ratio and can be used as a value for x in Equation 2. The "red-over-infrared" ratio can also represent more complex ratiometric relations between red and infrared photoplethysmographs, and also calculated through iterative methods.

Other fittings such as cubic, exponential, etc. can be used to yield similar results. In addition, constrained optimization (fitting) combined with photon-diffusion models can be applied to find an extrapolated curve that satisfies both the calcurve experimental (model) data and the hill's equation (with a cubic term for better accuracy, such as the one disclosed by John W. Severinghaus, in Simple, Accurate Equations for Human Blood O2 Dissociation Computations. J. Appl. Physiol: Respirat. Environ. Exercise Physiol. 46(3): 599-602, 1979. Revisions, 1999, 2002, 2007) for a given nominal partial pressure of oxygen. FIG. 43 also depicts a magnified view 4304 of the extrapolated SpO2 calcurve 4302.

Figure 44:
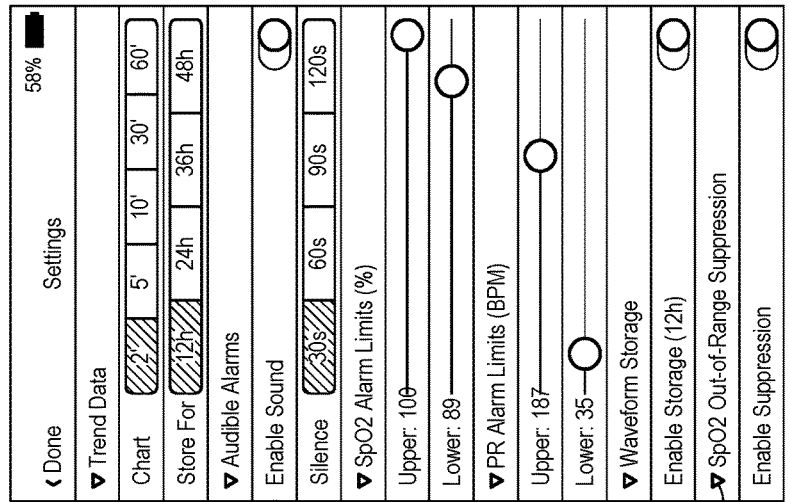
FIG. 44 illustrates a measurement user interface view of an Application software that can be displayed on a host computing device.

In terms of displaying SpO2 for values above 100%, the pulse oximetry system can offer the same option ("Out-of-range suppression") as the one available in conventional in-vitro co-oximeters. FIG. 44 depicts a measurement user interface view of an Application software that can be displayed on a host computing device. The SpO2 measurement type 4400 displays a numerical value 4202 of 102.3%. Note that a tenth place value was added to the numerical value 4402 (when SpO2 is greater than 100%), so as to give clinicians higher measurement granularity, and to compensate for the smaller dynamic range for SpO2 values above 100%.

Figure 45:
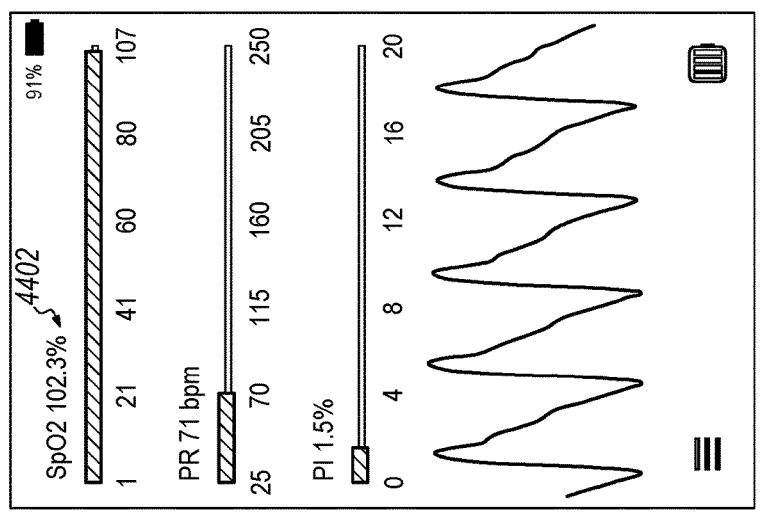
FIG. 45 depicts an example settings user interface view of an Application software that can be displayed on a host computing device.

FIG. 45 illustrates an example settings user interface view of an Application software that can be displayed on a host computing device. The user interface view 4500 includes a setting 4502 for "SpO2 out-of-range suppression". This setting provides a clinician with the option to display (or not display) SpO2 values above 100%. The dashed line in FIGS. 44 and 45 represents a host computing device and the user interface view is displayed on a display device (e.g., a touchscreen).

Figure 48:
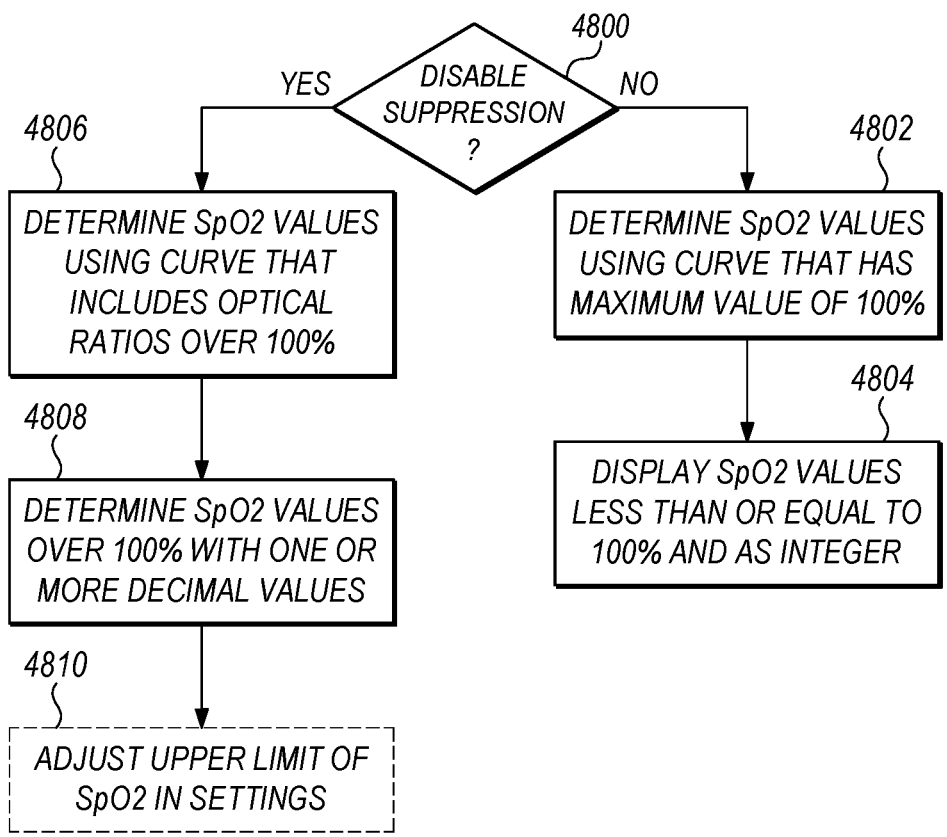
FIG. 48 is a flowchart illustrating an example method of providing SpO2 values that exceed one hundred percent.

Returning to FIG. 41, the measurement ranges for SpO2 are shown with the "SpO2 out-of-range suppression" enabled 4104 and disabled 4106. In one embodiment, the maximum value of the extended SpO2 range can be 107%, which can be obtained by rounding up the SpO2 value computed from the extended calcurve 4102 (FIG. 41) for a red-over-infrared ratio equals to zero. FIG. 48 shows an example method for providing SpO2 values over 100%.

Another aspect of implementing an extrapolated SpO2 calcurve 4102 in a magnified view 4104 (see FIG. 41) relates to the recommendations described in ISO 80601-2-61:2011, the standard for basic safety and essential performance of pulse oximeter equipment. According to ISO 80601-2-61: 2011 (section EE.2.3.4 Data analysis), an invasive controlled desaturation study data analysis should be performed as follows: "for pulse oximeter monitors that place an upper limit on displayed SpO2 (e.g. 99% or 100%), a means that does not bias the Arms result should be used. EXAMPLE 1—Include only observations where SpO2 readings are less than the upper display limit; EXAMPLE 2—Statistically down-weight those values with SpO2=100% (e.g. treat observations of 100% as censored, as is done in the analysis of survival data); EXAMPLE 3—Configure the data-collection system to record values of SpO2>100%."

Therefore, "EXAMPLE 3" enables SpO2 data collected above 100% by the pulse oximetry system under test (during a controlled desaturation clinical study) to be used to compute its SpO2 Arms accuracy. No special considerations or exclusions, such as in "EXAMPLE 1" and "EXAMPLE 2", are needed. "EXAMPLE 3" is enabled by means of an extrapolated SpO2 calcurve 4102 (FIG. 41), where the "SpO2 Out-of-Range Suppression" setting is to be disabled.

There are other pulse oximetry solutions that display ad hoc proprietary indexes to monitor patients under oxygen therapy. In these implementations, indexes typically vary from zero to one, where the zero value corresponds to an arbitrary lower limit, and one to an arbitrary upper limit. This approach can be confusing, and not very practical for clinicians. Clinicians are typically trained to interpret values of SpO2 in the normal range and unit (scale). Displaying SpO2 values above 100%, in the same scale as the values of SpO2 in the normal range (0-100%), is not only natural, but also enables physicians and other health care providers to use their clinical experience (as far as interpreting SpO2 readings in the standard scale) to make more accurate clinical decisions on patients under oxygen therapy. The use of an index is not based on scientific principles. It can be a strategy to enable medical device manufacturers to claim monitoring capabilities during oxygen therapy without providing accuracy claims based on scientific methods. In addition, because indexes use unit-less scales, manufacturers have the freedom to disclose measurement principles that are in line with their strategy, and not necessarily in agreement with scientific methods and principles. The extrapolated SpO2 calcurve, such as the calcurve 4102, is a model-based and data-based approach to measure and display SpO2 values above 100% from patients under oxygen therapy, and provides a scientific-based alternative to arbitrary and ad hoc indexes currently available in the marketplace.

Some of the features for a particular embodiment of a clinical-grade pulse oximetry system, with associated methods and apparatuses disclosed herein, can be described as follows ((1) through (5)):

(1) System components: The clinical-grade pulse oximetry system is comprised of two components:
 1. A wireless, continuous, fully disposable, single-use medical device (e.g., medical device 100).
 2. An Application software installed in a host computing device (e.g., host computing device 105).

The Application software controls the operation of the host computing device, so as to enable wireless connection via low-energy wireless protocol with the medical device 100, and provides user graphical interface, data storage and management interface, and sound interface for alarms/warnings. In some embodiments, for safety and effectiveness, the medical device 100 can only connect and communicate to a host computing device that has the Application software installed and running. No other wireless products or devices may be able to make a wireless connection to the medical device 100

(2) Wireless communication: The purpose of wireless data transfer between the medical device and the host computing device is to enable the monitoring (e.g., continuous monitoring) of SpO2, PR, and PI, the generation of alarms (e.g., visual and audible alarms), and data storage. In this particular embodiment, the medical device does not possess a user interface, input/output devices (i.e., display, speaker, keyboard), or any long-term data storage capability. The medical device controls the electronics in the medical device so as to collect high-fidelity optical data continuously from the red and infrared regions, process the data to produce waveforms and diagnostics, and send all the acquired and processed real-time data wirelessly and continuously to the host computing device (e.g., the Application software). The host computing device then calculates SpO2, PR, and PI measurements (e.g., continuously and in real-time) from the received data. In one embodiment, the host computing device calculates SpO2, PR, and PI measurements according to the method described in conjunction with FIG. 7. Each real-time data package sent wirelessly by the medical device and received by the host computing device is time stamped, and can be also saved to a database that logs waveforms and diagnostics parameters (i.e., LED currents, electronic gains, ambient light intensity, battery voltage, device temperature, etc.). The wireless throughput (bandwidth) can be as low as 450 bytes per second. This can make the wireless communication between the medical device and the host computing device reliable. In some embodiments, the wireless real-time transfer of waveforms (or data associated with the waveforms) can occur simultaneously with the wireless real-time transfer of diagnostics parameters. The waveforms sent to the host computing device have a sampling rate that ensures appropriate bandwidth (e.g., 25 Hz), so as to keep a high-fidelity representation of the photoplethysmographs that are processed, displayed, and stored by the host computing device. All the other measurements and diagnostics can be updated at a sampling frequency as low as 1 or 2 Hz. This is sufficient to capture fast transients related to the real-time monitoring of SpO2, PR, and PI measurements and diagnostics. The Application software running on the host computing device measures wireless data integrity in real-time. Because the data is time stamped, any transmission delays that may occur during operation cause the Application software to issue one or more alarms (e.g., audible and visual alarms) at the host computing device (or on any other device operably connected to the host computing device) to inform or alert the user. However, the low data throughput (450 bytes per second) can cause such delay events to be rare, provided that the separation distance between the medical device and the host computing device is within the wireless range (e.g., spherical radius ≤10 meters). In some instances, wireless data buffering can be kept to a minimum (e.g., around one tenth of a second) to enable reliable and real-time data transmission between the medical device and the host computing device.

(3) Alarm system: To alert users to abnormal conditions and/or warnings, the clinical-grade pulse oximetry system can provide the following alarm features:
1. SpO2 and PR upper and lower limit alarms: When SpO2 or PR value crosses an alarm limit, the corresponding gauge is highlighted (e.g., turns red and blinks), and an alarm (e.g., audible alarm) is issued to alert user. The SpO2 and PR alarm limits are set by the user.
2. Silence alarm activation: Once an alarm is activated, the user has the option to silence the alarm momentarily by touching the affected measurement type, gauge, or numerical value (e.g., the highlighted measurement type, gauge, numerical value) displayed on the screen of the host computing device. The user can set the alarm silence duration using the settings user interface (e.g., FIG. 18).
3. Off patient alarm: The clinical-grade pulse oximetry system can have one or more algorithms capable of detecting whenever the medical device has been removed from the patient. This information triggers one or more alarms (e.g., audible and/or visual alarms) at the host computing device or any device operably connected to the host computing device.
4. Out of range alarm: The Application software issues one or more alarms (e.g., visual and/or audible alarms) whenever the medical device is out of range from the host computing device.
5. Low battery alarms: Once the non-rechargeable battery of the medical device is discharged, the Application software issues one or more alarms (e.g., visual and/or audible alarms). The host computing device can also produce multiple warnings and notifications for the user when the battery capacity of the host computing device drops below a certain threshold (e.g., 20%).
6. Alarms while the Application software is in background mode: The host computing device can run multiple applications in addition to the Application software. When the Application software is in background mode, with another application running in the foreground, one or more alarms (e.g., audible alarms) are still issued normally and whenever required by the Application software.
7. Alarms while the host computing device is in low power mode, airplane mode, and silent mode: In some host computing devices (e.g., iOS devices, Android devices, etc.), to increase battery life as well disable audio and wireless radios whenever necessary, several operation modes are available to the user. One or more alarms can be issued normally and whenever required regardless of the operation mode. In the case of airplane mode, because the wireless radios are disabled, the Application software may always issue one or more alarms to alert user (4) Single Application mode: There are clinical applications where it is desirable to have the host computing device restricted to a single Application (i.e., the pulse oximetry system Application software), with hardware buttons and the icon 1642 (FIG. 16) disabled, so as to prevent unauthorized users from disabling alarms permanently, or from changing the Application settings. In such instances, the host computing device functions like a dedicated medical device monitor. With the icon 1642 disabled, unauthorized users cannot change (disable) alarm settings. In one embodiment, the Application software can be designed to be compliant with Apple's iOS™ "Guided Access" mode. The Guided Access mode temporarily restricts an iOS™ device (host computing device) to a single Application, and lets the user control which Application features are available. The following describes example default behavior of an Application during a Guided Access section:
1. Application termination is disabled: User needs to enter Guided Access password to exit Guided Access mode to terminate the Application.
2. Side drawer menu (icon 1642 in FIG. 16) is disabled: User needs to enter Guided Access password to exit Guided Access mode in order to make changes in the Application settings.
3. Portrait and landscape views enabled: User is allowed to change from portrait to landscape mode without authentication. The switching between portrait and landscape views, and vice-versa can be deactivated by just disabling "Motion" in the iOS™ Guided Access Options menu.
4. Hardware buttons disabled (i.e., volume, sleep/wake, etc.): User is required to enter Guided Access password in order to enable the hardware buttons.
5. User can silence alarms temporarily by taping on gauge (screen) of affected parameter (i.e., SpO2 or PR): However, alarms (e.g., audible and/or visual) will be enabled upon silence time interval expiration. Silence activation can also be disabled during a Guided Access session, by just disabling "Touch" in the iOS™ Guided Access Options menu.

(5) Mobile Device Management (MDM): In some organizations, such as hospitals and clinics, a plurality of medical devices (e.g., pulse oximetry systems) may be deployed. In such situations, it can be convenient and practical to have a MDM framework that manages over the air (remotely) the pulse oximetry systems. The Application software can be designed to be compatible with commercial MDM frameworks. This enables organizations to manage Application software distribution, configuration, settings, and data flow in a centralized fashion, such as for alarm systems, where alarm events (e.g., SpO2 and PR upper and lower limits, off patient, device out of range, low battery, etc. event alarms) from each pulse oximetry system are relayed to the appropriate hospital areas and/or caregivers. MDM frameworks can simplify and standardize the management and operation of a plurality of host computing devices working in combination with a plurality of medical devices, so as to form a network of pulse oximetry systems such as the ones described herein.

Figure 46:
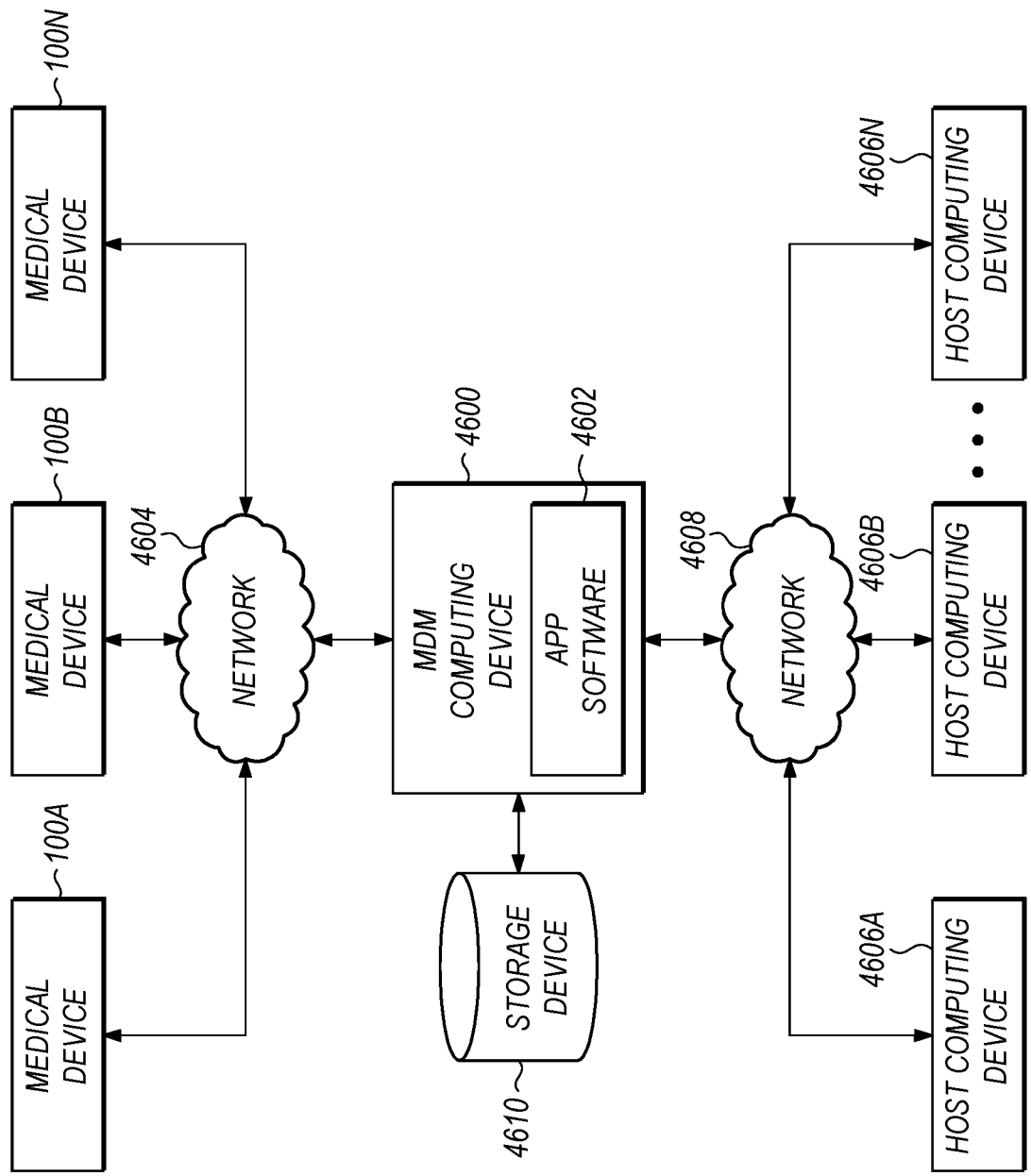
FIG. 46 illustrates a first example Mobile Device Management system.

FIG. 46 shows a first example of a Mobile Device Management system. One or more MDM computing devices (represented by MDM computing device 4600) run and/or manage the Application software 4602 as well as program and configure host computing devices and/or medical devices. Multiple medical devices 100A, 100B, . . . , 100N transmit and receive data from the MDM computing device 4600 via network 4604. The network 4604 represents one or more intranet networks and/or internet networks (wireless and/or wired). Multiple host computing devices 4606A, 4606B, . . . , 4606N transmit and receive data from MDM computing device 4600 via network 4608. The network 4608 represents one or more intranet networks and/or internet networks (wireless and/or wired). The network 4604 and the network 4608 can be the same network(s) or different network(s). In some embodiments, the MDM computing device 4600 acts as an agent that manages the Application ("App") 4602 software distribution, configuration, and settings on host and/or medical devices, and data flow from medical and/or host computing devices in a centralized fashion.

In some embodiments, the MDM computing device 4600, the medical devices 100A, 100B, . . . , 100N, and/or the host computing devices 4606A, 4606B, . . . , 4606N store data in one or more storage devices (represented by storage device 4610).

Figure 47:
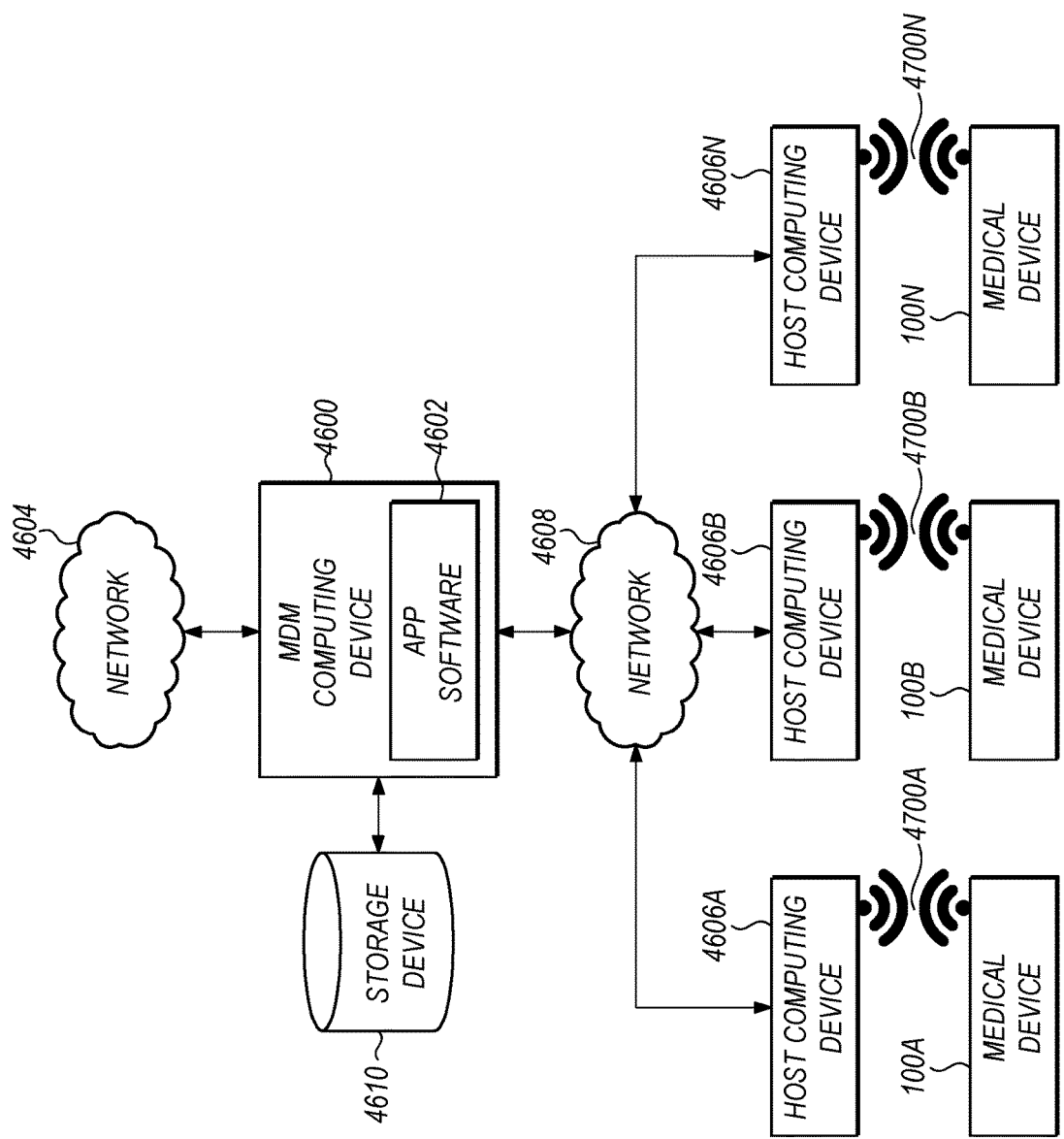
FIG. 47 depicts a second example Mobile Device Management system.

FIG. 47 depicts a second example MDM system. In this embodiment, multiple medical devices 100A, 100B, . . . , 100N transmit and receive data from their respective host computing devices 4606A, 4606B, . . . , 4606N by means of wireless low energy radios 4700A, 4700B, . . . , 4700N (examples of which include, but are not limited to, BLE, ANT, Zigbee, etc.). The host computing devices 4606A, 4606B, . . . , 4606N transmit and receive data from MDM computing device 4600 via network 4608. In this embodiment, the MDM computing device 4600 manages the App 4602 software distribution, configuration, settings, and data flow in a centralized fashion, for each system comprised of a medical device (i.e., 100A, 100B, . . . , 100N) and a host computing device (i.e., 4606A, 4606B, . . . , 4606N). An example of such a system can be a clinical-grade pulse oximetry system, with associated methods and apparatuses disclosed herein. An example of software distribution can be the deployment of the Application software 4602 on the host computing devices 4606A, 4606B, . . . , 4606N via network 4608. The host computing devices in turn can also deploy firmware images (stored as data structure(s) and/or file(s) in the Application software 4602) on the medical devices (i.e., 100A, 100B, . . . , 100N) via wireless connection (i.e., 4700A, 4700B, . . . , 4700N), so as to ensure all medical devices run the same firmware version. A data flow example can be for alarm systems, where alarm events (e.g., SpO2 and PR upper and lower limits, off patient, device out of range, low battery, etc. event alarms) from each pulse oximetry system are relayed to the appropriate hospital areas and/or caregivers via the MDM computing device 4600. A configuration example can be for configuring an Application software 4602 (that runs on host computing devices 4606A, 4606B, . . . , 4606N) to have the same configuration throughout the whole organization (e.g., hospitals, clinics, etc.), or to have a specific configuration that is function of the unit (e.g., pediatrics unit, intensive care unit, surgical observation unit, etc.) where the pulse oximetry system is located. The network 4604 can be used to relay/receive information to/from third-party computing systems and devices not connected to the network 4608, or when networks 4604 and 4608 cannot be connected together (or cannot be the same) because of technical/security reasons. The networks 4604 and 4608 represent one or more intranet networks and/or internet networks (wireless and/or wired).

FIG. 48 is a flowchart illustrating a method of providing SpO2 values that exceed one hundred percent. Initially, a determination is made at block 4800 as to whether the "SpO2 Out-of-Range Suppression" is disabled (see 4502 in FIG. 45). If suppression is enabled, the process passes to block 4802 where the SpO2 value(s) is determined using a calcurve or plot that has a maximum SpO2 value of 100%. Any SpO2 values that exceed 100% may be rounded down to 100%. The SpO2 value or values are provided to an output device (e.g., a display) as an integer number that is equal to or less than 100% (block 4804).

When a determination is made at block 4800 that suppression is disabled, the method continues at block 4806 where the SpO2 value(s) is determined using a calcurve or plot that has a maximum value greater than 100%. For example, as described earlier, the maximum value can be 107%. The calcurve includes or represents optical ratios (red over infrared) over 100%. In some instances, a curve can be fit to the values and then the resulting curve's expression can be used to extrapolate SpO2 values above 100%. At block 4808, the SpO2 value(s) is provided to an output device (e.g., a display) and represented by a whole number and one or more decimal place values (e.g., tenths place value, hundredths place value, etc.). Optionally, at block 4810, the upper limit of the SpO2 value for an alarm can be automatically adjusted to a value over 100% (e.g., the maximum value over 100%). For example, as shown in FIG. 18, the upper limit in the SpO2 Alarm Limits setting 1812 can be automatically adjusted to a value higher than 100%.

As used herein, the terms "component", "operation", and "functionality" (and derivatives thereof) each refer to an aspect of the invention that can be implemented as hardware (e.g., circuitry), software, or combinations of hardware and software.

As should be appreciated, the components and operations depicted in FIGS. 1-48, and the corresponding descriptions of FIGS. 1-48, are for purposes of illustration only and are not intended to limit embodiments to a particular sequence of steps, or a particular combination of hardware or software components.

Aspects of the present disclosure, for example, are described above with reference to block diagrams and/or operational illustrations of methods, systems, and computer program products according to aspects of the disclosure. The functions/acts noted in the blocks may occur out of the order, as shown in any flowchart. For example, two blocks shown in succession may, in fact, be executed substantially concurrently or the blocks may sometimes be executed in the reverse order, depending upon the functionality/acts involved. Additionally, one or more blocks can be omitted or added to the operations shown in the flowcharts.

The description and illustration of one or more aspects provided in this application are not intended to limit or restrict the scope of the disclosure as claimed in any way. The aspects, examples, and details provided in this application are considered sufficient to convey possession and enable others to make and use the best mode of claimed disclosure. The claimed disclosure should not be construed as being limited to any aspect, example, or detail provided in this application. Regardless of whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate aspects falling within the spirit of the broader aspects of the general inventive concept embodied in this application that do not depart from the broader scope of the claimed disclosure.

What is claimed is:

1. A system, comprising:
  a processing device; and
  a memory storing instructions, that when executed by the processing device, cause operations of:
    receiving measurement values that represent measurement data that is received continuously from a pulse oximetry system;
    based on the measurement values, continuously determining oxygen saturation values using a curve that maps the measurement values into the oxygen saturation values, wherein the curve has a maximum value that is greater than one hundred percent and at least one oxygen saturation value in the oxygen saturation values exceeds one hundred percent; and
    causing the oxygen saturation values to be provided to a display device for presentation on the display device.

2. The system of claim 1, wherein the curve comprises a curve that is extrapolated for oxygen saturation values over one hundred percent.

3. The system of claim 2, wherein the curve represents optical ratios to oxygen saturation values.

4. The system of claim 3, wherein the optical ratios comprise red over infrared optical ratios.

5. The system of claim 1, wherein the at least one oxygen saturation value that exceeds one hundred percent is represented as a whole number and one or more decimal place values.

6. The system of claim 1, further comprising a wireless communication device, wherein the measurement data is received continuously from the pulse oximetry system via the wireless communication device.

7. The system of claim 1, wherein the memory stores further instructions for receiving an input to disable an out-of-range suppression operation to enable reporting of oxygen saturation values that exceed one hundred percent.

8. A method for continuously providing oxygen saturation values, the method comprising:
  continuously receiving measurement values from a pulse oximetry system;
  based on the measurement values, continuously determining oxygen saturation values using a curve that maps the measurement values into the oxygen saturation values, wherein the curve has a maximum value that is greater than one hundred percent and at least one oxygen saturation value in the oxygen saturation values exceeds one hundred percent; and
  causing the oxygen saturation values to be provided to a display device for presentation in a user interface on the display device.

9. The method of claim 8, wherein:
the user interface comprises a first user interface; and
the method further comprises:
  causing display of a second user interface that presents an input element for setting an upper limit for the oxygen saturation values;
  receiving, via the input element, a setting of the upper limit for the oxygen saturation values; and
  providing an alarm to an output device in response to determining at least one of the oxygen saturation values exceeds the upper limit.

10. The method of claim 9, further comprising receiving, via the input element, an adjustment of the upper limit.

11. The method of claim 9, wherein the alarm comprises an audible alarm.

12. The method of claim 9, wherein:
the input element comprises a first input element; and
the method further comprises receiving, via a second input element, an input to disable an out-of-range suppression operation to enable reporting of oxygen saturation values that exceed one hundred percent.

13. The method of claim 12, wherein the second input element is presented in the second user interface.

14. The method of claim 8, wherein the curve comprises a curve that is extrapolated for oxygen saturation values over one hundred percent.

15. The method of claim 8, wherein the at least one oxygen saturation value that exceeds one hundred percent is represented as a whole number and one or more decimal place values.

16. A system, comprising:
  a pulse oximeter device, comprising:
    an optical sensor comprising a light emitter to emit light towards a measurement site and a light detector to detect light acquired from the measurement site;
    a first wireless communication device;
    a first processor operably connected to the optical sensor and the first wireless communication device;
    a first memory for storing instructions, that when executed by the first processor, cause operations of:
      causing the light emitter to emit light;
      receiving signals from the light detector;
      based on the signals, transmitting, using the first wireless communication device, measurement values to a computing device; and
  the computing device, comprising:
    a second wireless communication device;
    a second processor operably connected to the second wireless communication device; and
    a second memory for storing instructions, that when executed by the second processor, cause operations of:
      receiving, from the pulse oximeter device using the second wireless communication device, the measurement values;

based on the measurement values, determining oxygen saturation values using a curve that has a maximum value that is greater than one hundred percent, wherein at least one oxygen saturation value in the oxygen saturation values exceeds one hundred percent; and causing display of the oxygen saturation values on a display device.

17. The system of claim 16, wherein the second memory stores further instructions for:

causing display of a user interface that presents a first input element for setting an upper limit for the oxygen saturation values and a second input element for setting a lower limit for the oxygen saturation values;

receiving, via the first input element, a setting of the upper limit for the oxygen saturation values;

receiving, via the second input element, a setting of the lower limit for the oxygen saturation values; and providing an alarm to an output device in response to determining at least one of the determined oxygen saturation values is greater than the upper limit or is less than the lower limit.

18. The system of claim 17, wherein providing the alarm to the output device comprises providing a visual alarm to the display device.

19. The system of claim 16, wherein the measurement data received by the second wireless communication device comprise at least one of photoplethysmograph data or data from which photoplethysmograph data can be extracted.

20. The system of claim 16, wherein the second memory stores further instructions for receiving, via a third input element, an input to disable an out-of-range suppression operation to enable reporting of oxygen saturation values that exceed one hundred percent.

* * * * *